(12) United States Patent
Unger et al.

(10) Patent No.: US 6,479,034 B1
(45) Date of Patent: *Nov. 12, 2002

(54) METHOD OF PREPARING GAS AND GASEOUS PRECURSOR-FILLED MICROSPHERES

(75) Inventors: Evan C. Unger, Tucson, AZ (US); Thomas A. Fritz, Tucson, AZ (US); Terry Matsunaga, Tucson, AZ (US); VaradaRajan Ramaswami, Tucson, AZ (US); David Yellowhair, Tucson, AZ (US); Guanli Wu, Tucson, AZ (US)

(73) Assignee: Bristol-Myers Squibb Medical Imaging, Inc., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/118,329

(22) Filed: Jul. 17, 1998

Related U.S. Application Data

(60) Division of application No. 08/487,230, filed on Jun. 6, 1995, now Pat. No. 5,853,752, which is a division of application No. 08/159,687, filed on Nov. 30, 1993, which is a continuation-in-part of application No. 08/160,232, filed on Nov. 30, 1993, now Pat. No. 5,542,935, which is a continuation-in-part of application No. 08/159,674, filed on Nov. 30, 1993, now abandoned, which is a continuation-in-part of application No. 08/076,239, filed on Jun. 11, 1993, now Pat. No. 5,469,854, which is a continuation-in-part of application No. 07/717,084, filed on Jun. 18, 1991, now Pat. No. 5,228,446, which is a continuation-in-part of application No. 07/716,899, filed on Jun. 18, 1991, now abandoned, which is a continuation-in-part of application No. 07/569,828, filed on Aug. 20, 1990, now Pat. No. 5,088,499, which is a continuation-in-part of application No. 07/455,707, filed on Dec. 22, 1989, now abandoned.

(51) Int. Cl.[7] .............................. A61B 8/00; A61K 9/127
(52) U.S. Cl. ........................ 424/9.51; 424/9.5; 424/9.52; 424/9.51; 424/450; 424/459
(58) Field of Search .................................. 424/9.5, 9.52, 424/489, 1.21, 450

(56) References Cited

U.S. PATENT DOCUMENTS

| 3,015,128 A | 1/1962 | Sommerville et al. ........ 18/2.6 |
|---|---|---|
| 3,291,843 A | 12/1966 | Fritz et al. .................. 260/614 |
| 3,293,114 A | 12/1966 | Kenaga et al. .............. 162/167 |
| 3,479,811 A | 11/1969 | Walters ...................... 57/153 |
| 3,488,714 A | 1/1970 | Walters et al. .............. 161/161 |
| 3,532,500 A | 10/1970 | Priest et al. .................. 96/91 |
| 3,557,294 A | 1/1971 | Dear et al. .................. 424/342 |
| 3,594,326 A | 7/1971 | Himmel et al. ............. 252/316 |

(List continued on next page.)

FOREIGN PATENT DOCUMENTS

| AU | 641363 | 3/1990 |
|---|---|---|
| AU | B-30351/89 | 3/1993 |
| DE | 25 21 003 | 8/1976 |
| DE | 3803972 | 8/1989 |

(List continued on next page.)

OTHER PUBLICATIONS

Frézard, F., et al., "Fluorinated phosphatidylcholine–based liposomes: $H^+/Na^+$ permeability, active doxorubicin encapsulation and stability in human serum," BBA, XP–000990899, 1994, 1194, 61–68.

(List continued on next page.)

Primary Examiner—Russell Travers
(74) Attorney, Agent, or Firm—Woodcock Washburn LLP

(57) ABSTRACT

Methods of and apparatus for preparing temperature activated gaseous precursor-filled liposomes are described. Gaseous precursor-filled liposomes prepared by these methods are particularly useful, for example, in ultrasonic imaging applications and in therapeutic drug delivery systems.

62 Claims, 12 Drawing Sheets

U.S. PATENT DOCUMENTS

| | | | |
|---|---|---|---|
| 3,615,972 A | 10/1971 | Morehouse et al. | 156/79 |
| 3,650,831 A | 3/1972 | Jungermann et al. | 134/27 |
| 3,732,172 A | 5/1973 | Herbig et al. | 252/316 |
| 3,873,564 A | 3/1975 | Schneider et al. | 270/309.6 |
| 3,945,956 A | 3/1976 | Garner | 270/2.5 B |
| 3,960,583 A | 6/1976 | Netting et al. | 106/122 |
| 3,968,203 A | 7/1976 | Spitzer et al. | 424/47 |
| 4,027,007 A | 5/1977 | Messina | 424/46 |
| 4,089,801 A | 5/1978 | Schneider | 252/316 |
| 4,108,806 A | 8/1978 | Cohrs et al. | 521/54 |
| 4,138,383 A | 2/1979 | Rembaum et al. | 270/29.7 H |
| 4,162,282 A | 7/1979 | Fulwyler et al. | 274/9 |
| 4,179,546 A | 12/1979 | Garner et al. | 521/56 |
| 4,192,859 A | 3/1980 | Mackaness et al. | 424/5 |
| 4,224,179 A | 9/1980 | Schneider | 252/316 |
| 4,229,360 A | 10/1980 | Schneider et al. | 270/403 |
| 4,265,251 A | 5/1981 | Tickner | 128/660 |
| 4,276,885 A | 7/1981 | Tickner et al. | 128/660 |
| 4,310,505 A | 1/1982 | Baldeschwieler et al. | 424/1 |
| 4,310,506 A | 1/1982 | Baldeschwieler et al. | 424/1 |
| 4,315,514 A | 2/1982 | Drewes et al. | 128/653 |
| 4,331,654 A | 5/1982 | Morris | 424/38 |
| 4,342,826 A | 8/1982 | Cole | 435/7 |
| 4,344,929 A | 8/1982 | Bonsen et al. | 424/15 |
| 4,420,442 A | 12/1983 | Sands | 274/13 |
| 4,421,562 A | 12/1983 | Sands et al. | 106/75 |
| 4,427,330 A | 1/1984 | Sears | 270/403 |
| 4,427,649 A | 1/1984 | Dingle et al. | 424/38 |
| 4,428,924 A | 1/1984 | Millington | 424/4 |
| 4,442,843 A | 4/1984 | Rasor et al. | 128/660 |
| 4,466,442 A | 8/1984 | Hilmann et al. | 128/653 |
| 4,485,193 A | 11/1984 | Rubens et al. | 521/58 |
| 4,530,360 A | 7/1985 | Duarte | 128/419 F |
| 4,533,254 A | 8/1985 | Cook et al. | 366/176 |
| 4,534,899 A | 8/1985 | Sears | 270/403 |
| 4,540,629 A | 9/1985 | Sands et al. | 428/402 |
| 4,544,545 A | 10/1985 | Ryan et al. | 424/1.1 |
| 4,549,892 A | 10/1985 | Baker et al. | 65/21.4 |
| 4,569,836 A | 2/1986 | Gordon | |
| 4,572,203 A | 2/1986 | Feinstein | 128/661 |
| 4,586,512 A | 5/1986 | Do-huu et al. | 128/660 |
| 4,603,044 A | 7/1986 | Geho et al. | 424/9 |
| 4,615,879 A | 10/1986 | Runge et al. | 424/9 |
| 4,620,546 A | 11/1986 | Aida et al. | 128/660 |
| 4,646,756 A | 3/1987 | Watmough et al. | 128/804 |
| 4,657,756 A | 4/1987 | Rasor et al. | 424/9 |
| 4,658,828 A | 4/1987 | Dory | 128/660 |
| 4,663,161 A | 5/1987 | Mannino et al. | 424/89 |
| 4,675,310 A | 6/1987 | Chapman et al. | 514/6 |
| 4,681,119 A | 7/1987 | Rasor et al. | 128/660 |
| 4,684,479 A | 8/1987 | D'Arrigo | 252/307 |
| 4,689,986 A | 9/1987 | Carson et al. | 73/19 |
| 4,693,999 A | 9/1987 | Axelsson et al. | 514/174 |
| 4,718,433 A | 1/1988 | Feinstein | 128/660 |
| 4,728,575 A | 3/1988 | Gamble et al. | 428/402.2 |
| 4,728,578 A | 3/1988 | Higgins et al. | 428/462 |
| 4,731,239 A | 3/1988 | Gordon | 424/9 |
| 4,737,323 A | 4/1988 | Martin et al. | 274/4.3 |
| 4,774,958 A | 10/1988 | Feinstein | 128/660.01 |
| 4,775,522 A | 10/1988 | Clark, Jr. | 424/9 |
| 4,776,991 A | 10/1988 | Farmer et al. | 274/4.3 |
| 4,781,871 A | 11/1988 | West, III et al. | 274/4.3 |
| 4,789,501 A | 12/1988 | Day et al. | 252/645 |
| 4,790,891 A | 12/1988 | Halliday et al. | 149/2 |
| 4,822,534 A | 4/1989 | Lencki et al. | 274/4.3 |
| 4,830,858 A | 5/1989 | Payne et al. | 424/450 |
| 4,834,964 A | 5/1989 | Rosen | 424/9 |
| 4,844,882 A | 7/1989 | Widder et al. | 424/9 |
| 4,863,717 A | 9/1989 | Keana | 424/9 |
| 4,865,836 A | 9/1989 | Long, Jr. | 424/5 |
| 4,877,561 A | 10/1989 | Iga et al. | 274/4.3 |
| 4,893,624 A | 1/1990 | Lele | 128/399 |
| 4,895,719 A | 1/1990 | Radhakrishnan | 424/45 |
| 4,898,734 A | 2/1990 | Mathiowitz et al. | 424/427 |
| 4,900,540 A | 2/1990 | Ryan et al. | 424/9 |
| 4,918,065 A | 4/1990 | Stindl et al. | 514/179 |
| 4,919,895 A | 4/1990 | Heldebrant et al. | 422/129 |
| 4,921,706 A | 5/1990 | Roberts et al. | 424/450 |
| 4,927,623 A | 5/1990 | Long, Jr. | 424/5 |
| 4,933,121 A | 6/1990 | Law et al. | 264/4.3 |
| 4,938,947 A | 7/1990 | Nicolau et al. | 424/1.1 |
| 4,957,656 A | 9/1990 | Cerny et al. | 252/311 |
| 4,972,002 A | 11/1990 | Volkert | 521/120 |
| 4,981,692 A | 1/1991 | Popescu et al. | 424/422 |
| 4,984,573 A | 1/1991 | Leunbach | 128/653 |
| 4,985,550 A | 1/1991 | Charpiot et al. | 536/18.4 |
| 4,987,154 A | 1/1991 | Long, Jr. | 514/772 |
| 4,993,415 A | 2/1991 | Long | 128/653 A |
| 4,996,041 A | 2/1991 | Arai et al. | 424/9 |
| 5,000,960 A | 3/1991 | Wallach | 424/450 |
| 5,004,611 A | 4/1991 | Leigh | 424/450 |
| 5,008,050 A | 4/1991 | Cullis et al. | 274/4.3 |
| 5,008,109 A | 4/1991 | Tin | 424/422 |
| 5,013,556 A | 5/1991 | Woodle et al. | 424/450 |
| 5,019,370 A | 5/1991 | Jay et al. | 424/4 |
| 5,045,304 A | 9/1991 | Schneider et al. | 424/9 |
| 5,049,388 A | 9/1991 | Knight et al. | 424/450 |
| 4,229,360 A | 11/1991 | Schneider et al. | 270/403 |
| 5,078,994 A | 1/1992 | Nair et al. | 424/501 |
| 5,088,499 A | 2/1992 | Unger | 128/662.2 |
| 5,107,842 A | 4/1992 | Levene et al. | 128/662.02 |
| 5,114,703 A | 5/1992 | Wolf et al. | 424/5 |
| 5,123,414 A | 6/1992 | Unger | 128/654 |
| 5,135,000 A | 8/1992 | Akselrod et al. | 128/662.02 |
| 5,137,928 A | 8/1992 | Erbel et al. | 521/56 |
| 5,141,738 A | 8/1992 | Rasor et al. | 424/2 |
| 5,147,631 A | 9/1992 | Glajch et al. | 424/9 |
| 5,149,319 A | 9/1992 | Unger | 604/22 |
| 5,171,755 A | 12/1992 | Kaufman | 514/759 |
| 5,186,922 A | 2/1993 | Shell et al. | 128/654 |
| 5,190,766 A | 3/1993 | Ishihara | 424/489 |
| 5,190,982 A | 3/1993 | Erbel et al. | 521/56 |
| 5,192,549 A | 3/1993 | Barenolz et al. | 424/450 |
| 5,194,266 A | 3/1993 | Abra et al. | 424/450 |
| 5,195,520 A | 3/1993 | Schlief et al. | 128/660.02 |
| 5,196,183 A | 3/1993 | Yudelson et al. | 424/9 |
| 5,196,348 A | 3/1993 | Schweighardt et al. | 436/173 |
| 5,198,225 A | 3/1993 | Meybeck et al. | 424/450 |
| 5,205,287 A | 4/1993 | Erbel et al. | 128/632 |
| 5,205,290 A | 4/1993 | Unger | 128/653.4 |
| 5,209,720 A | 5/1993 | Unger | 604/22 |
| 5,213,804 A | 5/1993 | Martin et al. | 424/450 |
| 5,215,680 A | 6/1993 | D'Arrigo | 252/307 |
| 5,219,538 A | 6/1993 | Henderson et al. | 428/402.2 |
| 5,228,446 A | 7/1993 | Unger et al. | 128/662.02 |
| 5,230,882 A | 7/1993 | Unger | 424/9 |
| 5,247,935 A | 9/1993 | Cline et al. | 128/653.2 |
| 5,271,928 A | 12/1993 | Schneider et al. | 424/9 |
| 5,281,408 A | 1/1994 | Unger | 424/4 |
| 5,305,757 A | 4/1994 | Unger et al. | 128/662.02 |
| 5,310,540 A | 5/1994 | Giddey et al. | 424/9 |
| 5,315,997 A | 5/1994 | Widder et al. | 128/653.3 |
| 5,315,998 A | 5/1994 | Tachibana et al. | 128/660.01 |
| 5,316,771 A | 5/1994 | Barenholz et al. | 424/450 |
| 5,334,381 A | 8/1994 | Unger | 424/9 |
| 5,339,814 A | 8/1994 | Lasker | 128/653.4 |
| 5,344,930 A | 9/1994 | Riess et al. | 544/84 |
| 5,350,571 A | 9/1994 | Kaufman et al. | 424/9 |
| 5,352,435 A | 10/1994 | Unger | 424/9 |
| 5,354,549 A | 10/1994 | Klaveness et al. | 424/3 |
| 5,358,702 A | 10/1994 | Unger | 424/9 |

| | | | |
|---|---|---|---|
| 5,362,477 A | 11/1994 | Moore et al. | 424/9 |
| 5,362,478 A | 11/1994 | Desai et al. | 424/9 |
| 5,380,519 A | 1/1995 | Schneider et al. | 424/9 |
| 5,393,524 A * | 2/1995 | Quay | 424/9 |
| 5,409,688 A | 4/1995 | Quay | 424/9 |
| 5,410,516 A | 4/1995 | Uhlendorf et al. | 367/7 |
| 5,413,774 A | 5/1995 | Schneider et al. | 424/9.51 |
| 5,425,366 A | 6/1995 | Reinhardt et al. | 128/662.02 |
| 5,433,204 A | 7/1995 | Olson | 128/661.08 |
| 5,445,813 A | 8/1995 | Schneider et al. | 424/9.51 |
| 5,456,900 A | 10/1995 | Unger | 424/9.4 |
| 5,460,800 A | 10/1995 | Walters | 424/9.6 |
| 5,469,854 A * | 11/1995 | Unger et al. | 128/662.02 |
| 5,470,582 A | 11/1995 | Supersaxo et al. | 424/489 |
| 5,485,839 A | 1/1996 | Aida et al. | 128/653.1 |
| 5,487,390 A | 1/1996 | Cohen et al. | 128/662.02 |
| 5,496,535 A | 3/1996 | Kirkland | 424/9.37 |
| 5,498,421 A | 3/1996 | Grinstaff et al. | 424/450 |
| 5,501,863 A | 3/1996 | Rössling et al. | 424/489 |
| 5,502,094 A | 3/1996 | Moore et al. | 524/145 |
| 5,508,021 A | 4/1996 | Grinstaff et al. | 424/9.322 |
| 5,512,268 A | 4/1996 | Grinstaff et al. | 424/322 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,536,489 A * | 7/1996 | Lohrmann et al. | 424/9.52 |
| 5,536,490 A | 7/1996 | Klaveness et al. | 424/9.52 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,552,133 A | 9/1996 | Lambert et al. | 424/9.52 |
| 5,552,155 A | 9/1996 | Bailey et al. | 424/450 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A * | 9/1996 | Quay | 424/9.5 |
| 5,558,856 A | 9/1996 | Klaveness et al. | 424/9.37 |
| 5,560,364 A | 10/1996 | Porter | 128/662.02 |
| 5,562,608 A | 10/1996 | Sekins et al. | 604/20 |
| 5,562,893 A | 10/1996 | Lohrmann | 424/9.52 |
| 5,565,215 A | 10/1996 | Gref et al. | 424/501 |
| 5,567,413 A | 10/1996 | Klaveness et al. | 424/9.51 |
| 5,567,414 A | 10/1996 | Schneider et al. | 424/9.52 |
| 5,567,415 A | 10/1996 | Porter | 424/9.52 |
| 5,567,765 A | 10/1996 | Moore et al. | 524/801 |
| 5,569,448 A | 10/1996 | Wong et al. | 424/9.45 |
| 5,569,449 A | 10/1996 | Klaveness et al. | 424/9.51 |
| 5,571,797 A | 11/1996 | Ohno et al. | 514/44 |
| 5,573,751 A | 11/1996 | Quay | 424/9.52 |
| 5,578,292 A | 11/1996 | Schneider et al. | 424/9.51 |
| 5,585,112 A | 12/1996 | Unger et al. | 424/450 |
| 5,593,680 A | 1/1997 | Bara et al. | 424/401 |
| 5,595,723 A | 1/1997 | Quay | 424/9.5 |
| 5,605,673 A | 2/1997 | Schutt et al. | 424/9.51 |
| 5,606,973 A | 3/1997 | Lambert et al. | 128/662.02 |
| 5,612,057 A | 3/1997 | Lanza et al. | 424/450 |
| 5,612,318 A | 3/1997 | Weichselbaum et al. | 514/44 |
| 5,614,169 A | 3/1997 | Klaveness et al. | 424/9.52 |
| 5,620,689 A | 4/1997 | Allen et al. | 424/178.1 |
| 5,626,833 A | 5/1997 | Schutt et al. | 424/9.52 |
| 5,639,443 A | 6/1997 | Schutt et al. | 424/9.52 |
| 5,639,473 A | 6/1997 | Grinstaff et al. | 424/450 |
| 5,643,553 A | 7/1997 | Schneider et al. | 424/9.52 |
| 5,648,095 A | 7/1997 | Illum et al. | 424/489 |
| 5,648,098 A | 7/1997 | Porter | 424/490 |
| 5,672,585 A | 9/1997 | Pierschbacher et al. | 514/11 |
| 5,676,928 A | 10/1997 | Klaveness et al. | 424/9.32 |
| 5,679,459 A | 10/1997 | Riess et al. | 428/402.2 |
| 5,686,060 A | 11/1997 | Schneider et al. | 424/9.52 |
| 5,686,102 A | 11/1997 | Gross et al. | 424/450 |
| 5,695,460 A | 12/1997 | Siegel et al. | 604/21 |
| 5,695,741 A * | 12/1997 | Schutt et al. | 424/9.52 |
| 5,701,899 A | 12/1997 | Porter | 428/662.02 |
| 5,707,352 A | 1/1998 | Sekins et al. | 604/56 |
| 5,707,606 A | 1/1998 | Quay | 424/9.52 |
| 5,707,607 A | 1/1998 | Quay | 424/9.52 |
| 5,711,933 A | 1/1998 | Bichon et al. | 424/9.52 |
| 5,716,597 A | 2/1998 | Lohrmann et al. | 424/9.5 |
| 5,732,707 A | 3/1998 | Widder et al. | 128/661.08 |
| 5,733,527 A | 3/1998 | Schutt | 424/9.52 |
| 5,736,121 A | 4/1998 | Unger et al. | 424/9.4 |
| 5,740,807 A | 4/1998 | Porter | 128/662.02 |
| 5,770,222 A | 6/1998 | Unger et al. | 424/450 |
| 5,804,162 A | 9/1998 | Kabalnov et al. | 424/9.51 |
| 5,840,023 A | 11/1998 | Oraevsky et al. | 600/407 |
| 5,846,517 A | 12/1998 | Unger | 424/9.52 |
| 5,849,727 A | 12/1998 | Porter et al. | 514/156 |
| 5,853,752 A * | 12/1998 | Unger et al. | 424/450 |
| 5,855,865 A | 1/1999 | Lambert et al. | 424/9.52 |
| 5,858,399 A | 1/1999 | Lanza et al. | 424/450 |
| 5,874,062 A | 2/1999 | Unger | 424/9.4 |
| 5,897,851 A | 4/1999 | Quay et al. | 424/9.52 |
| 5,976,501 A | 11/1999 | Jablonski | 424/9.52 |

FOREIGN PATENT DOCUMENTS

| | | |
|---|---|---|
| EP | 0 052 575 | 5/1982 |
| EP | 0 107 559 | 5/1984 |
| EP | 0 077 752 B1 | 3/1986 |
| EP | 0 243 947 | 4/1987 |
| EP | 0 224 934 | 6/1987 |
| EP | 0 231 091 | 8/1987 |
| EP | 0 272 091 | 6/1988 |
| EP | 0 320 433 A2 | 12/1988 |
| EP | 0 324 938 | 7/1989 |
| EP | 0 338 971 | 10/1989 |
| EP | 357163 A1 | 3/1990 |
| EP | 0 359 246 | 3/1990 |
| EP | 0 361 894 | 4/1990 |
| EP | 0 216 730 | 1/1991 |
| EP | 0 467 031 A2 | 5/1991 |
| EP | 441468 A2 | 8/1991 |
| EP | 0 357 164 B1 | 10/1991 |
| EP | 0 458 745 A1 | 11/1991 |
| EP | 0 314 764 B1 | 9/1992 |
| EP | 0 554 213 A1 | 8/1993 |
| EP | 0 586 875 | 3/1994 |
| EP | 0 614 656 A1 | 9/1994 |
| EP | 0 633 030 A1 | 1/1995 |
| EP | 0 727 225 A2 | 8/1996 |
| EP | 0 901 793 A1 | 3/1999 |
| FR | 2 700 952 | 8/1994 |
| GB | 1044680 | 10/1966 |
| GB | 2193095 A | 2/1988 |
| JP | 62 286534 | 12/1987 |
| JP | SHO 63-60943 | 3/1988 |
| WO | WO 80/02365 | 11/1980 |
| WO | WO 82/01642 | 5/1982 |
| WO | WO 85/01161 | 3/1985 |
| WO | WO 85/02772 | 7/1985 |
| WO | WO 86/00238 | 1/1986 |
| WO | WO 86/01103 | 2/1986 |
| WO | WO 89/05040 | 6/1989 |
| WO | WO 90/01952 | 3/1990 |
| WO | WO 90/04384 | 5/1990 |
| WO | WO 90/04943 | 5/1990 |
| WO | WO 91/00086 | 1/1991 |
| WO | WO 91/03267 | 3/1991 |
| WO | WO 91/09629 | 7/1991 |

| | | |
|---|---|---|
| WO | WO 91/12823 | 9/1991 |
| WO | WO 91/15244 | 10/1991 |
| WO | WO 92/05806 | 4/1992 |
| WO | WO 92/10166 | 6/1992 |
| WO | WO 92/15284 | 9/1992 |
| WO | WO 92/17212 | 10/1992 |
| WO | WO 92/17213 | 10/1992 |
| WO | WO 92/17436 | 10/1992 |
| WO | WO 92/17514 | 10/1992 |
| WO | WO 92/21382 | 10/1992 |
| WO | WO 92/22247 | 12/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 84/02909 | 8/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 96/04018 | 2/1996 |
| WO | WO 96/09793 | 4/1996 |
| WO | WO 96/36286 | 11/1996 |
| WO | WO 96/40281 | 12/1996 |
| WO | WO 96/40285 | 12/1996 |
| WO | WO 98/00172 | 1/1998 |
| WO | WO 99/13919 | 3/1999 |

OTHER PUBLICATIONS

Grob, U., et al., "Phospholipid vesiculated fluorcarbons—promising trend in blood substitutes," *Biomat., Art. Cells & Immob. Biotech.*, 1992, 20 (2–4), 831–833.

Porter, T.R., et al., "Multifold sonicated dilutions of albumin with fifty percent dextrose improve left ventricular contrast videointensity after intravenous injuction in human beings," *J. Am. Soc. Echocardiogr*, XP 000590864, Sep./Oct. 1994, 7(5), 465–471.

Porter, T.R., et al., "Noninvasive identification of acute myocardinal ischemia and reperfusion with contrast ultrasound using intravenous perfluorpropane–exposed sonicated dextrose albumin," *Am. College of Cardiology*, XP 000590865, Jul. 1995, 26(1), 33–40.

Porter, T.R., et al., "Visually discernible myocardial echocardiographic contrast after intravenous injection of sonicated dextrose albumin microbubbles containing high molecular weight, less soluble gases," *Am. College of Cardiology*, Feb. 1995, 25(2), 509–515.

Riess, J.G., "Fluorine in our arteries," *New J.Chem.*, XP–000990897, 1995, 19, 891–909 (English abstract).

Riess, J.G., "Introducing a new element—fluorine—into the liposomal membrane," *J. Liposome Research*, 1995, 5(3), 413–430.

Santaella, C., et al., "Extended in vivo blood circulation time of fluorinated liposomes," *FEBS 13463*, XP–000990861, Dec. 1993, 336(3), 481–484.

Srinivasan, S.K., et al., "Characterization of binding sites, extent of binding, and drug interactions of oligonucleotides with albumin," *Antisense Res. And Develop.*, 1995, 5, 131–139.

Trevino, L., et al., "Incorporation of a perfluoroalkylalkane ($R_FR_H$) into the phospholipid bilayer of DMPC liposomes results in greater encapsulation stability," XP 000457303, Jul. 4, 1994, 4(2), 1017–1028.

Xie, F., et al., "Acute myocardial ischemia and reperfusion can be visually identified non–invasively with intravenous perfluoropropane–enhanced sonicated dextrose albumin ultrasound contrast," *Circulation*, Oct. 1994, 90(4), Part 2, Abstract 2989, 1 page.

Zarif, L., et al., "Biodistribution and excretion of a mixed fluorocarbon–hydrocarbon "dowel" emulsion as determined by $^{19}$F NMR," *Art. Cells, Blood Subs., and Immob. Biotech.*, 1994, 22(4), 1193–1198.

Reexamination of U.S. Patent No. 5,527,521, Reexam Control No. 90/004,719.

Reexamination of U.S. Patent No. 5,547,656, Reexam Control No. 90/004,720.

Hautanen, A., et al., "Effects of modifications of the RGD sequence and its context on recognition by the fibronectin receptor," *J. Biol. Chem.*, 1989, 264(3), 1437–1442.

Porter, T. R., et al., "Thrombolytic Enhancement with Perfluorocarbon–exposed Sonicated Dextrose Albumin Microbubbles", *American Heart Journal*, Nov. 1996, vol. 132, No. 5, pp. 964–968.

Takeuchi, M., et al., "Enhanced visualization of intravascular thrombus with the use of a thrombus targeting ultrasound contrast agent (MRX408): Evidence from in vivo experimental echocardiographic studies," *J. Am. College of Cardiology*, 1998, 81(12), 1 page, Abstract XP–000952675.

Unger, E.C., et al., "In vitrostudies of a new thrombus–specific ultrasound contrast agent," *J. of Cardiology*, 1998, 81(12), 58G–61G, Abstract XP–002087505.

Wu, Y., et al., "Binding and lysing of blood clots using MRX–408," *Investigate Radiology*, 1998, 33(12), 880–885.

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Chortkoff, B.S. et al., "Pharmacokinetics Do Not Explain the Absence of an Anesthetic Effect of Perfluoropropane or Perfluoropentane," *Anesth. Analg.*, 1994, 79, 234–237.

Sharma, S.K. et al., "Emulsification Methods For Perfluorochemicals," *Drug Develop. Indust. Pharm.*, 1988, 14(15–17), 2371–2376.

Tilcock, C. et al., "PEG–coated Lipid Vesicles with Encapsulated Technetium–99m as Blood Pool Agents for Nuclear Medicine," *Nucl. Med. Biol.*, 1994, 21(2),. 165–170.

Tilcock, C. et al., "$^{99m}$Tc–labeling of Lipid Vesicles Containing and Lipophilic Chelator PE–DTTA: Effect of Tin–to–chelate Ratio, Chelate Content and Surface Polymer of Labeling Efficiency and Biodistribution Behavior," *Nucl. Med. Biol.*, 1994, 21(1), 89–96.

Zarif, L. et al., "Synergistic Stabilization of Perfluorocarbon– Pluronic F–68 Emulsion by Perfluoroalkylated Polyhydroxylated Surfactants," *JAOCS*, 1989, 66(10), 1515–1523.

Ding, X.C., "Scavenging effect of EDTA–fluorocarbon microspheres on 210 lead," *Chung Kuto Yao Li Hsueh Pao*, 1989, 10(5), 473–475 (abstract only).

Kinsler, L. E., et al., *Fundamentals of Acoustics*, 3$^{rd}$ Ed., John Wiley & Sons, 1982, 228–331.

Meessen, H. (ed.), *Microcirculation*, Springer–Verlag, Berlin Heidelberg, New York, 1997, 44.

Ring, J., et al., "Humanalbuminunverträglichkeit: Klinische Und Immunologische Untersuchungen," *Clinical Weekly*, 1974, 52, 595–598.

Robinson, et al., F.J. Fry (ed.), "Ultrasound: Its Applications In Medicine And Biology," *Elsevier Scientific Publishing Company*, 1978, vol. 3, Chap. XI, 593–596.

Silbernagl, S., et al., "Pocket Atlas Of Physiology," *Georg Thieme Verlag*, Stuttgart, New York, 1983, 156–157.

Wells, P.N.T., "Pulse–Echo Methods," *Biomedical Ultrasonics*, Academic Press, 1977, 209–220.

Lejbkowicz et al., "The response of normal and malignant cells to ultrasound in vitro", Database *BIOSIS*, No. 1993:95122245 (abstract only).

Jackson et al., "Effect of ultrasound therapy on the repair of Achilles tendon injuries in rats", *Med. Sci. Sports Exercise*, 1991, 23(2), 171–176.

Maxwell, "Therapeutic Ultrasound: Its Effects of the Cellular and Molecular Mechanisms of Inflammation and Repair", *Physiotherapy*, 1992, 78(6), 421–426.

Tuncay et al., "Expression of Genes Associated with Tissue Remodeling Upon Ultrasound Perturbation in the Gingival Fibroblast", *J. Dental Res.*, 1996, 75, 143, (abstract only).

Wang et al., "Low Intensity Ultrasound Treatment Increases Strength in a Rat Femoral Fracture Model", *J. Orthopaedic Res.*, 1994, 12(1), 40–47.

Yang et al., "Exposure to Low–Intensity Ultrasound Increases Aggrecan Gene Expression in a Rat Femur Facture Model", *J. Orthopaedic Res.*, 1996, 14(5), 802–809.

Young et al., "Effect of therapeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–18 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988., Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol.* (MOSC), vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 30–35, 51–65 and 79–107 (CRC Press Inc., Boca Raton, FL, (1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiably Low–frequency Synthesized Ultrasound", *IEEE Engineering*, pp. 879–880, vol. 2 (1988) (abstract).

McAvoy et al., *IEEE Engineering, Ultrasonics Symposium Proceedings*, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Kost et al., *Polymers in Medicine II: Biomedical and Pharmaceutical Applications*, "Ultrasonic Modulated Drug Delivery Systems", Chiellini et al., ed., (Plenum Press, New York and London), pp. 387–396 (1985).

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

MacDonald, *Mammalian Cell Biotechnology: A Practical Approach*, M. Butler, ed., 1991 (Oxford University Press, New York), pp. 57–70.

Mathiowitz et al., "Photochemical Rupture of Microcapsules: A Model System", *Journal of Applied Polymer Science*, 1981, 27:809–822.

May et al., "Cationic Liposomes Enable Bovine Herpesvirus Type 2 DNA to Infect Cells", *Acta virol.*, 1991, 35:107.

Poznansky et al., "Biological Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", *Biochimica et Biophysica Acta* 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbiology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", Proc. Natl. Acad. Sci., vol. 88, pp. 8686–8690 (1991).

Scientific Apparatus Catalog 92/93 (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., Radiology, "Detection of Intracardiac Blood Flow by Pulsed Echo–Ranging", pp. 415–418 (1971).

Feigenbaum et al., Circulation, "Identification of Ultrasound Echoes from the Left Ventricle by Use of Intracardiac Injections of Indocyanine Green", vol. XL1, pp. 615–631 (1970).

Santaella, et al., FEBS 13463, "Extended In Vivo Blood Circulation Time of Fluorinated Liposomes", vol. 336, No. 3, pp. 481–484 (1993).

Brown and Langer, Annual Review Medicine, 1988, 39:221 29, Annual Review, Inc., "Transdermal Delivery of Drugs", pp. 221–229.

Moseley, et al., Microbubbles: A Novel MR Susceptibility Contrast Agent, abstract, 1991 Napa, California Meeting of the Society for Magentic Resonance in Medicine.

Ter–Pogossian Tomography, Kee, et al., n, "Physical Principles and Instrumentation", Computed Body eds., Raven Press, New York, Chapter 1, pp. 1–7 (1988).

Aronberg, "Techniques", Computed Body Tomography, Kee, et al., eds., Raven Press, New York, Chapter 2, pp. 9–36 (1988).

Miller, Ultrasonics (Sep. 1981), "Ultrasonic detection of resonant cavitation bubbles in a flow tube by their second–harmonic emissions," pp. 217–224.

Dittrich, "Cardiac Muscle Ischemia and Infarction", The Second Annual International Symposium on Contrast Agents in Diagnostic Ultrasound, Atlantic City, NJ (May 7, 1996) (abstract).

Pantely, "Intravenous Contrast Echocardiography–Tissue Imaging & Quantification of Coronary Blood Flow", The Second Annual International Symposium on Contrast Agents in Diagnostic Ultrasound, Atlantic City, NJ (May 7, 1996) (abstract).

Schutt et al., "Osmotically Stabilized Microbubble Sonographic Contrast Agents", Acad. Radiol., vol. 3, Suppl. 2, pp. S188–S190 (Aug. 1996).

Frézard, et al., "Permeability and stability in buffer and in human serum of fluorinated phospholipid–based liposomes", Biochimica et Biophysica Acta, 1192, pp. 61–70 (1994).

Frézard, et al., "Fluorinated Phospholipid–Based Vesicles as Potential Drug Carriers: Encapsulation/Sustaining of Drugs and Stability in Human Serum", Art, Cells, Blood Subs., and Immob. Biotech., 22(4), pp. 1403–1408 (1994).

Chang et al., "Semipermeable Aqueous Microcapsules", Canadian J. Of Phys. And Pharm., 1966, 44, 115–128.

Chang, "Semipermeable Microcapsules", Science, 1964, 146, 524–525.

Deasy, Microencapsulation and Related Drug Processes, 1983, vol. 20, Chs. 9 and 10, 195–240 (Marcel Dekker, Inc., NY).

Yeung et al., "Preparation of Microencapsulated Liposomes", J. Microencapsulation, 1988, 5, 331–337.

Mattrey et al., Gas Emulsions as Ultrasound Contrast Agents; Preliminary Results in Rabbits and Dogs, Investigative Radiology, vol. 29, Jun. Supp. 2, pp. S139–S141, 1994.

Meltzer et al., Transmission of Ultrasonic Contrast Through the Lungs, Ultrasound in Med. & Biol., vol. 7, No. 4, 377–384, 1981.

PR Newswire, Apr. 1, 1986.

Swanson et al., Chapter 22, "Enhancement Agents for Ultrasound: Fundamentals", Pharmaceuticals In Medical Imaging, pp. 682–687 (1990).

Ophir et al., "Contrast Agents in Diagnostic Ultrasound", Ultrasound in Med. & Biol., vol. 15, No. 4, pp. 319–333 (1989).

Jacobs, "Intraocular gas measurement using A–scan ultrasound", Current Eye Research, vol. 5, No. 8, pp. 575–578 (1986).

Lincoff et al., "Intravitreal Expansion of Perfluorocarbon Bubbles", Arch. Ophthalmol., vol. 98, p. 1646, Sep. 1980.

Lincoff et al., "Intravitreal Longevity of Three Perfluorocarbon Gases", Arch. Ophthalmol., vol. 98, pp. 1610–1611, Sep. 1980.

Lincoff et al., "The Perfluorocarbon Gases in the Treatment of Retinal Detachment", Ophthalmology, vol. 90, No. 5, pp. 546–551, May 1983.

Gardner et al., "A Survey of Intraocular Gas Use in North America", Arch. Ophthalmol., vol. 106, pp. 1188–1189, Sep. 1988.

Unger et al., "Liposomal MR Contrast Agents", J. Liposome Research, 4(2), pp. 811–834 (1994).

Feinstein, Steven B., "Myocardial Perfusion Imaging: Contrast Echocardiography Today and Tomorrow," Journal of the American College of Cardiology, 8(1):251–253 (1986).

Keller et al., "The Behavior of Sonicated Albumin Microbubbles Within the Microcirculation: A Basis for Their Use During Myocardial Contrast Echocardiography", Circulation Res., 65(2):458–465 (1989).

Lincoff et al., "Perfluoro–n–butane: A Gas for Maximum Duration Retinal Tamponade," Arch Ophthalmology, 101:460–462 (1983).

Remington's Pharmaceutical Sciences, John Hoover, managing ed., Mack Publishing Company, Easton, PA, pp. 295–298; 736; 1242–1244 (1975).

Handbook of Pharmaceutical Excipients, American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," Investigative Radiology, 25:S162–164 (1990).

Levene et al., "Characerization of Albunex™," J. Acoust. Soc. Am., 87(Suppl.1):569–70 (1990).

Miller et al., "Physiochemical Approaches to the Mode of Action of General Anesthetics," J. Amer. Soc. Anesthesiologists, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Desir et al., "Assessment of regional myocardial perfusion with myocardial contrast echocardiography in a canine model of varying degrees of coronary stenosis", *American Heart Journal*, vol. 127, No. 1, pp. 56–63 (Jan. 1994).

Sekins et al., "Lung Cancer Hyperthermia via Ultrasound and PFC Liquids", *Published in Proceedings of 5th International Symposium on Hyperthermic Oncology*, Kyoto, Japan, (3 pages) (Aug. 29–Sep. 3, 1998).

Pietersen, "A New Warning System for Fires of Electrical Origin", *CERN European Organization for Nuclear Research, Health and Safety Division*, pp. 1–5 (Mar. 1977).

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

Regen, S.L. et al., "Polymerized Phosphatidylcholine Vesicles. Synthesis and Characterization", *J. Am. Chem. Soc.*, 1982, 104(3), 791–795.

\* cited by examiner

METHOD OF PREPARING GAS AND GASEOUS PRECURSOR-FILLED MICROSPHERES

RELATED APPLICATIONS

This Application is a divisional of application Ser. No. 08/487,230 filed Jun. 6, 1995 now U.S. Pat. No. 5,853,752, which is a divisional filing of U.S. Ser. No. 08/159,687 filed Nov. 30, 1993, which is a Continuation-in-Part of U.S. Ser. No. 08/160,232 filed Nov. 30, 1993, now U.S. Pat. No. 5,542,935, and U.S. Ser. No. 08/159,674 filed Nov. 30, 1993, now abandoned, both of which are Continuations-in-Part of Ser. No. 08/076,239 filed Jun. 11, 1993, now U.S. Pat. No. 5,469,854, which is a Continuation-in-Part of both U.S. Ser. No. 07/717,084 filed Jun. 18, 1991, now U.S. Pat. No. 5,228,446, and U.S. Ser. No. 07/716,899 filed Jun. 18, 1991, now abandoned, both of which are Continuations-in-Part of U.S. Ser. No. 07/569,828 filed Aug. 20, 1990, now U.S. Pat. No. 5,088,499, which is a Continuation-in-Part of Ser. No. 07/455,707 filed Dec. 22, 1989, now abandoned.

BACKGROUND OF THE INVENTION

1. Field of the Invention

This invention relates to novel methods and apparatus for preparing gaseous precursor-filled liposomes. Liposomes prepared by these methods are particularly useful, for example, in ultrasonic imaging applications and in therapeutic delivery systems.

2. Background of the Invention

A variety of imaging techniques have been used to detect and diagnose disease in animals and humans. X-rays represent one of the first techniques used for diagnostic imaging. The images obtained through this technique reflect the electron density of the object being imaged. Contrast agents such as barium or iodine have been used over the years to attenuate or block X-rays such that the contrast between various structures is increased. X-rays, however, are known to be somewhat dangerous, since the radiation employed in X-rays is ionizing, and the various deleterious effects of ionizing radiation are cumulative.

Another important imaging technique is magnetic resonance imaging (MRI). This technique, however, has various drawbacks such as expense and the fact that it cannot be conducted as a portable examination. In addition, MRI is not available at many medical centers.

Radionuclides, employed in nuclear medicine, provide a further imaging technique. In employing this technique, radionuclides such as technetium labelled compounds are injected into the patient, and images are obtained from gamma cameras. Nuclear medicine techniques, however, suffer from poor spatial resolution and expose the animal or patient to the deleterious effects of radiation. Furthermore, the handling and disposal of radionuclides is problematic.

Ultrasound is another diagnostic imaging technique which is unlike nuclear medicine and X-rays since it does not expose the patient to the harmful effects of ionizing radiation. Moreover, unlike magnetic resonance imaging, ultrasound is relatively inexpensive and can be conducted as a portable examination. In using the ultrasound technique, sound is transmitted into a patient or animal via a transducer. When the sound waves propagate through the body, they encounter interfaces from tissues and fluids. Depending on the acoustic properties of the tissues and fluids in the body, the ultrasound sound waves are partially or wholly reflected or absorbed. When sound waves are reflected by an interface they are detected by the receiver in the transducer and processed to form an image. The acoustic properties of the tissues and fluids within the body determine the contrast which appears in the resultant image.

Advances have been made in recent years in ultrasound technology. However, despite these various technological improvements, ultrasound is still an imperfect tool in a number of respects, particularly with regard to the imaging and detection of disease in the liver and spleen, kidneys, heart and vasculature, including measuring blood flow. The ability to detect and measure these regions depends on the difference in acoustic properties between tissues or fluids and the surrounding tissues or fluids. As a result, contrast agents have been sought which will increase the acoustic difference between tissues or fluids and the surrounding tissues or fluids in order to improve ultrasonic imaging and disease detection.

The principles underlying image formation in ultrasound have directed researchers to the pursuit of gaseous contrast agents. Changes in acoustic properties or acoustic impedance are most pronounced at interfaces of different substances with greatly differing density or acoustic impedance, particularly at the interface between solids, liquids and gases. When ultrasound sound waves encounter such interfaces, the changes in acoustic impedance result in a more intense reflection of sound waves and a more intense signal in the ultrasound image. An additional factor affecting the efficiency or reflection of sound is the elasticity of the reflecting interface. The greater the elasticity of this interface, the more efficient the reflection of sound. Substances such as gas bubbles present highly elastic interfaces. Thus, as a result of the foregoing principles, researchers have focused on the development of ultrasound contrast agents based on gas bubbles or gas containing bodies and on the development of efficient methods for their preparation.

Ryan et al., in U.S. Pat. No. 4,544,545, disclose phospholipid liposomes having a chemically modified cholesterol coating. The cholesterol coating may be a monolayer or bilayer. An aqueous medium, containing a tracer, therapeutic, or cytotoxic agent, is confined within the liposome. Liposomes, having a diameter of 0.001 microns to 10 microns, are prepared by agitation and ultrasonic vibration.

D'Arrigo, in U.S. Pat. Nos. 4,684,479 and 5,215,680, teaches a gas-in-liquid emulsion and method for the production thereof from surfactant mixtures. U.S. Pat. No. 4,684,479 discloses the production of liposomes by shaking a solution of the surfactant in a liquid medium in air. U.S. Pat. No. 5,215,680 is directed to a large scale method of producing lipid coated microbubbles including shaking a solution of the surfactant in liquid medium in air or other gaseous mixture and filter sterilizing the resultant solution.

WO 80/02365 discloses the production of microbubbles having an inert gas, such as nitrogen; or carbon dioxide, encapsulated in a gellable membrane. The liposomes may be stored at low temperatures and warmed prior and during use in humans. WO 82/01642 describes microbubble precursors and methods for their production. The microbubbles are formed in a liquid by dissolving a solid material. Gas-filled voids result, wherein the gas is 1.) produced from gas present in voids between the microparticles of solid precursor aggregates, 2.) absorbed on the surfaces of particles of the precursor, 3.) an integral part of the internal structure of particles of the precursor, 4.) formed when the precursor reacts chemically with the liquid, and 5.) dissolved in the liquid and released when the precursor is dissolved therein.

In addition, Feinstein, in U.S. Pat. Nos. 4,718,433 and 4,774,958, teaches the use of albumin coated microbubbles for the purposes of ultrasound.

Widder, in U.S. Pat. Nos. 4,572,203 and 4,844,882, discloses a method of ultrasonic imaging and a microbubble-type ultrasonic imaging agent.

Quay, in WO 93/05819, describes the use of agents to form microbubbles comprising especially selected gases based upon a criteria of known physical constants, including 1) size of the bubble, 2) density of the gas, 3) solubility of the gas in the surrounding medium, and 4) diffusivity of the gas into the medium.

Kaufman et al., in U.S. Pat. No. 5,171,755, disclose an emulsion comprising an highly fluorinated organic compound, an oil having no substantial surface activity or water solubility and a surfactant. Kaufman et al. also teach a method of using the emulsion in medical applications.

Another area of significant research effort is in the area of targeted drug delivery. Targeted delivery means are particularly important where toxicity is an issue. Specific therapeutic delivery methods potentially serve to minimize toxic side effects, lower the required dosage amounts, and decrease costs for the patient.

The methods and materials in the prior art for introduction of genetic materials, for example, to living cells is limited and ineffective. To date several different mechanisms have been developed to deliver genetic material to living cells. These mechanisms include techniques such as calcium phosphate precipitation and electroporation, and carriers such as cationic polymers and aqueous-filled liposomes. These methods have all been relatively ineffective in vivo and only of limited use for cell culture transfection. None of these methods potentiate local release, delivery and integration of genetic material to the target cell.

Better means of delivery for therapeutics such as genetic materials are needed to treat a wide variety of human and animal diseases. Great strides have been made in characterizing genetic diseases and in understanding protein transcription but relatively little progress has been made in delivering genetic material to cells for treatment of human and animal disease.

A principal difficulty has been to deliver the genetic material from the extracellular space to the intracellular space or even to effectively localize genetic material at the surface of selected cell membranes. A variety of techniques have been tried in vivo but without great success. For example, viruses such as adenoviruses and retroviruses have been used as vectors to transfer genetic material to cells. Whole virus has been used but the amount of genetic material that can be placed inside of the viral capsule is limited and there is concern about possible dangerous interactions that might be caused by live virus. The essential components of the viral capsule may be isolated and used to carry genetic material to selected cells. In vivo, however, not only must the delivery vehicle recognize certain cells but it also must be delivered to these cells. Despite extensive work on viral vectors, it has been difficult to develop a successfully targeted viral mediated vector for delivery of genetic material in vivo.

Conventional, liquid-containing liposomes have been used to deliver genetic material to cells in cell culture but have mainly been ineffective in vivo for cellular delivery of genetic material. For example, cationic liposome transfection techniques have not worked effectively in vivo. More effective means are needed to improve the cellular delivery of therapeutics such as genetic material.

The present invention is directed to addressing the foregoing, as well as other important needs in the area of contrast agents for ultrasonic imaging and vehicles for the effective targeted delivery of therapeutics.

SUMMARY OF THE INVENTION

The present invention provides methods and apparatus for preparing temperature activated gaseous precursor-filled liposomes suitable for use as contrast agents for ultrasonic imaging or as drug delivery agents. The methods of the present invention provide the advantages, for example, of simplicity and potential cost savings during manufacturing of temperature activated gaseous precursor-filled liposomes.

Preferred methods for preparing the temperature activated gaseous precursor-filled liposomes comprise shaking an aqueous solution comprising a lipid in the presence of a temperature activated gaseous precursor, at a temperature below the gel state to liquid crystalline state phase transition temperature of the lipid.

Unexpectedly, the temperature activated gaseous precursor-filled liposomes prepared in accordance with the methods of the present invention possess a number of surprising yet highly beneficial characteristics. For example, gaseous precursor-filled liposomes are advantageous due to their biocompatibility and the ease with which lipophilic compounds can be made to cross cell membranes after the liposomes are ruptured. The liposomes of the invention also exhibit intense echogenicity on ultrasound, are highly stable to pressure, and/or generally possess a long storage life, either when stored dry or suspended in a liquid medium. The echogenicity of the liposomes is of importance to the diagnostic and therapeutic applications of the liposomes made according to the invention. The gaseous precursor-filled liposomes also have the advantages, for example, of stable particle size, low toxicity and compliant membranes. It is believed that the flexible membranes of the gaseous precursor-filled liposomes may be useful in aiding the accumulation or targeting of these liposomes to tissues such as tumors.

The temperature activated gaseous precursor-filled liposomes made according to the present invention thus have superior characteristics for ultrasound contrast imaging. When inside an aqueous or tissue media, the gaseous precursor-filled liposome creates an interface for the enhanced absorption of sound. The gaseous precursor-filled liposomes are therefore useful in imaging a patient generally, and/or in diagnosing the presence of diseased tissue in a patient as well as in tissue heating and the facilitation of drug release or activation.

In addition to ultrasound, the temperature activated gaseous precursor-filled liposomes made according to the present invention may be used, for example, for magnetic imaging and as NRI contrast agents. For example, the gaseous precursor-filled liposomes may contain paramagnetic gases, such as atmospheric air, which contains traces of oxygen 17; paramagnetic ions such as $Mn^{+2}$, $Gd^{+2}$, $Fe^{+3}$; iron oxides; or magnetite ($Fe_3O_4$) and may thus be used as susceptibility contrast agents for magnetic resonance imaging. Additionally, for example, the gaseous precursor-filled liposomes made according to the present invention may contain radioopaque metal ions, such as iodine, barium, bromine, or tungsten, for use as x-ray contrast agents.

The temperature activated gaseous precursor-filled liposomes are also particularly useful as drug carriers. Unlike liposomes of the prior art that have a liquid interior suitable only for encapsulating drugs that are water soluble, the gaseous precursor-filled liposomes made according to the present invention are particularly useful for encapsulating lipophilic drugs. Furthermore, lipophilic derivatives of drugs may be incorporated into the lipid layer readily, such as alkylated derivatives of metallocene dihalides. Kuo et al., *J. Am. Chem. Soc.* 1991, 113, 9027–9045.

BRIEF DESCRIPTION OF THE FIGS.

Figure 6A:
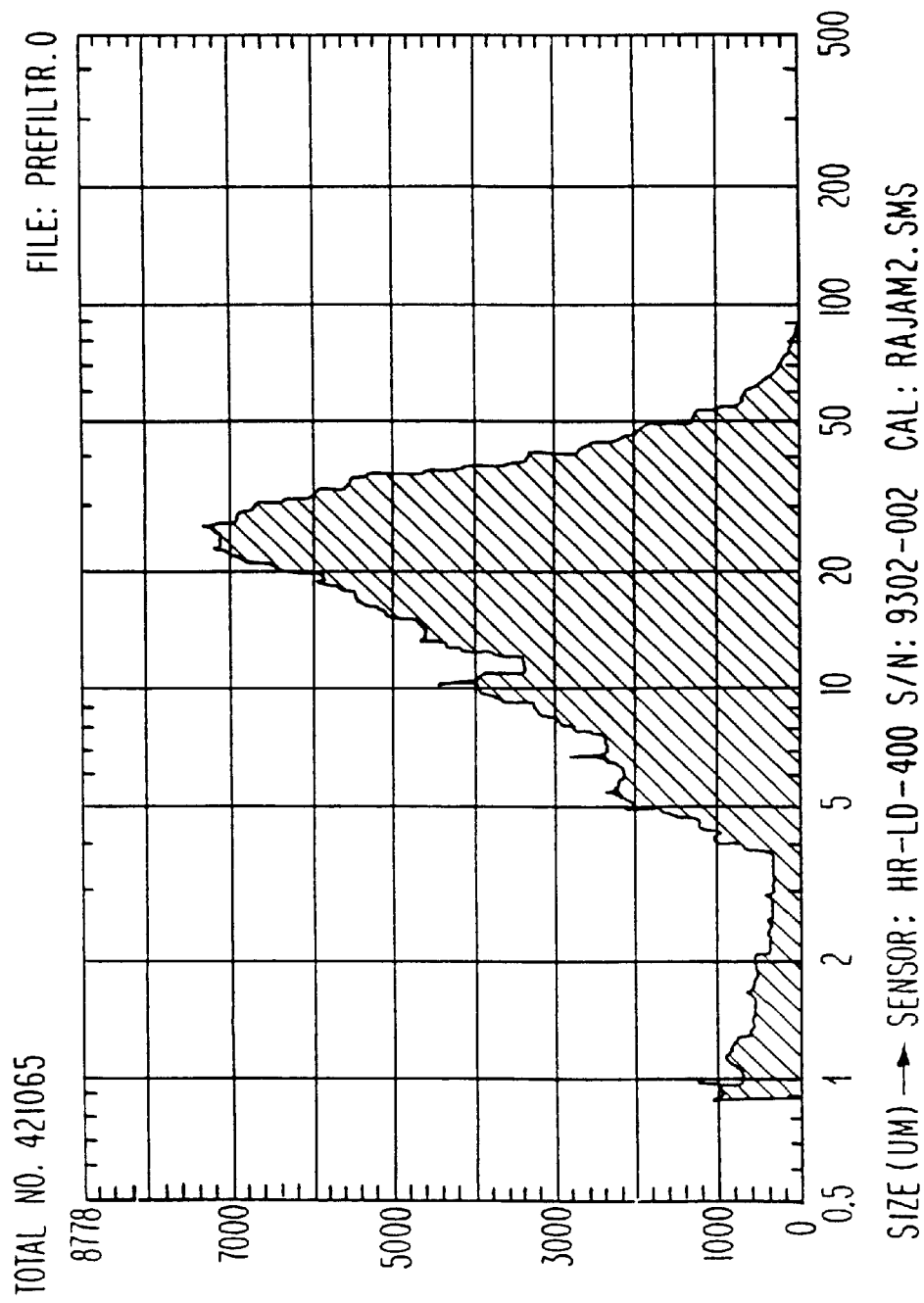
Figure 6B:
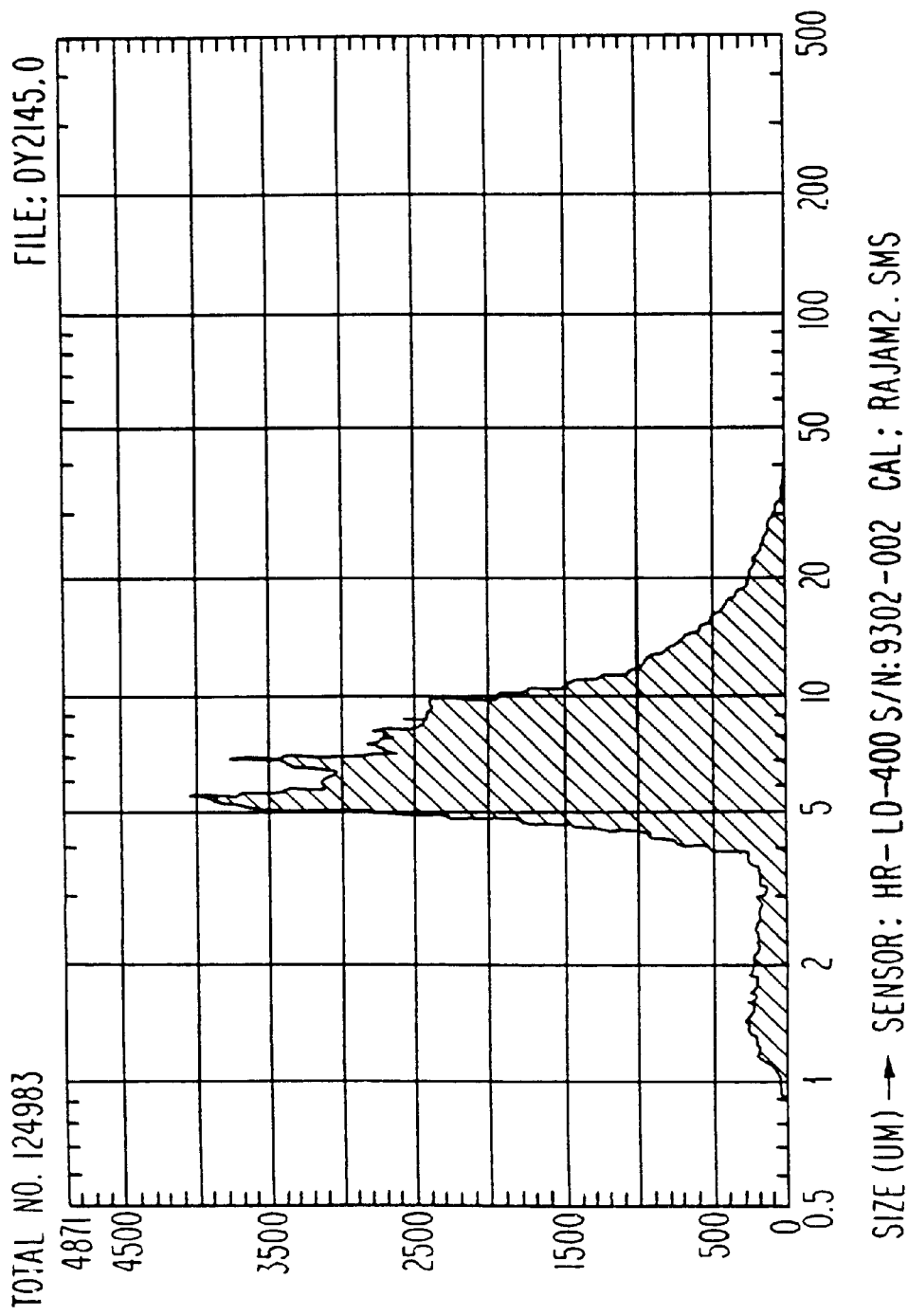

FIGS. 6A and 6B graphically depicts the size distribution of gaseous precursor-filled liposomes of the invention before (A) and after (B) filtration.

Figure 7A:
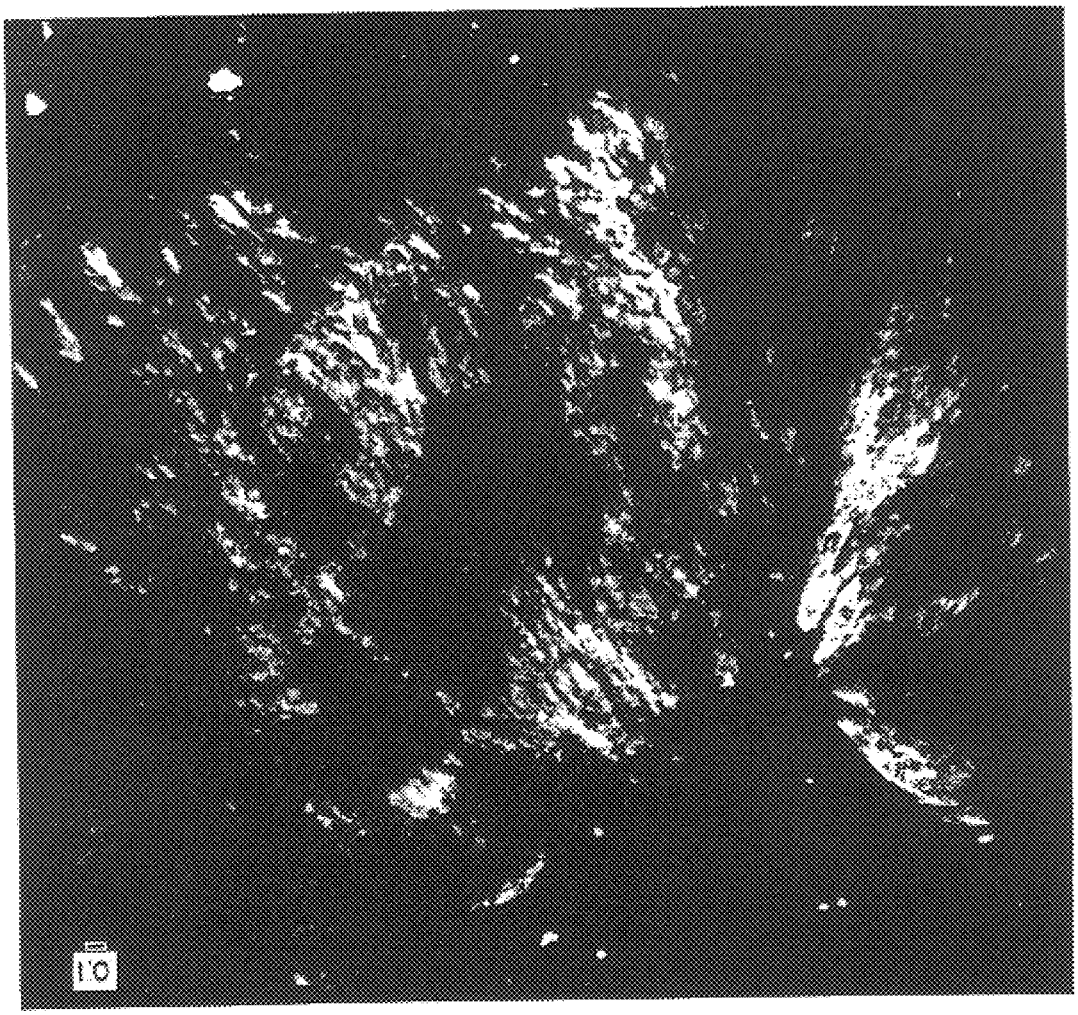
Figure 7B:
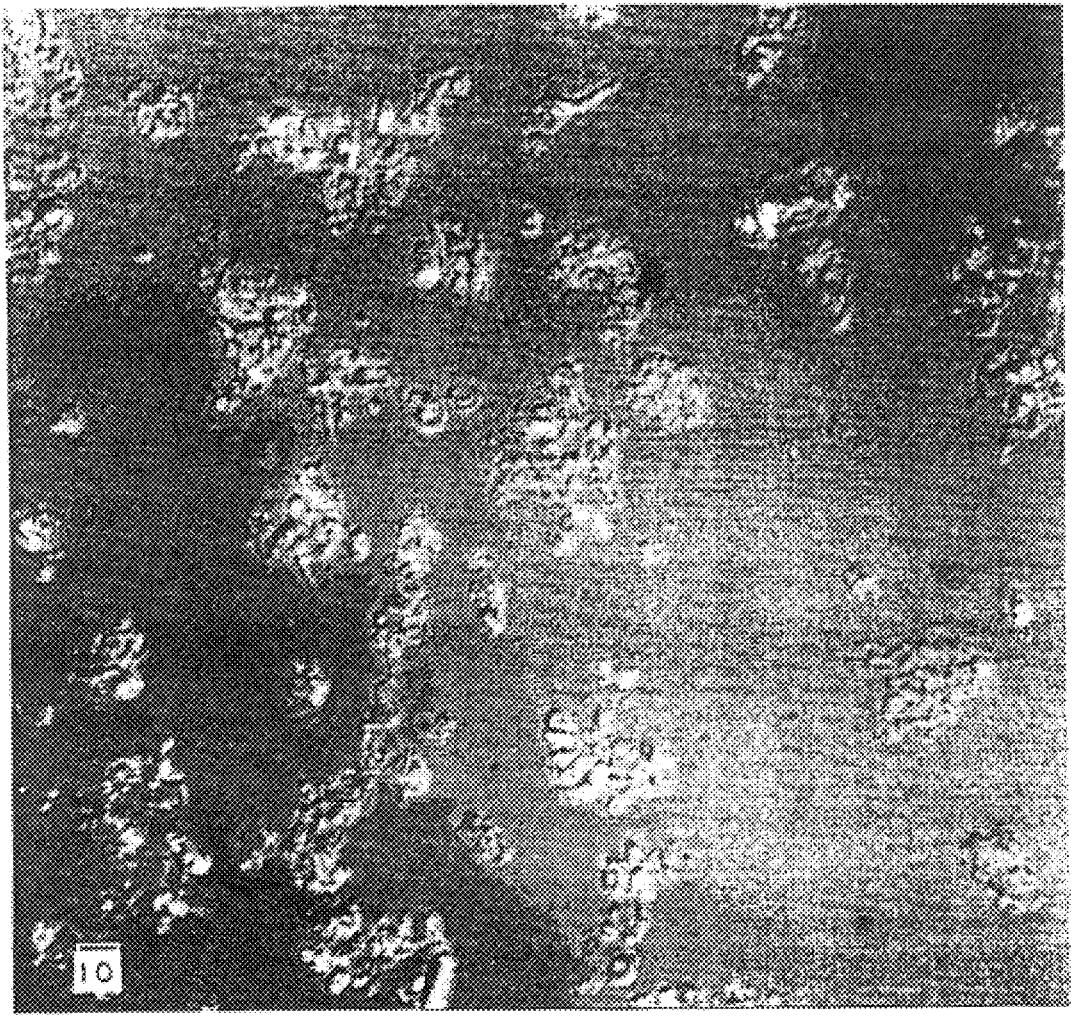

FIGS. 7A and 7B is a micrograph of a lipid suspension before (A) and after (B) extrusion through a filter (Scale bar is 10 $\mu$M).

Figure 8A:
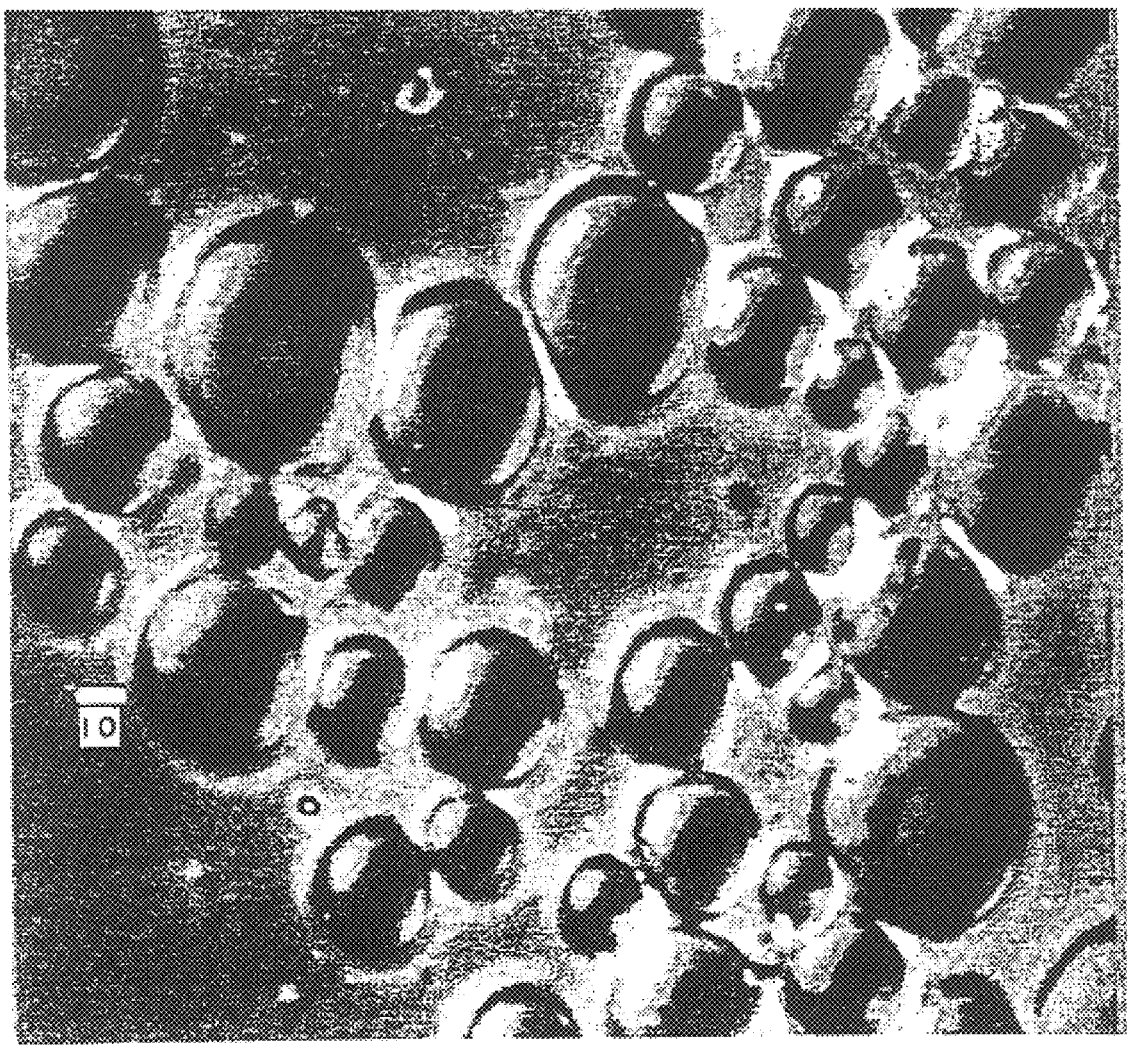
Figure 8B:
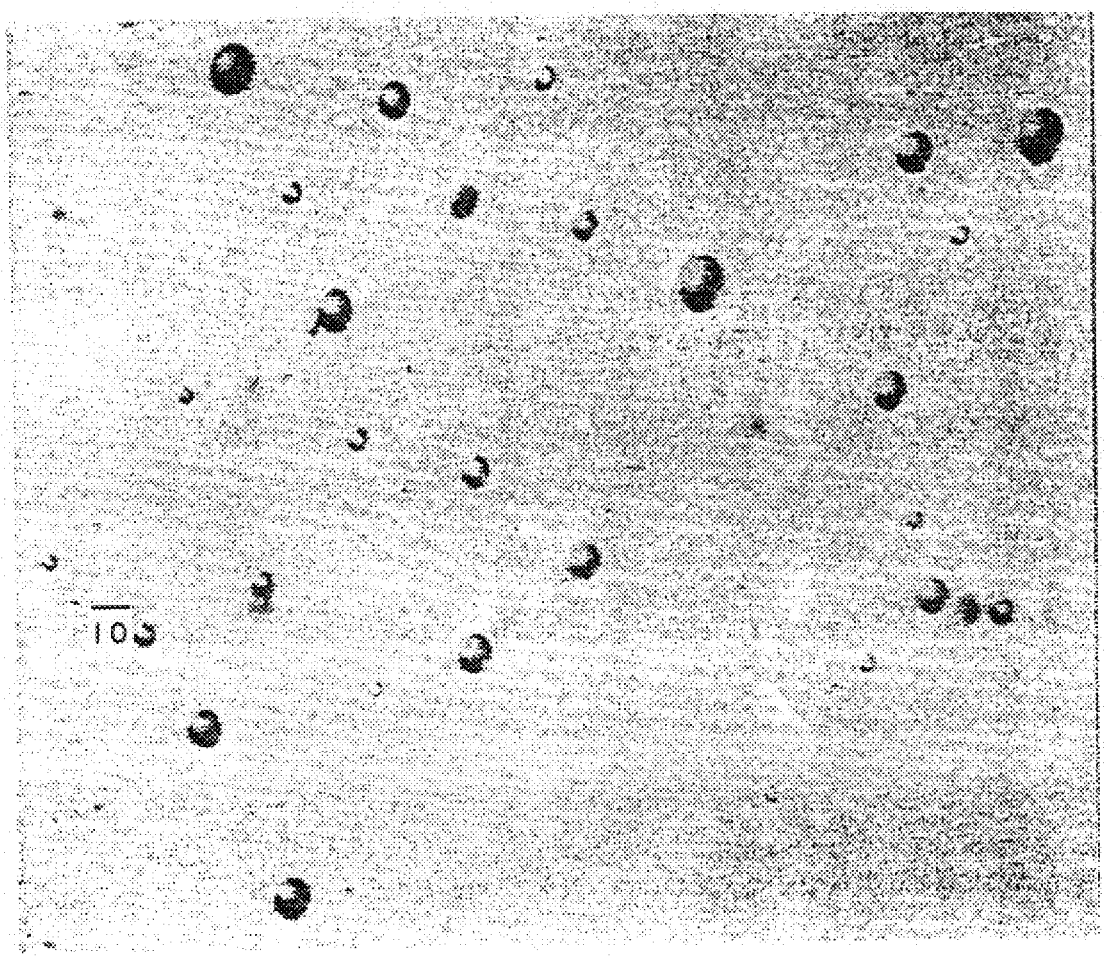

FIGS. 8A and 8B is a micrograph of gaseous precursor-filled liposomes formed subsequent to filtering and autoclaving a lipid suspension, the micrographs having been taken before (A) and after (B) sizing by filtration of the gaseous precursor-filled liposomes.

Figure 9:
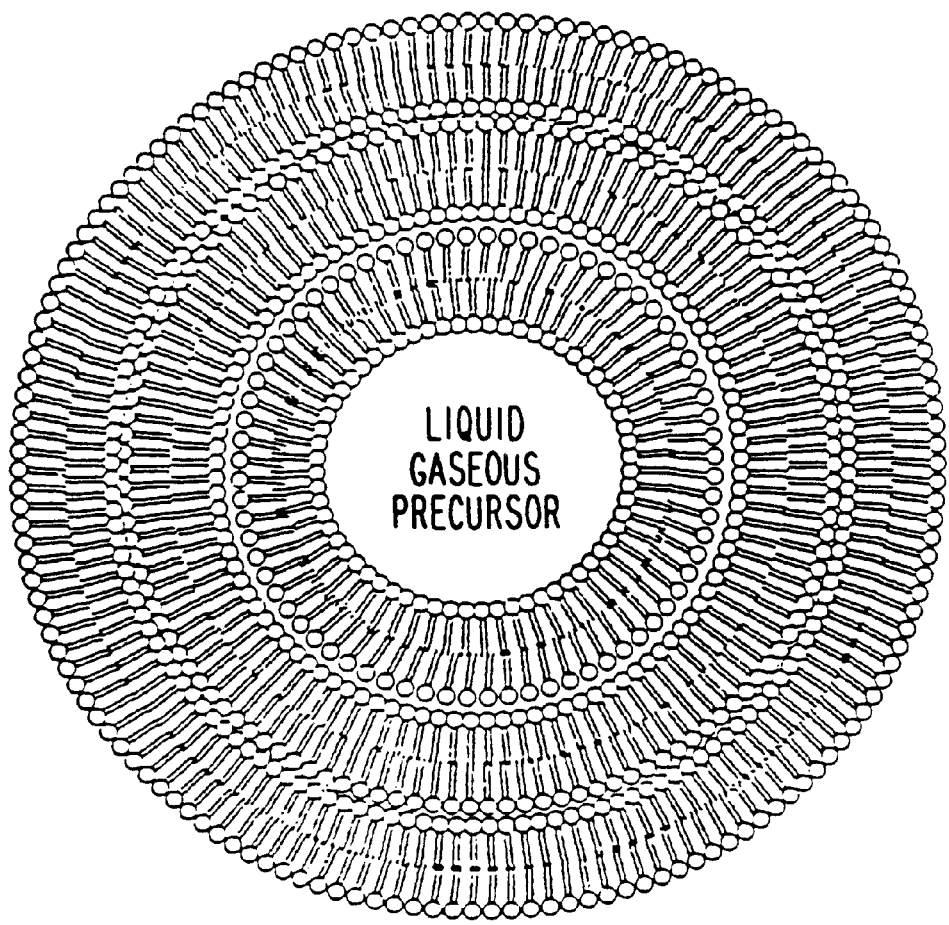

FIG. 9 is a diagrammatic illustration of a temperature activated gaseous precursor-filled liposome prior to temperature activation. The liposome has a multilamellar membrane.

Figure 10:
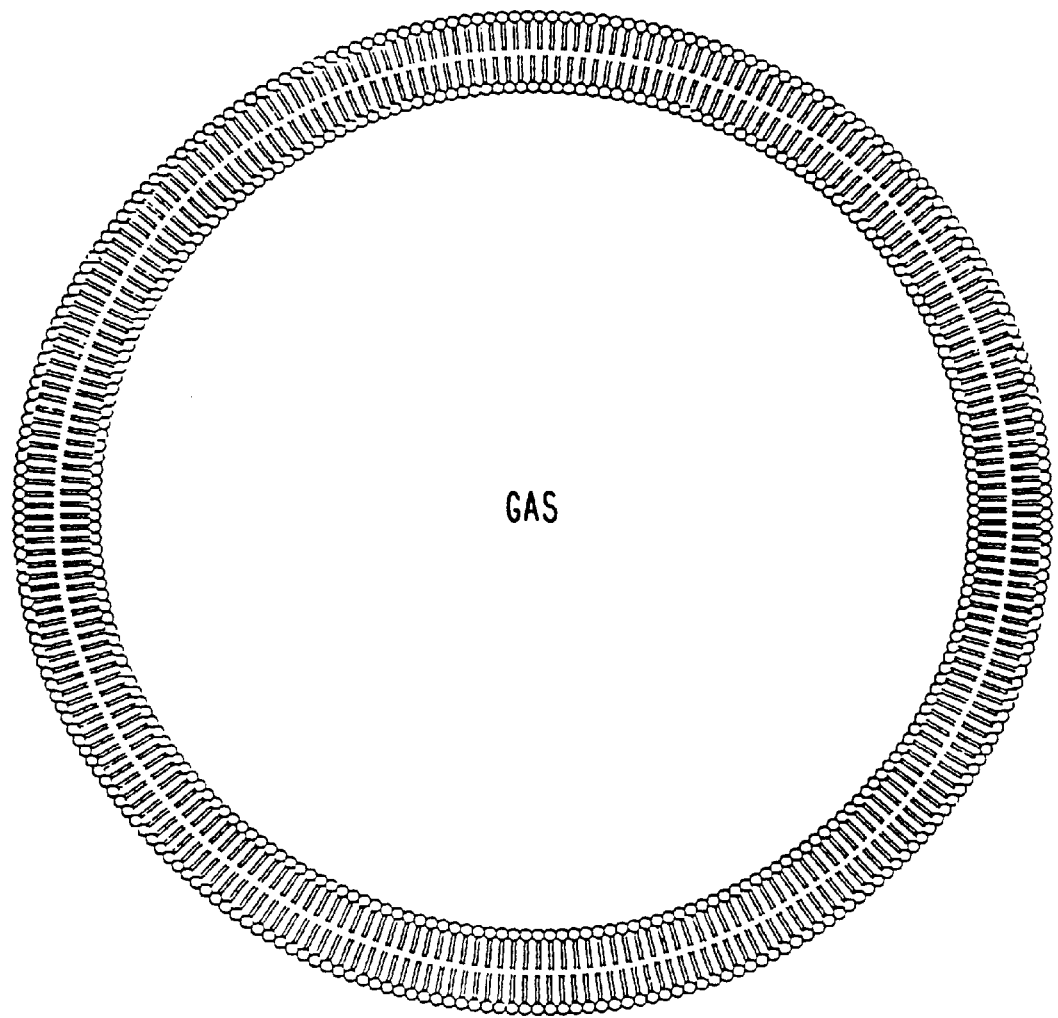

FIG. 10 is a diagrammatic illustration of a temperature activated liquid gaseous precursor-filled liposome after temperature activation of the liquid to gaseous state resulting in a unilamellar membrane and expansion of the liposome diameter.

DETAILED DESCRIPTION OF THE INVENTION

The present invention is directed to methods and apparatus for preparing temperature activated gaseous precursor-filled liposomes. Unlike the methods of the prior art which are directed to the formation of liposomes with an aqueous solution filling the interior, the methods of the present invention are directed to the preparation of liposomes which comprise interior gaseous precursor and/or ultimately gas.

As used herein, the phrase "temperature activated gaseous precursor" denotes a compound which, at a selected activation or transition temperature, changes phases from a liquid to a gas. Activation or transition temperature, and like terms, refer to the boiling point of the gaseous precursor, the temperature at which the liquid to gaseous phase transition of the gaseous precursor takes place. Useful gaseous precursors are those gases which have boiling points in the range of about –100° C. to 70° C. The activation temperature is particular to each gaseous precursor. This concept is illustrated in FIGS. 9 and 10. An activation temperature of about 37° C., or human body temperature, is preferred for gaseous precursors of the present invention. Thus, a liquid gaseous precursor is activated to become a gas at 37° C. However, the gaseous precursor may be in liquid or gaseous phase for use in the methods of the present invention. The methods of the present invention may be carried out below the boiling point of the gaseous precursor such that a liquid is incorporated into a microsphere. In addition, the methods may be performed at the boiling point of the gaseous precursor such that a gas is incorporated into a microsphere. For gaseous precursors having low temperature boiling points, liquid precursors may be emulsified using a microfluidizer device chilled to a low temperature. The boiling points may also be depressed using solvents in liquid media to utilize a precursor in liquid form. Alternatively, an upper limit of about 70° C. may be attained with focused high energy ultrasound. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor-filled microspheres may be carried out at a temperature below the boiling point of the gaseous precursor. In this embodiment, the gaseous precursor is entrapped within a microsphere such that the phase transition does not occur during manufacture. Instead, the gaseous precursor-filled microspheres are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the liposomes upon attaining the gaseous state may be determined.

Alternatively, the gaseous precursors may be utilized to create stable gas-filled microspheres which are pre-formed prior to use. In this embodiment, the gaseous precursor is added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas-filled lipid spheres which entrap the gas of the gaseous precursor, ambient gas (e.g. air) or coentrap gas state gaseous precursor and ambient air. This phase transition can be used for optimal mixing and stabilization of the contrast medium. For example, the gaseous precursor, perfluorobutane, can be entrapped in liposomes and as the temperature is raised, beyond 3° C. (boiling point of perfluorobutane) liposomally entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas-filled liposomes result.

Accordingly, the gaseous precursors of the present invention may be selected to form a gas-filled liposome in vivo or designed to produce the gas-filled liposome in situ, during the manufacturing process, on storage, or at some time prior to use.

As a further embodiment of this invention, by preforming the liquid state of the gaseous precursor into an aqueous emulsion and maintaining a known size, the maximum size of the microbubble may be estimated by using the ideal gas law, once the transition to the gaseous state is effectuated. For the purpose of making gaseous microspheres from gaseous precursors, the gas phase is assumed to form instantaneously and no gas in the newly formed microbubble has been depleted due to diffusion into the liquid (generally aqueous in nature). Hence, from a known liquid volume in the emulsion, one actually would predict an upper limit to the size of the gaseous liposome.

Pursuant to the present invention, an emulsion of lipid gaseous precursor-containing liquid droplets of defined size may be formulated, such that upon reaching a specific temperature, the boiling point of the gaseous precursor, the droplets will expand into gas liposomes of defined size. The defined size represents an upper limit to the actual size because factors such as gas diffusing into solution, loss of gas to the atmosphere, and the effects of increased pressure are factors for which the ideal gas law cannot account.

The ideal gas law and the equation for calculating the increase in volume of the gas bubbles on transition from the liquid to gaseous states follows:

The ideal gas law predicts the following:

$$PV=nRT$$

where

P=pressure in atmospheres

V=volume in liters n=moles of gas

T=temperature in ° K

R=ideal gas constant=22.4 L atmospheres deg$^{-1}$ mole$^{-1}$

With knowledge of volume, density, and temperature of the liquid in the emulsion of liquids, the amount (e.g. number of moles) of liquid precursor as well as the volume of liquid precursor, a priori, may be calculated, which when converted to a gas, will expand into a liposome of known volume. The calculated volume will reflect an upper limit to the size of the gaseous liposome assuming instantaneous expansion into a gas liposome and negligible diffusion of the gas over the time of the expansion.

Thus, stabilization of the precursor in the liquid state in an emulsion whereby the precursor droplet is spherical, the volume of the precursor droplet may be determined by the equation:

$$\text{Volume (sphere)}=4/3\pi r^3$$

where r=radius of the sphere

Thus, once the volume is predicted, and knowing the density of the liquid at the desired temperature, the amount of liquid (gaseous precursor) in the droplet may be determined. In more descriptive terms, the following can be applied:

$$V_{gas}=4/3\pi(r_{gas})^3$$

by the ideal gas law, $$PV=nRT$$

substituting reveals, $$V_{gas}=nRT/P_{gas}$$

or, $$n=4/3[\pi r_{gas}^3]P/RT \quad \text{(A)}$$

amount $n=4/3[\pi r_{gas}^3 P/RT]*MW_n$

Converting back to a liquid volume $$V_{liq}=[4/3[\pi r_{gas}^3]P/RT]*MW_n/D] \quad \text{(B)}$$

where D=the density of the precursor

Solving for the diameter of the liquid droplet, $$\text{diameter}/2=[3/4\pi[4/3*[\pi r_{gas}^3]P/RT]MW_n/D]^{1/3} \quad \text{(C)}$$

which reduces to $$\text{Diameter}=2[[r_{gas}^3]P/RT\,[MW_n/D]]^{1/3}$$

As a further embodiment of the present invention, with the knowledge of the volume and especially the radius, the appropriately sized filter sizes the gaseous precursor droplets to the appropriate diameter sphere.

A representative gaseous precursor may be used to form a microsphere of defined size, for example, 10 microns diameter. In this example, the microsphere is formed in the bloodstream of a human being, thus the typical temperature would be 37° C. or 310° K. At a pressure of 1 atmosphere and using the equation in (A), $7.54\times10^{-17}$ moles of gaseous precursor would be required to fill the volume of a 10 micron diameter microsphere.

Using the above calculated amount of gaseous precursor, and 1-fluorobutane, which possesses a molecular weight of 76.11, a boiling point of 32.5° C. and a density of 6.7789 grams/$mL^{-1}$ at 20° C., further calculations predict that $5.74\times10^{-15}$ grams of this precursor would be required for a 10 micron microsphere. Extrapolating further, and armed with the knowledge of the density, equation (B) further predicts that $8.47\times10^{-16}$ mLs of liquid precursor are necessary to form a microsphere with an upper limit of 10 microns.

Finally, using equation (C), an emulsion of lipid droplets with a radius of 0.0272 microns or a corresponding diameter of 0.0544 microns need be formed to make a gaseous precursor filled microsphere with an upper limit of a 10 micron microsphere.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment of the present invention may be applied to all gaseous precursors activated by temperature. In fact, depression of the freezing point of the solvent system allows the use gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be explained by physical methods as well. When substances, solid or liquid, herein referred to as solutes, are dissolved in a solvent, such as water based buffers for example, the freezing point is lowered by an amount that is dependent upon the composition of the solution. Thus, as defined by Wall, one can express the freezing point depression of the solvent by the following:

$$\ln x_a = \ln(1-x_b) = \Delta H_{fus}/R(1/T_o - 1/T)$$

where:
$x_a$=mole fraction of the solvent
$x_b$=mole fraction of the solute
$\Delta H_{fus}$=heat of fusion of the solvent
$T_o$=Normal freezing point of the solvent The normal freezing point of the solvent results. If $x_b$ is small relative to $x_a$, then the above equation may be rewritten:

$$x^b = \Delta H_{fus}/R[T-T_o/T_oT] \approx \Delta H_{fus}\Delta T/RT_o^2$$

The above equation assumes the change in temperature $\Delta T$ is small compared to $T_2$. The above equation can be simplified further assuming the concentration of the solute (in moles per thousand grams of solvent) can be expressed in terms of the molality, m. Thus, $$X_b = m/[m+1000/M_a] \approx mMa/1000$$

where:
Ma=Molecular weight of the solvent, and
m=molality of the solute in moles per 1000 grams.
Thus, substituting for the fraction $x_b$:

$$\Delta T = [M_aRT_o^2/1000\Delta H_{fus}]m$$

or $\Delta T = K_f m$, where $$K_f = M_a RT_o^2/1000\Delta H_{fus}$$

$K_f$ is referred to as the molal freezing point and is equal to 1.86 degrees per unit of molal concentration for water at one atmosphere pressure. The above equation may be used to accurately determine the molal freezing point of gaseous-precursor filled microsphere solutions of the present invention.

Hence, the above equation can be applied to estimate freezing point depressions and to determine the appropriate concentrations of liquid or solid solute necessary to depress the solvent freezing temperature to an appropriate value.

Methods of preparing the temperature activated gaseous precursor-filled liposomes include:

vortexing an aqueous suspension of gaseous precursor-filled liposomes of the present invention; variations on this method include optionally autoclaving before shaking, optionally heating an aqueous suspension of gaseous precursor and lipid, optionally venting the vessel containing the suspension, optionally shaking or permitting the gaseous precursor liposomes to form spontaneously and cooling down the gaseous precursor filled liposome suspension, and optionally extruding an aqueous suspension of gaseous precursor and lipid through a filter of about 0.22 μm, alternatively, filtering may be performed during in vivo administration of the resulting liposomes such that a filter of about 0.22 μm is employed;

a microemulsification method whereby an aqueous suspension of gaseous precursor-filled liposomes of the present invention are emulsified by agitation and heated to form microspheres prior to administration to a patient; and forming a gaseous precursor in lipid suspension by heating, and/or agitation, whereby the less dense gaseous precursor-filled microspheres float to the top of the solution by expanding and displacing other microspheres in the vessel and venting the vessel to release air.

Freeze drying is useful to remove water and organic materials from the lipids prior to the shaking gas instillation method. Drying-gas instillation method may be used to remove water from liposomes. By pre-entrapping the gaseous precursor in the dried liposomes (i.e. prior to drying) after warming, the gaseous precursor may expand to fill the liposome. Gaseous precursors can also be used to fill dried liposomes after they have been subjected to vacuum. As the dried liposomes are kept at a temperature below their gel state to liquid crystalline temperature the drying chamber can be slowly filled with the gaseous precursor in its gaseous state, e.g. perfluorobutane can be used to fill dried liposomes composed of dipalmitoylphosphatidylcholine (DPPC) at temperatures between 3° C. (the boiling point of perfluorobutane) and below 40° C., the phase transition temperature of the lipid. In this case, it would be most preferred to fill the liposomes at a temperature about 4° C. to about 5° C.

Preferred methods for preparing the temperature activated gaseous precursor-filled liposomes comprise shaking an aqueous solution having a lipid in the presence of a gaseous precursor at a temperature below the gel state to liquid crystalline state phase transition temperature of the lipid. The present invention also provides a method for preparing gaseous precursor-filled liposomes comprising shaking an aqueous solution comprising a lipid in the presence of a gaseous precursor, and separating the resulting gaseous precursor-filled liposomes for diagnostic or therapeutic use. Liposomes prepared by the foregoing methods are referred to herein as gaseous precursor-filled liposomes prepared by a gel state shaking gaseous precursor installation method.

Conventional, aqueous-filled liposomes are routinely formed at a temperature above the phase transition temperature of the lipid, since they are more flexible and thus useful in biological systems in the liquid crystalline state. See, for example, Szoka and Papahadjopoulos, *Proc. Natl. Acad. Sci.* 1978, 75, 4194–4198. In contrast, the liposomes made according to preferred embodiments of the methods of the present invention are gaseous precursor-filled, which imparts greater flexibility since gaseous precursors after gas formation are more compressible and compliant than an aqueous solution. Thus, the gaseous precursor-filled liposomes may be utilized in biological systems when formed at a temperature below the phase transition temperature of the lipid, even though the gel phase is more rigid.

The methods of the present invention provide for shaking an aqueous solution comprising a lipid in the presence of a temperature activated gaseous precursor. Shaking, as used herein, is defined as a motion that agitates an aqueous solution such that gaseous precursor is introduced from the local ambient environment into the aqueous solution. Any type of motion that agitates the aqueous solution and results in the introduction of gaseous precursor may be used for the shaking. The shaking must be of sufficient force to allow the formation of foam after a period of time. Preferably, the shaking is of sufficient force such that foam is formed within a short period of time, such as 30 minutes, and preferably within 20 minutes, and more preferably, within 10 minutes. The shaking may be by microemulsifying, by microfluidizing, for example, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table, such as a VWR Scientific (Cerritos, Calif.) shaker table, a microfluidizer, Wig-L-Bug™ (Crescent Dental Manufacturing, Inc., Lyons, Ill.) and a mechanical paint mixer, as well as other known machines. Another means for producing shaking includes the action of gaseous precursor emitted under high velocity or pressure. It will also be understood that preferably, with a larger volume of aqueous solution, the total amount of force will be correspondingly increased. vigorous shaking is defined as at least about 60 shaking motions per minute, and is preferred. Vortexing at at least 1000 revolutions per minute, an example of vigorous shaking, is more preferred. Vortexing at 1800 revolutions per minute is most preferred.

The formation of gaseous precursor-filled liposomes upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gaseous precursor-filled liposomes becomes sufficiently thick so that it no longer clings to the side walls as it is swirled. At this time, the foam may cause the solution containing the gaseous precursor-filled liposomes to raise to a level of 30 to 35 ml.

The concentration of lipid required to form a preferred foam level will vary depending upon the type of lipid used, and may be readily determined by one skilled in the art, once armed with the present disclosure. For example, in preferred embodiments, the concentration of 1,2-dipalimitoylphosphatidylcholine (DPPC) used to form gaseous precursor-filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gaseous precursor volume four times greater than the suspension volume alone. DSPC in a concentration of 10 mg/ml, upon shaking, yields a total volume completely devoid of any liquid suspension volume and contains entirely foam.

It will be understood by one skilled in the art, once armed with the present disclosure, that the lipids or liposomes may be manipulated prior and subsequent to being subjected to the methods of the present invention. For example, the lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gaseous precursor-filled liposomes.

According to the methods of the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier athan air may be added to a sealed container while gases heavier than air may be added to a sealed or an unsealed container. Accordingly, the present invention includes co-entrapment of air and/or other gases along with gaseous precursors.

The preferred methods of the invention are carried out at a temperature below the gel state to liquid crystalline state phase transition temperature of the lipid employed. By "gel state to liquid crystalline state phase transition temperature", it is meant the temperature at which a lipid bilayer will convert from a gel state to a liquid crystalline state. See, for example, Chapman et al., *J. Biol. Chem.* 1974, 249, 2512–2521. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984) and Derek Marsh, *CRC Handbook of Lipid Bilayers* (CRC Press, Boca Raton, Fla. 1990), at p. 139. See also Table I, below. Where the gel state to liquid crystalline state phase transition temperature of the lipid employed is higher than room temperature, the temperature of the container may be regulated, for example, by providing a cooling mechanism to cool the container holding the lipid solution.

Since gaseous precursors (e.g. perfluorobutane) are less soluble and diffusable than other gases, such as air, they tend to be more stable when entrapped in liposomes even when the liposomes are composed of lipids in the liquid-crystalline state. Small liposomes composed of liquid-crystalline state lipid such as egg phosphatidyl choline may be used to entrap a nanodroplet of perfluorobutane. For example, lipid vesicles with diameters of about 30 nm to about 50 nm may be used to entrap nanodroplets of perfluorobutane a mean diameter of about 25 nm. After temperature activated conversion, the precursor filled liposomes will create microspheres of about 10 microns in diameter. The lipid in this case, serves the purpose of defining the size of the microsphere via the small liposome. The lipids also serve to stabilize the resultant microsphere size. In this case, techniques such as microemulsification are preferred for forming the small liposomes which entrap the precursor. A microfluidizer (Microfluidics, Newton, Mass.) is particularly useful for making an emulsion of small liposomes which entrap the gaseous precursor.

TABLE I

Saturated Diacyl-sn-Glycero-3-Phosphocholines
Main Chain Gel State to Liquid Crystalline State
Phase Transition Temperatures

| # Carbons in Acyl Chains | Liquid Crystalline Phase Transition Temperature (° C.) |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |

TABLE I-continued

Saturated Diacyl-sn-Glycero-3-Phosphocholines
Main Chain Gel State to Liquid Crystalline State
Phase Transition Temperatures

| # Carbons in Acyl Chains | Liquid Crystalline Phase Transition Temperature (° C.) |
|---|---|
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

Conventional, aqueous-filled liposomes are routinely formed at a temperature above the gel to liquid crystalline phase transition temperature of the lipid, since they are more flexible and thus useful in biological systems in the liquid crystalline state. See, for example, Szoka and Papahadjopoulos, *Proc. Natl. Acad. Sci.* 1978, 75, 4194–4198. In contrast, the liposomes made according to preferred embodiments of the methods of the present invention are gaseous precursor-filled, which imparts greater flexibility since gaseous precursor is more compressible and compliant than an aqueous solution. Thus, the gaseous precursor-filled liposomes may be utilized in biological systems when formed at a temperature below the phase transition temperature of the lipid, even though the gel phase is more rigid.

Figure 1:
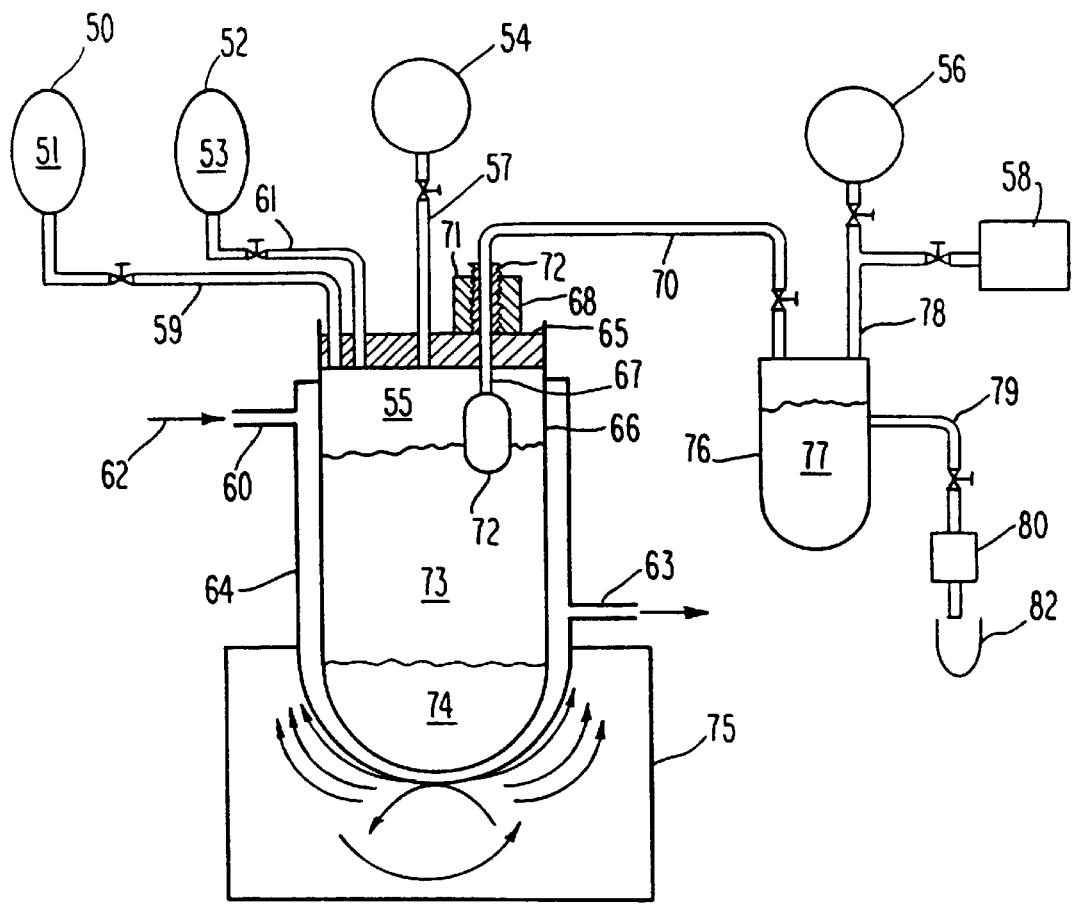
FIG. 1 is a view, partially schematic, of a preferred apparatus according to the present invention for preparing the gaseous precursor-filled liposome microspheres of the present invention.

A preferred apparatus for producing the temperature activated gaseous precursor-filled liposomes using a gel state shaking gaseous precursor instillation process is shown in FIG. 1. A mixture of lipid and aqueous media is vigorously agitated in the presence of gaseous precursor to produce gaseous precursor-filled liposomes, either by batch or by continuous feed. Referring to FIG. 1, dried lipids 51 from a lipid supply vessel 50 are added via conduit 59 to a mixing vessel 66 in either a continuous flow or as intermittent boluses. If a batch process is utilized, the mixing vessel 66 may comprise a relatively small container such as a syringe, test tube, bottle or round bottom flask, or a large container. If a continuous feed process is utilized, the mixing vessel is preferably a large container, such as a vat.

Where the gaseous precursor-filled liposomes contain a therapeutic compound, the therapeutic compound may be added, for example, in a manner similar to the addition of the lipid described above before the gaseous precursor installation process. Alternatively, the therapeutic compound may be added after the gaseous precursor installation process when the liposomes are coated on the outside with the therapeutic compound.

In addition to the lipids 51, an aqueous media 53, such as a saline solution, from an aqueous media supply vessel 52, is also added to the vessel 66 via conduit 61. The lipids 51 and the aqueous media 53 combine to form an aqueous lipid solution 74. Alternatively, the dried lipids 51 could be hydrated prior to being introduced into the mixing vessel 66 so that lipids are introduced in an aqueous solution. In the preferred embodiment of the method for making liposomes, the initial charge of solution 74 is such that the solution occupies only a portion of the capacity of the mixing vessel 66. Moreover, in a continuous process, the rates at which the aqueous lipid solution 74 is added and gaseous-precursor-filled liposomes produced are removed is controlled to ensure that the volume of lipid solution 74 does not exceed a predetermined percentage of the mixing vessel 66 capacity.

The shaking may be accomplished by introducing a high velocity jet of a pressurized gaseous precursor directly into the aqueous lipid solution 74. Alternatively, the shaking may be accomplished by mechanically shaking the aqueous solution, either manually or by machine. Such mechanical shaking may be effected by shaking the mixing vessel 66 or by shaking the aqueous solution 74 directly without shaking the mixing vessel itself. As shown in FIG. 1, in the preferred embodiment, a mechanical shaker 75, is connected to the mixing vessel 66. The shaking should be of sufficient intensity so that, after a period of time, a foam 73 comprised of gaseous precursor-filled liposomes is formed on the top of the aqueous solution 74, as shown in FIG. 1. The detection of the formation of the foam 73 may be used as a means for controlling the duration of the shaking; that is, rather than shaking for a predetermined period of time, the shaking may be continued until a predetermined volume of foam has been produced.

The apparatus of FIG. 1 may also contain a means for controlling temperature such that the apparatus may be maintained at one temperature for the method of making the liposomes. For example, in the preferred embodiment, the methods of making liposomes are performed at a temperature below the boiling point of the gaseous precursor. In the preferred embodiment, a liquid gaseous precursor fills the internal space of the liposomes. Alternatively, the apparatus may be maintained at about the temperature of the liquid to gas transition temperature of the gaseous precursor such that a gas is contained in the liposomes. Further, the temperature of the apparatus may be adjusted throughout the method of making the liposomes such that the gaseous precursor begins as a liquid, however, a gas is incorporated into the resulting liposomes. In this embodiment, the temperature of the apparatus is adjusted during the method of making the liposomes such that the method begins at a temperature below the phase transition temperature and is adjusted to a temperature at about the phase transition temperature of the gaseous precursor. Accordingly, the vessel may be closed and periodically vented, or open to the ambient atmosphere.

In a preferred embodiment of the apparatus for making gaseous precursor-filled liposomes in which the lipid employed has a gel to liquid crystalline phase transition temperature below room temperature, a means for cooling the aqueous lipid solution 74 is provided. In the embodiment shown in FIG. 1, cooling is accomplished by means of a jacket 64 disposed around the mixing vessel 66 so as to form an annular passage surrounding the vessel. As shown in FIG. 1, a cooling fluid 63 is forced to flow through this annular passage by means of jacket inlet and outlet ports 62 and 63, respectively. By regulating the temperature and flow rate of the cooling fluid 62, the temperature of the aqueous lipid solution 74 can be maintained at the desired temperature.

As shown in FIG. 1, a gaseous precursor 55, which may be 1-fluorobutane, for example, is introduced into the mixing vessel 66 along with the aqueous solution 74. Air may be introduced by utilizing an unsealed mixing vessel so that the aqueous solution is continuously exposed to environmental air. In a batch process, a fixed charge of local ambient air may be introduced by sealing the mixing vessel 66. If a gaseous precursor heavier than air is used, the container need not be sealed. However, introduction of gaseous precursors that are not heavier than air will require that the mixing vessel be sealed, for example by use of a lid 65, as shown in FIG. 1. The gaseous precursor 55 may be pressurized in the mixing vessel 66, for example, by connecting the mixing vessel to a pressurized gas supply tank 54 via a conduit 57, as shown in FIG. 1.

After the shaking is completed, the gaseous precursor-filled liposome containing foam 73 may be extracted from the mixing vessel 66. Extraction may be accomplished by inserting the needle 102 of a syringe 100, shown in FIG. 2, into the foam 73 and drawing a predetermined amount of foam into the barrel 104 by withdrawing the plunger 106. As discussed further below, the location at which the end of the needle 102 is placed in the foam 73 may be used to control the size of the gaseous precursor-filled liposomes extracted.

Alternatively, extraction may be accomplished by inserting an extraction tube 67 into the mixing vessel 66, as shown in FIG. 1. If the mixing vessel 66 is pressurized, as previously discussed, the pressure of the gaseous precursor 55 may be used to force the gaseous precursor-filled liposomes 77 from the mixing vessel 66 to an extraction vessel 76 via conduit 70. In the event that the mixing vessel 66 is not pressurized, the extraction vessel 76 may be connected to a vacuum source 58, such as a vacuum pump, via conduit 78, that creates sufficient negative pressure to suck the foam 73 into the extraction vessel 76, as shown in FIG. 1. From the extraction vessel 76, the gaseous precursor-filled liposomes 77 are introduced into vials 82 in which they may be shipped to the ultimate user. A source of pressurized gaseous precursor 56 may be connected to the extraction vessel 76 as aid to ejecting the gaseous precursor-filled liposomes. Since negative pressure may result in increasing the size of the gaseous precursor-filled liposomes, positive pressure is preferred for removing the gaseous precursor-filled liposomes.

Figures 2, 3, 4:
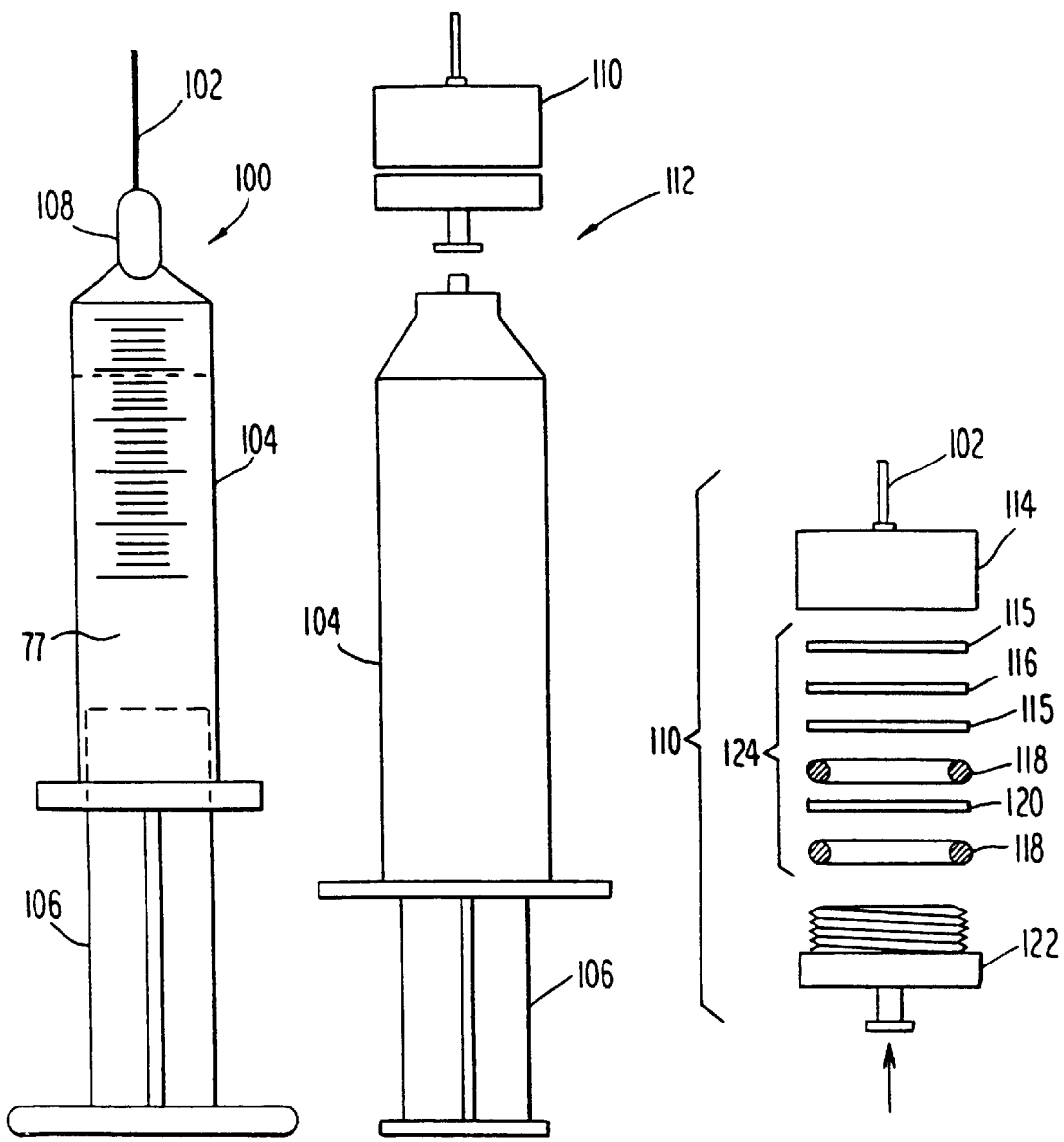
FIG. 2 shows a preferred apparatus for filtering and/or dispensing therapeutic containing gaseous precursor-filled liposome microspheres of the present invention.
FIG. 3 shows a preferred apparatus for filtering and/or dispensing therapeutic containing gaseous precursor-filled liposome microspheres of the present invention.
FIG. 4 is an exploded view of a portion of the apparatus of FIG. 3.
Figure 5A:
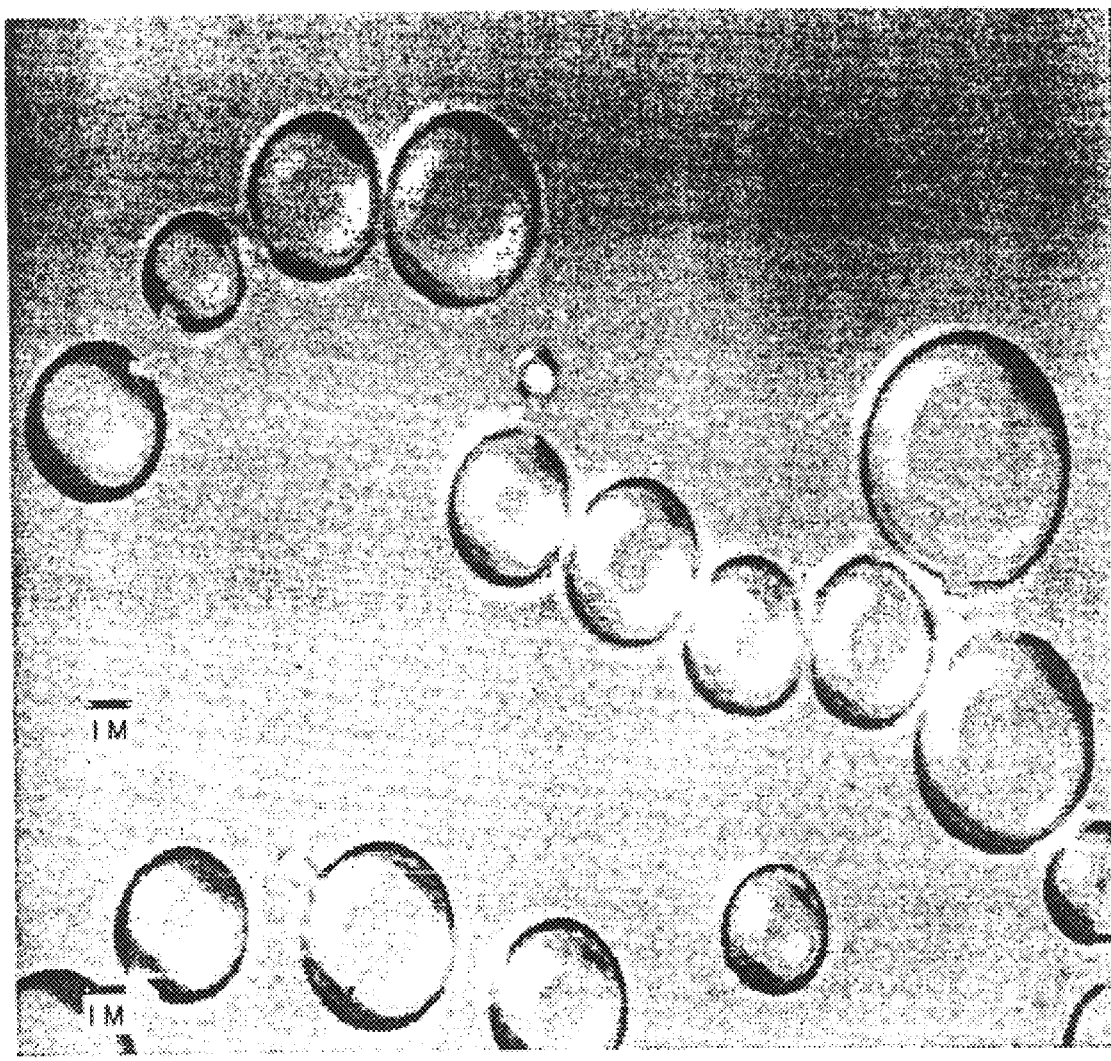
FIGS. 5A and 5B is a micrograph which shows the sizes of gaseous precursor-filled liposomes of the invention before (A) and after (B) filtration.
Figure 5B:
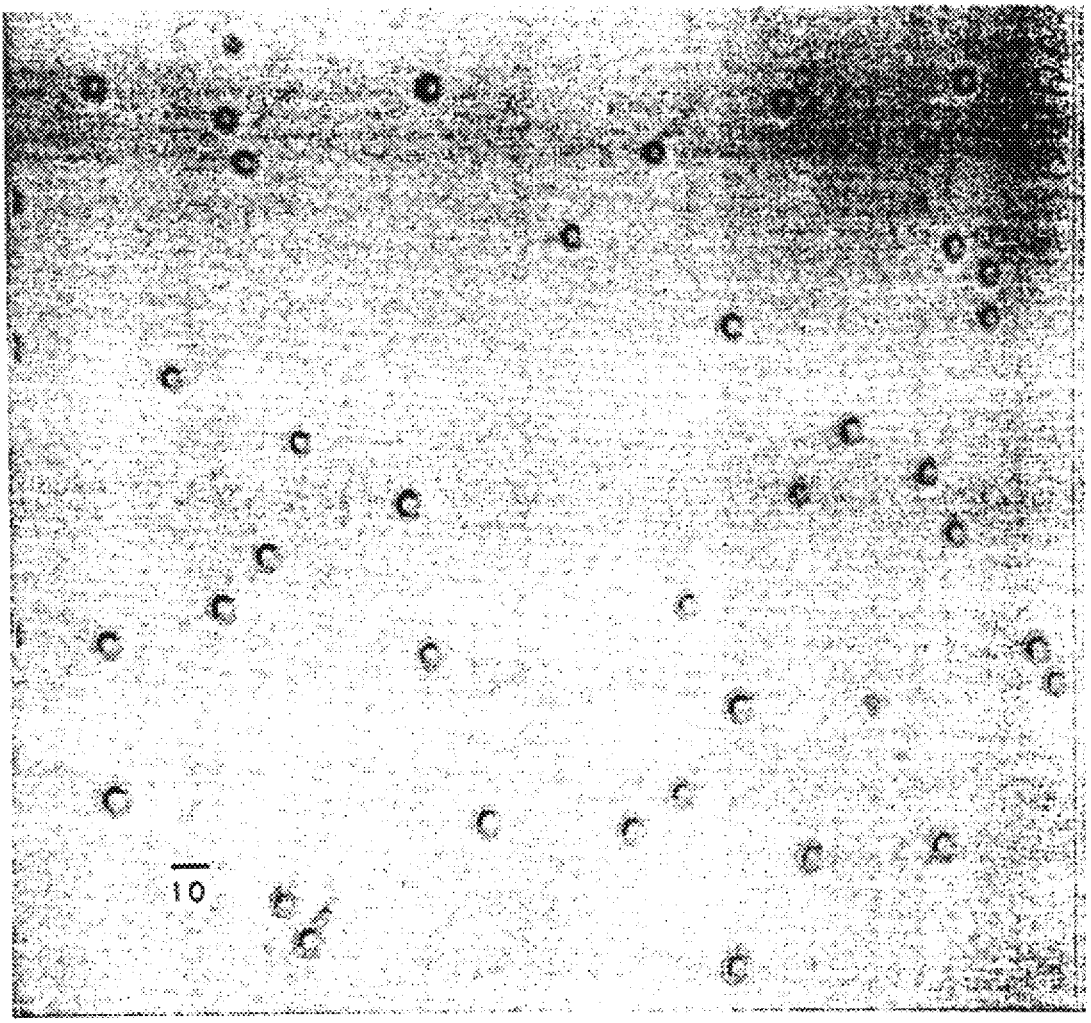

Filtration may be carried out in order to obtain gaseous precursor-filled liposomes of a substantially uniform size. In certain preferred embodiments, the filtration assembly contains more than one filter, and preferably, the filters are not immediately adjacent to each other, as illustrated in FIG. 4. Before filtration, the gaseous precursor-filled liposomes range in size from about 1 micron to greater than 60 microns (FIGS. 5A and 6A). After filtration through a single filter, the gaseous precursor-filled liposomes are generally less than 10 microns but particles as large as 25 microns in size remain. After filtration through two filters (10 micron followed by 8 micron filter), almost all of the liposomes are less than 10 microns, and most are 5 to 7 microns (FIGS. 5B and 6B).

As shown in FIG. 1, filtering may be accomplished by incorporating a filter element 72 directly onto the end of the extraction tube 67 so that only gaseous precursor-filled liposomes below a pre-determined size are extracted from the mixing vessel 66. Alternatively, or in addition to the extraction tube filter 72, gaseous precursor-filled liposome sizing may be accomplished by means of a filter 80 incorporated into the conduit 79 that directs the gaseous precursor-filled liposomes 77 from the extraction vessel 76 to the vials 82, as shown in FIG. 1. The filter 80 may contain a cascade filter assembly 124, such as that shown in FIG. 4. The cascade filter assembly 124 shown in FIG. 4 comprises two successive filters 116 and 120, with filter 120 being disposed upstream of filter 116. In a preferred embodiment, the upstream filter 120 is a "NUCLEPORE" 10 $\mu$m filter and the downstream filter 116 is a "NUCLEPORE" 8 $\mu$m filter. Two 0.15 mm metallic mesh discs 115 are preferably installed on either side of the filter 116. In a preferred embodiment, the filters 116 and 120 are spaced apart a minimum of 150 $\mu$m by means of a Teflon™ O-ring, 118.

In addition to filtering, sizing may also be accomplished by taking advantage of the dependence of gaseous precursor-filled liposome buoyancy on size. The gaseous precursor-filled liposomes have appreciably lower density than water and hence may float to the top of the mixing vessel 66. Since the largest liposomes have the lowest density, they will float most quickly to the top. The smallest liposomes will generally be last to rise to the top and the non gaseous precursor-filled lipid portion will sink to the bottom. This phenomenon may be advantageously used to size the gaseous precursor-filled liposomes by removing them from the mixing vessel 66 via a differential flotation process. Thus, the setting of the vertical location of the extraction tube 67 within the mixing vessel 66 may control the size of the gaseous precursor-filled liposomes extracted; the higher the tube, the larger the gaseous precursor-filled liposomes extracted. Moreover, by periodically or continuously adjusting the vertical location of the extraction tube 67 within the mixing vessel 66, the size of the gaseous precursor-filled liposomes extracted may be controlled on an on-going basis. Such extraction may be facilitated by incorporating a device 68, which may be a threaded collar 71 mating with a threaded sleeve 72 attached to the extraction tube 67, that allows the vertical location of the extraction tube 66 within the extraction vessel 66 to be accurately adjusted.

The gel state shaking gaseous precursor installation process itself may also be used to improve sizing of the gaseous precursor-filled lipid based microspheres. In general, the greater the intensity of the shaking energy, the smaller the size of the resulting gaseous precursor-filled liposomes.

The current invention also includes novel methods for preparing drug-containing gaseous precursor-filled liposomes to be dispensed to the ultimate user. Once gaseous precursor-filled liposomes are formed, they generally cannot be sterilized by heating at a temperature that would cause rupture. Therefore, it is desirable to form the gaseous precursor-filled liposomes from sterile ingredients and to perform as little subsequent manipulation as possible to avoid the danger of contamination. According to the current invention, this may be accomplished, for example, by sterilizing the mixing vessel containing the lipid and aqueous solution before shaking and dispensing the gaseous precursor-filled liposomes 77 from the mixing vessel 66, via the extraction vessel 76, directly into the barrel 104 of a sterile syringe 100, shown in FIG. 2, without further processing or handling; that is, without subsequent sterilization. The syringe 100, charged with gaseous precursor-filled liposomes 77 and suitably packaged, may then be dispensed to the ultimate user. Thereafter, no further manipulation of the product is required in order to administer the gaseous precursor-filled liposomes to the patient, other than removing the syringe from its packaging and removing a protector (not shown) from the syringe needle 102 and inserting the needle into the body of the patient, or into a catheter. Moreover, the pressure generated when the syringe plunger 106 is pressed into the barrel 104 will cause the largest gaseous precursor-filled liposomes to collapse, thereby achieving a degree of sizing without filtration.

Where it is desired to filter the gaseous precursor-filled liposomes at the point of use, for example because they are removed from the extraction vessel 76 without filtration or because further filtration is desired, the syringe 100 may be fitted with its own filter 108, as shown in FIG. 2. This results in the gaseous precursor-filled liposomes being sized by causing them to be extruded through the filter 108 by the action of the plunger 106 when the gaseous precursor-filled liposomes are injected. Thus, the gaseous precursor-filled liposomes may be sized and injected into a patient in one step.

In order to accommodate the use of a single or dual filter in the hub housing of the syringe, a non-standard syringe with hub housing is necessary. As shown in FIG. 3, the hub that houses the filter(s) are of a dimension of approximately 1 cm to approximately 2 cm in diameter by about 1.0 cm to about 3.0 cm in length with an inside diameter of about 0.8 cm for which to house the filters. The abnormally large dimensions for the filter housing in the hub are to accommodate passage of the microspheres through a hub with sufficient surface area so as to decrease the pressure that need be applied to the plunger of the syringe. In this manner, the microspheres will not be subjected to an inordinately large pressure head upon injection, which may cause rupture of the microspheres.

As shown in FIG. 3, a cascade filter housing 110 may be fitted directly onto a syringe 112, thereby allowing cascade filtration at the point of use. As shown in FIG. 4, the filter housing 110 is comprised of a cascade filter assembly 124, previously discussed, incorporated between a lower collar 122, having male threads, and a female collar 114, having female threads. The lower collar 122 is fitted with a Luer lock that allows it to be readily secured to the syringe 112 and the upper collar 114 is fitted with a needle 102.

In preferred embodiments, the lipid solution is extruded through a filter and the lipid solution is heat sterilized prior to shaking. Once gaseous precursor-filled liposomes are formed, they may be filtered for sizing as described above. These steps prior to the formation of gaseous precursor-filled liposomes provide the advantages, for example, of reducing the amount of unhydrated lipid and thus providing a significantly higher yield of gaseous precursor-filled liposomes, as well as and providing sterile gaseous precursor-filled liposomes ready for administration to a patient. For example, a mixing vessel such as a vial or syringe may be filled with a filtered lipid suspension, and the solution may then be sterilized within the mixing vessel, for example, by autoclaving. A gaseous precursor may be instilled into the lipid suspension to form gaseous precursor-filled liposomes by shaking the sterile vessel. Preferably, the sterile vessel is equipped with a filter positioned such that the gaseous precursor-filled liposomes pass through the filter before contacting a patient.

The first step of this preferred method, extruding the lipid solution through a filter, decreases the amount of unhydrated lipid by breaking up the dried lipid and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and even more preferably, about 1 $\mu$m, most preferably 0.22 $\mu$m. As shown in FIGS. 7A and 7B, when a lipid suspension is filtered (FIG. 7B), the amount of unhydrated lipid is reduced when compared to a lipid suspension that was not pre-filtered (FIG. 7A). Unhydrated lipid appears as amorphous clumps of non-uniform size and is undesirable.

The second step, sterilization, provides a composition that may be readily administered to a patient. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

Where sterilization occurs by a process other than heat sterilization at a temperature which would cause rupture of the gaseous precursor-filled liposomes, sterilization may occur subsequent to the formation of the gaseous precursor-filled liposomes, and is preferred. For example, gamma radiation may be used before and/or after gaseous precursor-filled liposomes are formed.

Sterilization of the gaseous precursor may be achieved via passage through a 0.22 $\mu$m filter or a smaller filter, prior to emulsification in the aqueous media. This can be easily achieved via sterile filtration of the contents directly into a vial which contains a predetermined amount of likewise sterilized and sterile-filled aqueous carrier.

FIGS. 8A and 8B illustrates the ability of gaseous precursor-filled liposomes to successfully form after autoclaving, which was carried out at 130° C. for 15 minutes, followed by vortexing for 10 minutes. Further, after the extrusion and sterilization procedure, the shaking step yields gaseous precursor-filled liposomes with little to no residual anhydrous lipid phase. FIG. 8A shows gaseous precursor-filled liposomes generated after autoclaving but prior to filtration, thus resulting in a number of gaseous precursor-filled liposomes having a size greater than 10 $\mu$m. FIG. 8B shows gaseous precursor-filled liposomes after a filtration through a 10 $\mu$m "NUCLEPORE" filter, resulting in a uniform size around 10 $\mu$m.

The materials which may be utilized in preparing the gaseous precursor-filled lipid microspheres include any of the materials or combinations thereof known to those skilled in the art as suitable for liposome preparation. Gas precursors which undergo phase transition from a liquid to a gas at their boiling point may be used in the present invention. The lipids used may be of either natural or synthetic origin. The particular lipids are chosen to optimize the desired properties, e.g., short plasma half-life versus long plasma half-life for maximal serum stability. It will also be understood that certain lipids may be more efficacious for particular applications, such as the containment of a therapeutic compound to be released upon rupture of the gaseous precursor-filled lipid microsphere.

The lipid in the gaseous precursor-filled liposomes may be in the form of a single bilayer or a multilamellar bilayer, and are preferably multilamellar.

Gaseous precursors which may be activated by temperature may be useful in the present invention. Table II lists examples of gaseous precursors which undergo phase transitions from liquid to gaseous states at close to normal body temperature (37° C.) and the size of the emulsified droplets that would be required to form a microsphere having a size of 10 microns. The list is composed of potential gaseous precursors that may be used to form temperature activated gaseous precursor-containing liposomes of a defined size. The list should not be construed as being limiting by any means, as to the possibilities of gaseous precursors for the methods of the present invention.

TABLE II

Physical Characteristics of Gaseous Precursors and Diameter of Emulsified Droplet to Form a 10 $\mu$m Microsphere

| Compound | Molecular Weight | Boiling Point (° C.) | Density | Diameter ($\mu$m) of Emulsified droplet to make 10 micron microsphere |
|---|---|---|---|---|
| 1-fluorobutane | 76.11 | 32.5 | 6.7789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |

TABLE II-continued

Physical Characteristics of Gaseous Precursors and
Diameter of Emulsified Droplet to Form a 10 μm Microsphere

| Compound | Molecular Weight | Boiling Point (° C.) | Density | Diameter (μm) of Emulsified droplet to make 10 micron microsphere |
|---|---|---|---|---|
| perfluoro methane | 88.00 | −129 | 3.034 | 3.3 |
| perfluoro ethane | 138.01 | −79 | 1.590 | 1.0 |
| perfluoro butane | 238.03 | 3.96 | 1.6484 | 2.8 |
| perfluoro pentane | 288.04 | 57.73 | 1.7326 | 2.9 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |
| docecafluoro pentane | 288.05 | 29.5 | 1.664 | 2.9 |
| octafluoro-2-butene | 200.04 | 1.2 | 1.5297 | 2.8 |
| perfluoro cyclobutane | 200.04 | −5.8 | 1.48 | 2.8 |
| octafluoro cyclopentene | 212.05 | 27 | 1.58 | 2.7 |
| perfluoro cyclobutene | 162 | 5 | 1.602 | 2.5 |

*Source: Chemical Rubber Company Handbook of Chemistry and Physics Robert C. Weast and David R. Lide, eds. CRC Press, Inc. Boca Raton, Florida. (1989–1990).

Examples of gaseous precursors are by no means limited to Table II. In fact, for a variety of different applications, virtually any liquid can be used to make gaseous precursors so long as it is capable of undergoing a phase transition to the gas phase upon passing through the appropriate activation temperature. Examples of gaseous precursors that may be used include, and are by no means limited to, the following: hexafluoro acetone; isopropyl acetylene; allene; tetrafluoroallene; boron trifluoride; 1,2-butadiene; 1,3-butadiene; 1,3-butadiene; 1,2,3-trichloro, 2-fluoro-1,3-butadiene; 2-methyl, 1,3 butadiene; hexafluoro-1,3-butadiene; butadiyne; 1-fluoro-butane; 2-methyl-butane; decafluoro butane; 1-butene; 2-butene; 2-methy-1-butene; 3-methyl-1-butene; perfluoro-1-butene; perfluoro-1-butene; perfluoro-2-butene; 1,4-phenyl-3-butene-2-one; 2-methyl-1-butene-3-yne; butyl nitrate; 1-butyne; 2-butyne; 2-chloro-1,1,1,4,4,4-hexafluoro-butyne; 3-methyl-1-butyne; perfluoro-2-butyne; 2-bromo-butyraldehyde; carbonyl sulfide; crotononitrile; cyclobutane; methyl-cyclobutane; octafluoro-cyclobutane; perfluoro-cyclobutene; 3-chloro-cyclopentene; perfluoro ethane; perfluoro propane; perfluoro butane; perfluoro pentane; perfluoro hexane;cyclopropane; 1,2-dimethyl-cyclopropane; 1,1-dimethyl cyclopropane; 1,2-dimethyl cyclopropane; ethyl cyclopropane; methyl cyclopropane; diacetylene; 3-ethyl-3-methyl diaziridine; 1,1,1-trifluorodiazoethane; dimethyl amine; hexafluoro-dimethyl amine; dimethylethylamine; -bis-(Dimethyl phosphine)amine; 2,3-dimethyl-2-norbornane; perfluo-rodimethylamine; dimethyloxonium chloride; 1,3-dioxolane-2-one; perfluorocarbons such as and not limited to 4-methyl,1,1,1,2-tetrafluoro ethane; 1,1,1-trifluoroethane; 1,1,2,2-tetrafluoroethane; 1,1,2-trichloro-1,2,2-trifluoroethane; 1,1 dichloroethane; 1,1-dichloro-1,2,2,2-tetrafluoro ethane; 1,2-difluoro ethane; 1-chloro-1,1,2,2,2-pentafluoro ethane; 2-chloro, 1,1-difluoroethane; 1-chloro-1,1,2,2-tetrafluoro ethane; 2-chloro, 1,1-difluoroethane; chloroethane; chloropentafluoro ethane; dichlorotrifluoroet-hane; fluoro-ethane; hexafluoro-ethane; nitro-pentafluoro ethane; nitroso-pentafluoro ethane; perfluoro ethane; per-fluoro ethylamine; ethyl vinyl ether; 1,1-dichloro ethylene; 1,1-dichloro-1,2-difluoro ethylene; 1,2-difluoro ethylene; Methane; Methane-sulfonyl chloride-trifluoro; Methane-sulfonyl fluoride-trifluoro; Methane-(pentafluorothio) trifluoro; Methane-bromo difluoro nitroso; Methane-bromo fluoro; Methane-bromo chloro-fluoro; Methanebromo-trifluoro; Methane-chloro difluoro nitro; Methane-chloro dinitro; Methanechloro fluoro; Methane-chloro trifluoro; Methane-chloro-difluoro; Methane dibromo difluoro; Methane-dichloro difluoro; Methane-dichloro-fluoro; Meth-anedifluoro; Methane-difluoro-iodo; Methane-disilano; Methane-fluoro; Methaneiodo; Methane-iodo-trifluoro; Methane-nitro-trifluoro; Methane-nitroso-trifluoro; Methane-tetrafluoro; Methane-trichlorofluoro; Methane-trifluoro; Methanesulfenylchloride-trifluoro; 2-Methyl butane; Methyl ether; Methyl isopropyl ether; Methyl lac-tate; Methyl nitrite; Methyl sulfide; Methyl vinyl ether; Neon; Neopentane; Nitrogen ($N_2$); Nitrous oxide; 1,2,3-Nonadecane tricarboxylic acid-2-hydroxytrimethylester; 1-Nonene-3-yne; Oxygen ($O_2$); 1,4-Pentadiene; n-Pentane; Pentane-perfluoro; 2-Pentanone-4-amino-4-methyl; 1-Pentene; 2-Pentene [cis]; 2-Pentene (trans); 1-Pentene-3-bromo; 1-Pentene-perfluoro; Phthalic acid-tetrachloro; Piperidine-2,3,6-trimethyl; Propane, Propane-1,1,1,2,2,3-hexafluoro; Propane-1,2-epoxy; Propane-2,2 difluoro; Pro-pane 2-amino, Propane-2-chloro; Propane-heptafluoro-1-nitro; Propane-heptafluoro-1-nitroso; Propane-perfluoro; Propene; Propyl-1,1,1,2,3,3-hexafluoro-2,3 dichloro; Propylene-1-chloro; Propylenechloro-(trans); Propylene-2-chloro; Propylene-3-fluoro; Propylene-perfluoro; Propyne; Propyne-3,3,3-trifluoro; Styrene-3-fluoro; Sulfur hexafluo-ride; Sulfur (di)-decafluoro(S2F10); Toluene-2,4-diamino; Trifluoroacetonitrile; Trifluoromethyl peroxide; Trifluorom-ethyl sulfide; Tungsten hexafluoride; Vinyl acetylene; Vinyl ether; Xenon; Nitrogen; air; and other ambient gases.

Perfluorocarbons are the preferred gases of the present invention, fluorine gas, perfluoromethane, perfluoroethane, perfluorobutane, perfluoropentane, perfluorohexane; even more preferrably perfluoroethane, perfluoropropane and per-fluorobutane; most preferrably perfluoropropane and per-fluorobutane as the more inert perfluorinated gases are less toxic.

Microspheres of the present invention include and are not limited to liposomes, lipid coatings, emulsions and poly-mers.

Lipids which may be used to create lipid microspheres include but are not limited to: lipids such as fatty acids, lysolipids, phosphatidylcholine with both saturated and unsaturated lipids including dioleoylphosphatidylcholine; dimyristoylphosphatidylcholine; dipentadecanoylphosphatidylcholine, dilauroylphosphatidylcholine, dioleoylphosphatidylcholine, dipalmitoylphosphatidylcholine; distearoylphosphatidyl-choline; phosphatidylethanolamines such as dioleoylphos-phatidylethanolamine; phosphatidylserine; phosphatidylg-lycerol; phosphatidylinositol, sphingolipids such as sphingomyelin; glycolipids such as ganglioside GM1 and GM2; glucolipids; sulfatides; glycosphingolipids; phospha-tidic acid; palmitic acid; stearic acid; arachidonic acid; oleic acid; lipids bearing polymers such as polyethyleneglycol, chitin, hyaluronic acid or polyvinylpyrrolidone; lipids bear-ing sulfonated mono-, di-, oligo- or polysaccharides; cholesterol, cholesterol sulfate and cholesterol hemisuccinate; tocopherol hemisuccinate, lipids with ether and ester-linked fatty acids, polymerized lipids, diacetyl phosphate, stearylamine, cardiolipin, phospholipids with short chain fatty acids of 6–8 carbons in length, synthetic phospholipids with asymmetric acyl chains (e.g., with one acyl chain of 6 carbons and another acyl chain of 12 carbons), 6-(5-cholesten-3β-yloxy)-1-thio-β-D-galactopyranoside, digalactosyldiglyceride, 6-(5-cholesten-3β-yloxy)hexyl-6-amino-6-deoxy-1-thio-β-D-galactopyranoside, 6-(5-cholesten-3β-yloxy)hexyl-6-amino-6-deoxyl-1-thio-α-D-mannopyranoside, 12-(((7'-diethylaminocoumarin-3-yl) carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoylphosphatidylethanolamine; 1,2-dioleoyl-sn-glycerol;1,2-dipalmitoyl-sn-3-succinylglycerol; 1,3-dipalmitoyl-2-succinylglycerol;1-hexadecyl-2-palmitoylglycerophosphoethanolamine; and palmitoylhomocysteine; and/or combinations thereof. The liposomes may be formed as monolayers or bilayers and may or may not have a coating.

Lipids bearing hydrophilic polymers such as polyethyleneglycol (PEG), including and not limited to PEG 2,000 MW, 5,000 MW, and PEG 8,000 MW, are particularly useful for improving the stability and size distribution of the gaseous precursor-containing liposomes. Various different mole ratios of PEGylated lipid, dipalmitoylphosphatidylethanolamine (DPPE) bearing PEG 5,000 MW, for example, are also useful; 8 mole percent DPPE is preferred. A preferred product which is highly useful for entrapping gaseous precursors contains 83 mole percent DPPC, 8 mole percent DPPE-PEG 5,000 MW and 5 mole percent dipalmitoylphosphatidic acid.

In addition, examples of compounds used to make mixed systems include, but by no means are limited to lauryltrimethylammonium bromide (dodecyl-), cetyltrimethylammonium bromide (hexadecyl-), myristyltrimethylammonium bromide (tetradecyl-), alkyldimethylbenzylammonium chloride (alkyl=C12, C14, C16), benzyldimethyldodecylammonium bromide/chloride, benzyldimethylhexadecylammonium bromide/chloride, benzyldimethyltetradecylammonium bromide/chloride, cetyldimethylethylammonium bromide/chloride, or cetylpyridinium bromide/chloride. Likewise perfluorocarbons such as pentafluoro octadecyl iodide, perfluorooctylbromide (PFOB), perfluorodecalin, perfluorododecalin, perfluorooctyliodide, perfluorotripropylamine, and perfluorotributylamine. The perfluorocarbons may be entrapped in liposomes or stabilized in emulsions as is well know in the art such as U.S. Pat. No. 4,865,836. The above examples of lipid suspensions may also be sterilized via autoclave without appreciable change in the size of the suspensions.

If desired, either anionic or cationic lipids may be used to bind anionic or cationic pharmaceuticals. Cationic lipids may be used to bind DNA and RNA analogues with in or on the surface of the gaseous precursor-filled microsphere. A variety of lipids such as DOTMA, N-[1-(2,3-dioleoyloxy) propyl]-N,N,N-trimethylammonium chloride; DOTAP, 1,2-dioleoyloxy-3-(trimethylammonio)propane; and DOTB, 1,2-dioleoyl-3-(4'-trimethyl-ammonio)butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine may also be used to construct the microspheres and afford binding of a negatively charged therapeutic, such as genetic material, to the outside of the microspheres. Additionally, negatively charged lipids may be used, for example, to bind positively charged therapeutic compounds. Phosphatidic acid, a negatively charged lipid, can also be used to complex DNA. This is highly surprising, as the positively charged lipids were heretofore thought to be generally necessary to bind genetic materials to liposomes. 5 to 10 mole percent phosphatidic acid in the liposomes improves the stability and size distribution of the gaseous precursor-filled liposomes.

Other useful lipids or combinations thereof apparent to those skilled in the art which are in keeping with the spirit of the present invention are also encompassed by the present invention. For example, carbohydrate-bearing lipids may be employed for in vivo targeting, as described in U.S. Pat. No. 4,310,505, the disclosures of which are hereby incorporated herein by reference in their entirety.

The most preferred lipids are phospholipids, preferably DPPC and DSPC, and most preferably DPPC.

Saturated and unsaturated fatty acids that may be used to generate gaseous precursor-filled microspheres preferably include, but are not limited to molecules that have between 12 carbon atoms and 22 carbon atoms in either linear or branched form. Examples of saturated fatty acids that may be used include, but are not limited to, lauric, myristic, palmitic, and stearic acids. Examples of unsaturated fatty acids that may be used include, but are not limited to, lauroleic, physeteric, myristoleic, palmitoleic, petroselinic, and oleic acids. Examples of branched fatty acids that may be used include, but are not limited to, isolauric, isomyristic, isopalmitic, and isostearic acids and isoprenoids.

Cationic polymers may be bound to the lipid layer through one or more alkyl groups or sterol groups which serve to anchor the cationic polymer into the lipid layer surrounding the gaseous precursor. Cationic polymers that may be used in this manner include, but are not limited to, polylysine and polyarginine, and their analogs such as polyhomoarginine or polyhomolysine. The positively charged groups of cationic lipids and cationic polymers, or perfluoroalkylated groups bearing cationic groups, for example, may be used to complex negatively charged molecules such as sugar phosphates on genetic material, thus binding the material to the surface of the gaseous precursor-filled lipid sphere. For example, cationic analogs of amphiphilic perfluoroalkylated bipyridines, as described in Garelli and Vierling, *Biochim. Biophys Acta*, 1992, 1127, 41–48, the disclosures of which are hereby incorporated herein by reference in their entirety, may be used. Alternatively, for example, negatively charged molecules may be bound directly to the head groups of the lipids via ester, amide, ether, disulfide or thioester linkages.

Bioactive materials, such as peptides or proteins, may be incorporated into the lipid layer provided the peptides have sufficient lipophilicity or may be derivatized with alkyl or sterol groups for attachment to the lipid layer. Negatively charged peptides may be attached, for example, using cationic lipids or polymers as described above.

One or more emulsifying or stabilizing agents may be included with the gaseous precursors to formulate the temperature activated gaseous precursor-filled microspheres. The purpose of these emulsifying/stabilizing agents is twofold. Firstly, these agents help to maintain the size of the gaseous precursor-filled microsphere. As noted above, the size of these microspheres will generally affect the size of the resultant gas-filled microspheres. Secondly the emulsifying and stabilizing agents may be used to coat or stabilize the microsphere which results from the precursor. Stabilization of contrast agent-containing microspheres is desirable to maximize the in vivo contrast effect. Although stabilization of the microsphere is preferred this is not an absolute requirement. Because the gas-filled microspheres resulting from these gaseous precursors are more stable than air, they may still be designed to provide useful contrast enhancement; for example, they pass through the pulmonary circulation following peripheral venous injection, even when not specifically stabilized by one or more coating or emulsifying agents. One or more coating or stabilizing agents is preferred however, as are flexible stabilizing materials. Gas microspheres stabilized by polysaccharides, gangliosides, and polymers are more effective than those stabilized by albumin and other proteins. Liposomes prepared using aliphatic compounds are preferred as microspheres stabilized with these compounds are much more flexible and stable to pressure changes.

Solutions of lipids or gaseous precursor-filled liposomes may be stabilized, for example, by the addition of a wide variety of viscosity modifiers, including, but not limited to carbohydrates and their phosphorylated and sulfonated derivatives; polyethers, preferably with molecular weight ranges between 400 and 8000; di- and trihydroxy alkanes and their polymers, preferably with molecular weight ranges between 800 and 8000. Glycerol propylene glycol, polyethylene glycol, polyvinyl pyrrolidone, and polyvinyl alcohol may also be useful as stabilizers in the present invention. Particles which are porous or semi-solid such as hydroxyapatite, metal oxides and coprecipitates of gels, e.g. hyaluronic acid with calcium may be used to formulate a center or nidus to stabilize the gaseous precursors.

Emulsifying and/or solubilizing agents may also be used in conjunction with lipids or liposomes. Such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan monooleate, sorbitan mono-palmitate, sorbitan monostearate, stearic acid, trolamine, and emulsifying wax. All lipids with perfluoro fatty acids as a component of the lipid in lieu of the saturated or unsaturated hydrocarbon fatty acids found in lipids of plant or animal origin may be used. Suspending and/or viscosity-increasing agents that may be used with lipid or liposome solutions include but are not limited to, acacia, agar, alginic acid, aluminum mono-stearate, bentonite, magma, carbomer 934P, carboxymethylcellulose, calcium and sodium and sodium 12, glycerol, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol, alginate, silicon dioxide, sodium alginate, tragacanth, and xanthum gum. A preferred product of the present invention incorporates lipid as a mixed solvent system in a ratio of 8:1:1 or 9:1:1 normal saline: glycerol:propylene glycol.

The gaseous precursor-filled liposomes of the present invention are preferably comprised of an impermeable material. Impermeable material is defined a material that does not permit the passage of a substantial amount of the contents of the liposome in typical storage conditions. Substantial is defined as greater than about 50% of the contents, the contents being both the gas as well as any other component encapsulated within the interior of the liposome, such as a therapeutic. Preferably, no more than about 25% of the gas is released, more preferably, no more than about 10% of the gas is released, and most preferably, no more than about 1% of the gas is released during storage and prior to administration to a patient.

At least in part, the gas impermeability of gaseous precursor-filled liposomes has been found to be related to the gel state to liquid crystalline state phase transition temperature. It is believed that, generally, the higher gel state to liquid crystalline state phase transition temperature, the more gas impermeable the liposomes are at a given temperature. See Table I above and Derek Marsh, *CRC Handbook of Lipid Bilayers* (CRC Press, Boca Raton, Fla. 1990), at p. 139 for main chain melting transitions of saturated diacyl-sn-glycero-3-phosphocholines. However, it should be noted that a lesser degree of energy can generally be used to release a therapeutic compound from gaseous precursor-filled liposomes composed of lipids with a lower gel state to liquid crystalline state phase transition temperature.

In certain preferred embodiments, the phase transition temperature of the lipid is greater than the internal body temperature of the patient to which they are administered. For example, lipids having a phase transition temperature greater than about 37° C. are preferred for administration to humans. In general, microspheres having a gel to liquid phase transition temperature greater than about 20° C. are adequate and those with a phase transition temperature greater than about 37° C. are preferred.

In preferred embodiments, the liposomes made by the methods of the present invention are stable, stability being defined as resistance to rupture from the time of formation until the application of ultrasound. The lipids used to construct the microspheres may be chosen for stability. For example, gaseous precursor-filled liposomes composed of DSPC (distearoylphosphatidylcholine) are more stable than gaseous precursor-filled liposomes composed of DPPC (dipalmitoylphosphatidylcholine) and that these in turn are more stable than gaseous precursor-filled liposomes composed of egg phosphatidylcholine (EPC). Preferably, no more than about 50% of the liposomes rupture from the time of formation until the application of ultrasound, more preferably, no more than about 25% of the liposomes rupture, even more preferably, no more than about 10% of the liposomes, and most preferably, no more than about 1% of the liposomes.

The subject liposomes tend to have greater gas impermeability and stability during storage than other gas-filled liposomes produced via known procedures such as pressurization or other techniques. At 72 hours after formation, for example, conventionally prepared liposomes often are essentially devoid of gas, the gas having diffused out of the liposomes and/or the liposomes having ruptured and/or fused, resulting in a concomitant loss in reflectivity. In comparison, gaseous precursor-filled liposomes of the present invention maintained in aqueous solution generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months, or even two years.

In addition, it has been found that the gaseous precursor-filled liposomes of the present invention can be stabilized with lipids covalently linked to polymers of polyethylene glycol, commonly referred to as PEGylated lipids. It has also been found that the incorporation of at least a small amount of negatively charged lipid into any liposome membrane, although not required, is beneficial to providing liposomes that do not have a propensity to rupture by aggregation. By at least a small amount, it is meant about 1 to about 10 mole percent of the total lipid. Suitable negatively charged lipids, or lipids bearing a net negative charge, will be readily apparent to those skilled in the art, and include, for example, phosphatidylserine, phosphatidylglycerol, phosphatidic acid, and fatty acids. Liposomes prepared from dipalmitoylphosphatidylcholine are most preferred as they are selected for their ability to rupture on application of resonant frequency ultrasound, radiofrequency energy, (e.g. microwave), and/or echogenicity in addition to their stability during delivery.

Further, the liposomes of the invention are preferably sufficiently stable in the vasculature such that they withstand recirculation. The gaseous precursor-filled liposomes may be coated such that uptake by the reticuloendothelial system is minimized. Useful coatings include, for example, gangliosides, glucuronide, galacturonate, guluronate, polyethyleneglycol, polypropylene glycol, polyvinylpyrrolidone, polyvinylalcohol, dextran, starch, phosphorylated and sulfonated mono, di, tri, oligo and polysaccharides and albumin. The liposomes may also be coated for purposes such as evading recognition by the immune system.

The lipid used is also preferably flexible. Flexibility, as defined in the context of gaseous precursor-filled liposomes, is the ability of a structure to alter its shape, for example, in order to pass through an opening having a size smaller than the liposome.

Provided that the circulation half-life of the liposomes is sufficiently long, the liposomes will generally pass through the target tissue while passing through the body. Thus, by focusing the sound waves on the selected tissue to be treated, the therapeutic will be released locally in the target tissue. As a further aid to targeting, antibodies, carbohydrates, peptides, glycopeptides, glycolipids, lectins, and synthetic and natural polymers may also be incorporated into the surface of the liposomes. Other aids for targeting include polymers such as polyethyleneglycol, polyvinylpyrrolidone, and polvinylalcohol, which may be incorporated onto the surface via alkylation, acylation, sterol groups or derivatized head groups of phospholipids such as dioleoylphosphatidylethanolamine (DOPE), dipalmitoylphosphatidylethanolamine (DPPE), or distearoylphosphatidylethanolamine (DSPE). Peptides, antibodies, lectins, glycopeptides, oligonucleotides, and glycoconjugates may also be incorporated onto the surfaces of the gaseous precursor-filled lipid spheres.

In certain preferred embodiments, as an aid to the gaseous precursor instillation process as well as to maintain the stability of the gaseous precursor-filled liposomes, for example, emulsifiers may be added to the lipid. Examples of emulsifiers include, but are not limited to, glycerol, cetyl alcohol, sorbitol, polyvinyl alcohol, polypropylene glycol, propylene glycol, ethyl alcohol, sodium lauryl sulfate, Laureth 23, polysorbates (all units), all saturated and unsaturated fatty acids, triethanolamine, Tween 20, tween 40, Tween 60, tween 80, Polysorbate 20, Polysorbate 40, Polysorbate 60, and Polysorbate 80.

For storage prior to use, the liposomes of the present invention may be suspended in an aqueous solution, such as a saline solution (for example, a phosphate buffered saline solution), or simply water, and stored preferably at a temperature of between about 2° C. and about 10° C., preferably at about 4° C. Preferably, the water is sterile.

Typical storage conditions are, for example, a non-degassed aqueous solution of 0.9% NaCl maintained at 4° C. for 48 hours. The temperature of storage is preferably below the gel state to liquid crystalline state phase transition temperature of the material forming the liposomes.

Most preferably, the liposomes are stored in an isotonic saline solution, although, if desired, the saline solution may be hypotonic (e.g., about 0.3 to about 0.5% NaCl). The solution also may be buffered, if desired, to provide a pH range of about pH 5 to about pH 7.4. Suitable buffers include, but are not limited to, acetate, citrate, phosphate, bicarbonate, and phosphate-buffered saline, 5% dextrose, and physiological saline (normal saline).

Bacteriostatic agents may also be included with the liposomes to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid.

By "gas-filled", as used herein, it is meant liposomes having an interior volume that is at least about 10% gas, preferably at least about 25% gas, more preferably at least about 50% gas, even more preferably at least about 75% gas, and most preferably at least about 90% gas. It will be understood by one skilled in the art, once armed with the present disclosure, that a gaseous precursor may also be used, followed by activation to form a gas.

Various biocompatible gases may be employed in the gas-filled liposomes of the present invention. Such gases include air, nitrogen, carbon dioxide, oxygen, argon, fluorine, xenon, neon, helium, or any and all combinations thereof. Other suitable gases will be apparent to those skilled in the art once armed with the present disclosure. In addition to the gaseous precursors disclosed herein, the precursors may be co-entrapped with other gases. For example, during the transition from the gaseous precursor to a gas in an enclosed environment containing ambient gas (as air), the two gases may mix and upon agitation and formation of microspheres, the gaseous content of the microspheres results in a mixture of two or more gases, dependent upon the densities of the gases mixed.

The size of the liposomes of the present invention will depend upon the intended use. With the smaller liposomes, resonant frequency ultrasound will generally be higher than for the larger liposomes. Sizing also serves to modulate resultant liposomal biodistribution and clearance. In addition to filtration, the size of the liposomes can be adjusted, if desired, by procedures known to one skilled in the art, such as extrusion, sonication, homogenization, the use of a laminar stream of a core of liquid introduced into an immiscible sheath of liquid. See, for example, U.S. Pat. No. 4,728,578; U.K. Patent Application GB 2193095 A; U.S. Pat. No. 4,728,575; U.S. Pat. No. 4,737,323; International Application PCT/US85/01161; Mayer et al., *Biochimica et Biophysica Acta* 1986, 858, 161–168; Hope et al., *Biochimica et Biophysica Acta* 1985, 812, 55–65; U.S. Pat. No. 4,533,254; Mayhew et al., *Methods in Enzymology* 1987, 149, 64–77; Mayhew et al., *Biochimica et Biophysica Acta* 1984, 755, 169–74; Cheng et al, *Investigative Radiology* 1987, 22, 47–55; PCT/US89/05040; U.S. Pat. No. 4,162,282; U.S. Pat. No. 4,310,505; U.S. Pat. No. 4,921,706; and *Liposomes Technology*, Gregoriadis, G., ed., Vol. I, pp. 29–37, 51–67 and 79–108 (CRC Press Inc, Boca Raton, Fla., 1984). The disclosures of each of the foregoing patents, publications and patent applications are incorporated by reference herein, in their entirety. Extrusion under pressure through pores of defined size is a preferred method of adjusting the size of the liposomes.

Since liposome size influences biodistribution, different size liposomes may be selected for various purposes. For example, for intravascular application, the preferred size range is a mean outside diameter between about 30 nanometers and about 10 microns, with the preferable mean outside diameter being about 5 microns.

More specifically, for intravascular application, the size of the liposomes is preferably about 10 $\mu$m or less in mean outside diameter, and preferably less than about 7 $\mu$m, and more preferably no smaller than about 5 nanometers in mean outside diameter. Preferably, the liposomes are no smaller than about 30 nanometers in mean outside diameter.

To provide therapeutic delivery to organs such as the liver and to allow differentiation of tumor from normal tissue, smaller liposomes, between about 30 nanometers and about 100 nanometers in mean outside diameter, are preferred.

For embolization of a tissue such as the kidney or the lung, the liposomes are preferably less than about 200 microns in mean outside diameter.

For intranasal, intrarectal or topical administration, the microspheres are preferably less than about 100 microns in mean outside diameter.

Large liposomes, e.g., between 1 and 10 microns in size, will generally be confined to the intravascular space until they are cleared by phagocytic elements lining the vessels, such as the macrophages and Kuppfer cells lining capillary sinusoids. For passage to the cells beyond the sinusoids, smaller liposomes, for example, less than about a micron in mean outside diameter, e.g., less than about 300 nanometers in size, may be utilized.

The route of administration of the liposomes will vary depending on the intended use. As one skilled in the art would recognize, administration of therapeutic delivery systems of the present invention may be carried out in various fashions, such as intravascularly, intralymphatically, parenterally, subcutaneously, intramuscularly, intranasally, intrarectally, intraperitoneally, interstitially, into the airways via nebulizer, hyperbarically, orally, topically, or intratumorly, using a variety of dosage forms. One preferred route of administration is intravascularly. For intravascular use, the therapeutic delivery system is generally injected intravenously, but may be injected intraarterially as well. The liposomes of the invention may also be injected interstitially or into any body cavity.

The delivery of therapeutics from the liposomes of the present invention using ultrasound is best accomplished for tissues-which have a good acoustic window for the transmission of ultrasonic energy. This is the case for most tissues in the body such as muscle, the heart, the liver and most other vital structures. In the brain, in order to direct the ultrasonic energy past the skull a surgical window may be necessary. For body parts without an acoustic window, e.g. through bone, radiofrequency or microwave energy is preferred.

Additionally, the invention is especially useful in delivering therapeutics to a patient's lungs. Gaseous precursor-filled liposomes of the present invention are lighter than, for example, conventional liquid-filled liposomes which generally deposit in the central proximal airway rather than reaching the periphery of the lungs. It is therefore believed that the gaseous precursor-filled liposomes of the present invention may improve delivery of a therapeutic compound to the periphery of the lungs, including the terminal airways and the alveoli. For application to the lungs, the gaseous precursor-filled liposomes may be applied through nebulization, for example.

2 cc of liposomes (lipid=83% DPPC/8% DPPE-PEG 5,000/5% DPPA) entrapping air was placed in a nebulizer and nebulized. The resulting liposomes post nebulization, were around 1 to 2 microns in size and were shown to float in the air. These size particles appear ideal for delivering drugs, peptides, genetic materials and other therapeutic compounds into the far reaches of the lung (i.e. terminal airways and alveoli). Because the gas filled liposomes are almost as light as air, much lighter than conventional water filled liposomes, they float longer in the air, and as such are better for delivering compounds into the distal lung. When DNA is added to these liposomes, it is readily adsorbed or bound to the liposomes. Thus, liposomes and microspheres filled by gas and gaseous precursors hold vast potential for pulmonary drug delivery.

In applications such as the targeting of the lungs, which are lined with lipids, the therapeutic may be released upon aggregation of the gaseous precursor-filled liposome with the lipids lining the targeted tissue. Additionally, the gaseous precursor-filled liposomes may burst after administration without the use of ultrasound. Thus, ultrasound need not be applied to release the drug in the above type of administration.

Further, the gaseous precursor-filled liposomes of the invention are especially useful for therapeutics that may be degraded in aqueous media or upon exposure to oxygen and/or atmospheric air. For example, the liposomes may be filled with an inert gas such as nitrogen or argon, for use with labile therapeutic compounds. Additionally, the gaseous precursor-filled liposomes may be filled with an inert gas and used to encapsulate a labile therapeutic for use in a region of a patient that would normally cause the therapeutic to be exposed to atmospheric air, such as cutaneous and ophthalmic applications.

The gaseous precursor-filled liposomes are also especially useful for transcutaneous delivery, such as a patch delivery system. The use of rupturing ultrasound may increase transdermal delivery of therapeutic compounds. Further, a mechanism may be used to monitor and modulate drug delivery. For example, diagnostic ultrasound may be used to visually monitor the bursting of the gaseous precursor-filled liposomes and modulate drug delivery and/or a hydrophone may be used to detect the sound of the bursting of the gaseous precursor-filled liposomes and modulate drug delivery.

In preferred embodiments, the gas-filled liposomes are administered in a vehicle as individual particles, as opposed to being embedded in a polymeric matrix for the purposes of controlled release.

For in vitro use, such as cell culture applications, the gaseous precursor-filled liposomes may be added to the cells in cultures and then incubated. Subsequently sonic energy, microwave, or thermal energy (e.g. simple heating) can be applied to the culture media containing the cells and liposomes.

Generally, the therapeutic delivery systems of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may also be buffered, if desired, to provide a pH range of about pH 5 to about pH 7.4. In addition, dextrose may be preferably included in the media. Further solutions that may be used for administration of gaseous precursor-filled liposomes include, but are not limited to almond oil, corn oil, cottonseed oil, ethyl oleate, isopropyl myristate, isopropyl palmitate, mineral oil, myristyl alcohol, octyl-dodecanol, olive oil, peanut oil, persic oil, sesame oil, soybean oil, squalene, myristyl oleate, cetyl oleate, myristyl palmitate, as well as other saturated and unsaturated alkyl chain alcohols (C=2–22) esterified to alkyl chain fatty acids (C=2–22).

The useful dosage of gaseous precursor-filled microspheres to be administered and the mode of administration will vary depending upon the age, weight, and mammal to be treated, and the particular application (therapeutic/diagnostic) intended. Typically, dosage is initiated at lower levels and increased until the desired therapeutic effect is achieved.

For use in ultrasonic imaging, preferably, the liposomes of the invention possess a reflectivity of greater than 2 dB, more preferably between about 4 dB and about 20 dB. Within these ranges, the highest reflectivity for the liposomes of the invention is exhibited by the larger liposomes, by higher concentrations of liposomes, and/or when higher ultrasound frequencies are employed.

For therapeutic drug delivery, the rupturing of the therapeutic containing liposomes of the invention is surprisingly easily carried out by applying ultrasound of a certain frequency to the region of the patient where therapy is desired, after the liposomes have been administered to or have otherwise reached that region. Specifically, it has been unexpectedly found that when ultrasound is applied at a frequency corresponding to the peak resonant frequency of the therapeutic containing gaseous precursor-filled liposomes, the liposomes will rupture and release their contents.

The peak resonant frequency can be determined either in vivo or in vitro, but preferably in vivo, by exposing the liposomes to ultrasound, receiving the reflected resonant frequency signals and analyzing the spectrum of signals received to determine the peak, using conventional means. The peak, as so determined, corresponds to the peak resonant frequency (or second harmonic, as it is sometimes termed).

Preferably, the liposomes of the invention have a peak resonant frequency of between about 0.5 mHz and about 10 mHz. of course, the peak resonant frequency of the gaseous precursor-filled liposomes of the invention will vary depending on the outside diameter and, to some extent, the elasticity or flexibility of the liposomes, with the larger and more elastic or flexible liposomes having a lower resonant frequency than the smaller and less elastic or flexible liposomes.

The therapeutic-containing gaseous precursor-filled liposomes will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and therapeutic release is improved, appreciable tissue heating does not generally occur (frequently no increase in temperature above about 2° C.), and less overall energy is required. Thus, application of ultrasound at the peak resonant frequency, while not required, is most preferred.

For diagnostic or therapeutic ultrasound, any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the liposome is visualized on ultrasound (for diagnostic ultrasound applications) or ruptures (for therapeutic ultrasound applications).

Although application of the various principles will be readily apparent to one skilled in the art, once armed with the present disclosure, by way of general guidance, for gaseous precursor-filled liposomes of about 1.5 to about 10 microns in mean outside diameter, the resonant frequency will generally be in the range of about 1 to about 10 megahertz. By adjusting the focal zone to the center of the target tissue (e.g., the tumor) the gaseous precursor-filled liposomes can be visualized under real time ultrasound as they accumulate within the target tissue. Using the 7.5 megahertz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of therapeutic from the gaseous precursor-filled liposomes, but much greater release can be accomplished by using higher power.

By switching the transducer to the doppler mode, higher power outputs are available, up to 2.5 watts per cm$^2$ from the same transducer. With the machine operating in doppler mode, the power can be delivered to a selected focal zone within the target tissue and the gaseous precursor-filled liposomes can be made to release their therapeutics. Selecting the transducer to match the resonant frequency of the gaseous precursor-filled liposomes will make this process of therapeutic release even more efficient.

For larger diameter gaseous precursor-filled liposomes, e.g., greater than 3 microns in mean outside diameter, a lower frequency transducer may be more effective in accomplishing therapeutic release. For example, a lower frequency transducer of 3.5 megahertz (20 mm curved array model) may be selected to correspond to the resonant frequency of the gaseous precursor-filled liposomes. Using this transducer, 101.6 milliwatts per cm$^2$ may be delivered to the focal spot, and switching to doppler mode will increase the power output (SPTA) to 1.02 watts per cm$^2$.

To use the phenomenon of cavitation to release and/or activate the drugs/prodrugs within the gaseous precursor-filled liposomes, lower frequency energies may be used, as cavitation occurs more effectively at lower frequencies. Using a 0.757 megahertz transducer driven with higher voltages (as high as 300 volts) cavitation of solutions of gaseous precursor-filled liposomes will occur at thresholds of about 5.2 atmospheres.

Table III shows the ranges of energies transmitted to tissues from diagnostic ultrasound on commonly used instruments such as the Piconics Inc. (Tyngsboro, Mass.)

Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler. In general, these ranges of energies employed in pulse repetition are useful for diagnosis and monitoring the gas-filled liposomes but are insufficient to rupture the gas-filled liposomes of the present invention.

TABLE III

Power and Intensities Produced by Diagnostic Equipment*

| Pulse repetition rate (Hz) | Total ultrasonic power output P (mW) | Average Intensity at transducer face $I_{TD}$ (W/m$^2$) |
|---|---|---|
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med. & Biol. 1978, 3, 341–350, the disclosures of which are hereby incorporated herein by reference in their entirety.

Higher energy ultrasound such as commonly employed in therapeutic ultrasound equipment is preferred for activation of the therapeutic containing gaseous precursor-filled liposomes. In general, therapeutic ultrasound machines employ as much as 50% to 100% duty cycles dependent upon the area of tissue to be heated by ultrasound. Areas with larger amounts of muscle mass (i.e., backs, thighs) and highly vascularized tissues such as heart may require the larger duty cycle, e.g., 100%.

In diagnostic ultrasound, one or several pulses of sound are used and the machine pauses between pulses to receive the reflected sonic signals. The limited number of pulses used in diagnostic ultrasound limits the effective energy which is delivered to the tissue which is being imaged.

In therapeutic ultrasound, continuous wave ultrasound is used to deliver higher energy levels. In using the liposomes of the present invention, the sound energy may be pulsed, but continuous wave ultrasound is preferred. If pulsing is employed, the sound will preferably be pulsed in echo train lengths of at least about 8 and preferably at least about 20 pulses at a time.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the liposomes and rupturing to provide local delivery of therapeutics.

The frequency of the sound used may vary from about 0.025 to about 100 megahertz. Frequency ranges between about 0.75 and about 3 megahertz are preferred and frequencies between about 1 and about 2 megahertz are most preferred. Commonly used therapeutic frequencies of about 0.75 to about 1.5 megahertz may be used. Commonly used diagnostic frequencies of about 3 to about 7.5 megahertz may also be used. For very small liposomes, e.g., below 0.5 micron in mean outside diameter, higher frequencies of sound may be preferred as these smaller liposomes will absorb sonic energy more effectively at higher frequencies of sound. When very high frequencies are used, e.g., over 10 megahertz, the sonic energy will generally have limited depth penetration into fluids and tissues. External application may be preferred for the skin and other superficial tissues, but for deep structures, the application of sonic energy via interstitial probes or intravascular ultrasound catheters may be preferred.

Where the gaseous precursor-filled liposomes are used for therapeutic delivery, the therapeutic compound to be delivered may be embedded within the wall of the liposome, encapsulated in the liposome and/or attached to the liposome, as desired. The phrase "attached to" or variations thereof, as used herein in connection with the location of the therapeutic compound, means that the therapeutic compound is linked in some manner to the inside and/or the outside wall of the microsphere, such as through a covalent or ionic bond or other means of chemical or electrochemical linkage or interaction. The phrase "encapsulated in variations thereof" as used in connection with the location of the therapeutic compound denotes that the therapeutic compound is located in the internal microsphere void. The phrase "embedded within" or variations thereof as used in connection with the location of the therapeutic compound, signifies the positioning of the therapeutic compound within the microsphere wall. The phrase "comprising a therapeutic" denotes all of the varying types of therapeutic positioning in connection with the microsphere. Thus, the therapeutic can be positioned variably, such as, for example, entrapped within the internal void of the gaseous precursor-filled microsphere, situated between the gaseous precursor and the internal wall of the gaseous precursor-filled microsphere, incorporated onto the external surface of the gaseous precursor-filled microsphere and/or enmeshed within the microsphere structure itself.

Any of a variety of therapeutics may be encapsulated in the liposomes. By therapeutic, as used herein, it is meant an agent having beneficial effect on the patient. As used herein, the term therapeutic is synonymous with the terms contrast agent and/or drug.

Examples of drugs that may be delivered with gaseous precursor-filled liposomes may contain for drug delivery purposes, but by no means is limited to; hormone products such as, vasopressin and oxytocin and their derivatives, glucagon, and thyroid agents as iodine products and antithyroid agents; cardiovascular products as chelating agents and mercurial diuretics and cardiac glycosides; respiratory products as xanthine derivatives (theophylline & aminophylline); anti-infectives as aminoglycosides, antifungals (amphotericin), penicillin and cephalosporin antibiotics, antiviral agents as Zidovudine, Ribavirin, Amantadine, Vidarabine, and Acyclovir, anti-helmintics, antimalarials, and antituberculous drugs; biologicals as immune serums, antitoxins and antivenins, rabies prophylaxis products, bacterial vaccines, viral vaccines, toxoids; antineoplastics as nitrosureas, nitrogen mustards, antimetabolites (fluorouracil, hormones as progestins and estrogens and antiestrogens; antibiotics as Dactinomycin; mitotic inhibitors as Etoposide and the Vinca alkaloids, Radiopharmaceuticals as radioactive iodine and phosphorus products; as well as Interferon, hydroxyurea, procarbazine, Dacarbazine, Mitotane, Asparaginase and cyclosporins.

Genetic and bioactive materials may be incorporated into the internal gaseous precursor-filled space of these liposomes during the gaseous precursor installation process or into or onto the lipid membranes of these particles. Incorporation onto the surface of these particles is preferred. Genetic materials and bioactive products with a high octanol/water partition coefficient may be incorporated directly into the lipid layer surrounding the gaseous precursor but incorporation onto the surface of the gaseous precursor-filled lipid spheres is more preferred. To accomplish this, groups capable of binding genetic materials or bioactive materials are generally incorporated into the lipid layers which will then bind these materials. In the case of genetic materials (DNA, RNA, both single stranded and double stranded and antisense and sense oligonucleotides) this is readily accomplished through the use of cationic lipids or cationic polymers which may be incorporated into the dried lipid starting materials.

It is the surprising discovery of the invention that liposomes, gas-filled and gas precursor-filled, when produced with phosphatidic acid, e.g. dipalmitoylphosphatidic acid in molar amounts in excess of 5 mole % and preferably about 10 mole %, function as highly effective binders of genetic material. Such liposomes bind DNA avidly. This is surprising since positively charged liposomes were heretofore recognized as most useful for binding DNA. Liposomes with 5 mole % to 10 mole % DPPA function as highly effective gas and gaseous precursor retaining structures. Compositions incorporating phosphatidic acid are more robust for diagnostic ultrasound and useful for carrying DNA as well as other pharmaceuticals.

It is believed that nanoparticles, microparticles, and emulsions of certain precursors are particularly effective at accumulating in ischemic and diseased tissue. Such precursors can be used for detecting ischemic and diseased tissue via ultrasound and also for delivering drugs to these tissues. By co-entrapping drugs with the emulsions or nanoparticles comprising the gaseous precursors said drugs can then be delivered to the diseased tissues. For example, emulsions of, sulfur hexafluoride, hesafluoropropylene, bromochlorofluoromethane, octafluoropropane, 1,1dichloro, fluoro ethane, hexafluoroethane, hesafluoro-2-butyne, perfluoropentane, perfluorobutane, octafluoro-2-butene or hexafluorobuta-1,3-diene or octafluorocyclopentene (27° C.) can be used to deliver drugs such as cardiac glycosides, angiogenic factors and vasoactive compounds to ischemic regions of the myocardium. Similarly, emulsions of the above precursors may also be used to deliver antisense DNA or chemotherapeutics to tumors. It is postulated that subtle changes in temperature, pH and oxygen tension are responsible for the accumulation of certain precursors preferentially by diseased and ischemic tissues. These precursors can be used as a delivery vehicle or in ultrasound for drug delivery.

Suitable therapeutics include, but are not limited to paramagnetic gases, such as atmospheric air, which contains traces of oxygen 17; paramagnetic ions such as $Mn^{+2}$, $Gd^{+2}$, $Fe^{+3}$; iron oxides or magnetite ($Fe_3O_4$) and may thus be used as susceptibility contrast agents for magnetic resonance imaging (MRI), radioopaque metal ions, such as iodine, barium, bromine, or tungsten, for use as x-ray contrast agents, gases from quadrupolar nuclei, may have potential for use as Magnetic Resonance contrast agents, antineoplastic agents, such as platinum compounds (e.g., spiroplatin, cisplatin, and carboplatin), methotrexate, fluorouracil, adriamycin, taxol, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, and arabinosyl, hydroxyurea, procarbazine, and dacarbazine; mitotic inhibitors such as etoposide and the vinca alkaloids, radiopharmaceuticals such as radioactive iodine and phosphorus products; hormones such as progestins, estrogens and antiestrogens; anti-helmintics, antimalarials, and antituberculosis drugs; biologicals such as immune serums, antitoxins and antivenins; rabies prophylaxis products; bacterial vaccines; viral vaccines; aminoglycosides; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), subunits of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-FC), miconazole, amphotericin B, ricin, cyclosporins, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone terbutate, prednisone, triamcinolone, triamcinolone acetonide, triamcinolone diacetate, triamcinolone hexacetonide and fludrocortisone acetate, oxytocin, vassopressin, and their derivatives; vitamins such as cyanocobalamin neinoic acid, retinoids and derivatives such as retinol palmitate, and α-tocopherol; peptides, such as manganese super oxide dimutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin and vidarabine monohydrate (adenine arabinoside, ara-A); antianginals such as diltiazem, nifedipine, verapamil, erythrityl tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin, including penicillin G, penicillin V, ticarcillin rifampin and tetracycline; antiinflammatories such as difunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In certain preferred embodiments, the therapeutic is a monoclonal antibody, such as a monoclonal antibody capable of binding to melanoma antigen.

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate, phosphoroamidate, and phosphorodithioate oligodeoxynucleotides. Additionally, the genetic material may be combined, for example, with proteins or other polymers.

Examples of genetic therapeutics that may be applied using the liposomes of the present invention include DNA encoding at least a portion of an HLA gene, DNA encoding at least a portion of dystrophin, DNA encoding at least a portion of CFTR, DNA encoding at least a portion of IL-2, DNA encoding at least a portion of TNF, an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, Thompson, L., *Science*, 1992, 258, 744–746.

If desired, more than one therapeutic may be applied using the liposomes. For example, a single liposome may contain more than one therapeutic or liposomes containing different therapeutics may be co-administered. By way of example, a monoclonal antibody capable of binding to melanoma antigen and an oligonucleotide encoding at least a portion of IL-2 may be administered at the same time. The phrase "at least a portion of," as used herein, means that the entire gene need not be represented by the oligonucleotide, so long as the portion of the gene represented provides an effective block to gene expression.

Similarly, prodrugs may be encapsulated in the liposomes, and are included within the ambit of the term therapeutic, as used herein. Prodrugs are well known in the art and include inactive drug precursors which, when exposed to high temperature, metabolizing enzymes, cavitation and/or pressure, in the presence of oxygen or otherwise, or when released from the liposomes, will form active drugs. Such prodrugs can be activated from, or released from, gas-filled lipid spheres in the method of the invention, upon the application of ultrasound or radiofrequency microwave energy to the prodrug-containing liposomes with the resultant cavitation, heating, pressure, and/or release from the liposomes. Suitable prodrugs will be apparent to those skilled in the art, and are described, for example, in Sinkula et al., *J. Pharm. Sci.* 1975, 64, 181–210, the disclosure of which are hereby incorporated herein by reference in its entirety.

Prodrugs, for example, may comprise inactive forms of the active drugs wherein a chemical group is present on the prodrug which renders it inactive and/or confers solubility or some other property to the drug. In this form, the prodrugs are generally inactive, but once the chemical group has been cleaved from the prodrug, by heat, cavitation, pressure, and/or by enzymes in the surrounding environment or otherwise, the active drug is generated. Such prodrugs are well described in the art, and comprise a wide variety of drugs bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and β-glucoside.

Examples of drugs with the parent molecule and the reversible modification or linkage are as follows: convallatoxin with ketals, hydantoin with alkyl esters, chlorphenesin with glycine or alanine esters, acetaminophen with caffeine complex, acetylsalicylic acid with THAM salt, acetylsalicylic acid with acetamidophenyl ester, naloxone with sulfate ester, 15-methylprostaglandin $F_2$. with methyl ester, procaine with polyethylene glycol, erythromycin with alkyl esters, clindamycin with alkyl esters or phosphate esters, tetracycline with betaine salts, 7-acylaminocephalosporins with ring-substituted acyloxybenzyl esters, nandrolone with phenylproprionate decanoate esters, estradiol with enol ether acetal, methylprednisolone with acetate esters, testosterone with n-acetylglucosaminide glucosiduronate (trimethylsilyl) ether, cortisol or prednisolone or dexamethasone with 21-phosphate esters.

Prodrugs may also be designed as reversible drug derivatives and utilized as modifiers to enhance drug transport to site-specific tissues. Examples of parent molecules with reversible modifications or linkages to influence transport to a site specific tissue and for enhanced therapeutic effect include isocyanate with haloalkyl nitrosurea, testosterone with propionate ester, methotrexate (3-5'-dichloromethotrexate) with dialkyl esters, cytosine arabinoside with 5'-acylate, nitrogen mustard (2,2'-dichloro-N- methyldiethylamine), nitrogen mustard with aminomethyl tetracycline, nitrogen mustard with cholesterol or estradiol or dehydroepiandrosterone esters and nitrogen mustard with azobenzene.

As one skilled in the art would recognize, a particular chemical group to modify a given drug may be selected to influence the partitioning of the drug into either the membrane or the internal space of the liposomes. The bond selected to link the chemical group to the drug may be selected to have the desired rate of metabolism, e.g., hydrolysis in the case of ester bonds in the presence of serum esterases after release from the gaseous precursor-filled liposomes. Additionally, the particular chemical group may be selected to influence the biodistribution of the drug employed in the gaseous precursor-filled drug carrying liposome invention, e.g., N,N-bis(2-chloroethyl) phosphorodiamidic acid with cyclic phosphoramide for ovarian adenocarcinoma.

Additionally, the prodrugs employed within the gaseous precursor-filled liposbmes may be designed to contain reversible derivatives which are utilized as modifiers of duration of activity to provide, prolong or depot action effects. For example, nicotinic acid may be modified with dextran and carboxymethlydextran esters, streptomycin with alginic acid salt, dihydrostreptomycin with pamoate salt, cytarabine (ara-C) with 5'-adamantoate ester, ara-adenosine (ara-A) with 5-palmitate and 5'-benzoate esters, amphotericin B with methyl esters, testosterone with 17-β-alkyl esters, estradiol with formate ester, prostaglandin with 2-(4-imidazolyl)ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the gaseous precursor-filled prodrug bearing liposomes.

In addition, compounds which are generally thermally labile may be utilized to create toxic free radical compounds. Compounds with azolinkages, peroxides and disulfide linkages which decompose with high temperature are preferred. With this form of prodrug, azo, peroxide or disulfide bond containing compounds are activated by cavitation and/or increased heating caused by the interaction of high energy sound with the gaseous precursor-filled liposomes to create cascades of free radicals from these prodrugs entrapped therein. A wide variety of drugs or chemicals may constitute these prodrugs, such as azo compounds, the general structure of such compounds being R—N=N—R, wherein R is a hydrocarbon chain, where the double bond between the two nitrogen atoms may react to create free radical products in vivo.

Exemplary drugs or compounds which may be used to create free radical products include azo containing compounds such as azobenzene, 2,2'-azobisisobutyronitrile, azodicarbonamide, azolitmin, azomycin, azosemide, azosulfamide, azoxybenzene, aztreonam, sudan III, sulfachrysoidine, sulfamidochrysoidine and sulfasalazine, compounds containing disulfide bonds such as sulbentine, thiamine disulfide, thiolutin, thiram, compounds containing peroxides such as hydrogen peroxide and benzoylperoxide, 2,2'-azobisisobutyronitrile, 2,2'-azobis(2-amidopropane) dihydrochloride, and 2,2'-azobis(2,4-dimethylvaleronitrile).

A gaseous precursor-filled liposome filled with oxygen gas should create extensive free radicals with cavitation. Also, metal ions from the transition series, especially manganese, iron and copper can increase the rate of formation of reactive oxygen intermediates from oxygen. By encapsulating metal ions within the liposomes, the formation of free radicals in vivo can be increased. These metal ions may be incorporated into thealiposomes as free salts, as complexes, e.g., with EDTA, DTPA, DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gaseous precursor-filled liposomes to create free radicals on thermal stimulation.

By way of an example of the use of prodrugs, an acylated chemical group may be bound to a drug via an ester linkage which would readily cleave in vivo by enzymatic action in serum. The acylated prodrug is incorporated into the gaseous precursor-filled liposome of the invention. The derivatives, in addition to hydrocarbon and substituted hydrocarbon alkyl groups, may also be composed of halo substituted and perhalo substituted groups as perfluoroalkyl groups. Perfluoroalkyl groups should possess the ability to stabilize the emulsion. When the gaseous precursor-filled liposome is popped by the sonic pulse from the ultrasound, the prodrug encapsulated by the liposome will then be exposed to the serum. The ester linkage is then cleaved by esterases in the serum, thereby generating the drug.

Similarly, ultrasound may be utilized not only to rupture the gaseous precursor-filled liposome, but also to cause thermal effects which may increase the rate of the chemical cleavage and the release of the active drug from the prodrug.

The liposomes may also be designed so that there is a symmetric or an asymmetric distribution of the drug both inside and outside of the liposome.

The particular chemical structure of the therapeutics may be selected or modified to achieve desired solubility such that the therapeutic may either be encapsulated within the internal gaseous precursor-filled space of the liposome, attached to the liposome or enmeshed in the liposome. The surface-bound therapeutic may bear one or more acyl chains such that, when the bubble is popped or heated or ruptured via cavitation, the acylated therapeutic may then leave the surface and/or the therapeutic may be cleaved from the acyl chains chemical group. Similarly, other therapeutics may be formulated with a hydrophobic group which is aromatic or sterol in structure to incorporate into the surface of the liposome.

The present invention is further described in the following examples, which illustrate the preparation and testing of the gaseous precursor-filled liposomes. Examples 1–5, and 22–24 are actual; Examples 6–21 are prophetic. The following examples should not be construed as limiting the scope of the appended claims.

EXAMPLE 1

Preparation of Gas-Filled Lipid Spheres from Perfluorobutane

Gaseous precursor-containing liposomes were prepared using perfluorobutane (Pfaltz and Bauer, Waterbury, Conn.) as follows: A 5 mL solution of lipid, 5 mg per ml, lipid=87 mole percent DPPC, 8 mole percent DPPE-PEG 5,000, 5 mole percent dipalmitoylphosphatidic acid (all lipids from Avanti Polar Lipids, Alabaster, Ala.), in 8:1:1 normal saline:glycerol:propylene glycol, was placed in a glass bottle with a rubber stopper (volume of bottle=15.8 ml). Air was evacuated from the bottle using a vacuum pump, Model Welch 2-Stage DirecTorr Pump (VWR Scientific, Cerritos, Calif.) by connecting the hose to the bottle through a 18 gauge needle which perforated the rubber stopper. After removing the gas via vacuum, perfluorobutane was placed in the stoppered bottle via another 18 gauge needle connected to tubing attached to the canister of perfluorobutane. This process was repeated 5 times such that any traces of air were removed from the stoppered bottle and the space above the lipid solution was completely filled with perfluorobutane. The pressure inside the glass bottle was equilibrated to ambient pressure by allowing the 18 gauge needle to vent for a moment or two before removing the 18 gauge needle from the stopper. After filling the bottle with perfluorobutane the bottle was secured to the arms of a Wig-L-Bug™ (Crescent Dental Mfg. Co., Lyons, Ill.) using rubber bands to fasten the bottle. The bottle was then shaken by the Wig-L-Bug™ for 60 seconds. A frothy suspension of foam resulted and it was noted that it took several minutes for any appreciable separation of the foam layer from the clear solution at the bottom. After shaking, the volume of the material increased from 5 cc to about 12 cc, suggesting that the liposomes entrapped about 7 cc of the perfluorocarbon gaseous precursor. The material was sized using an Accusizer (Model 770, Particle Sizing System, Santa Barbara, Calif.) and also examined by a light polarizing microscope (Nikon TMS, Nikon) at 150×magnification power. The liposomes appeared as rather large spherical structure with mean diameter of about 20 to 50 microns. A portion of these liposomes was then injected via a syringe through a Costar filter (Syrfil 800938, Costar, Pleasanton, Calif.) with pore sizes of 8 microns. The liposomes were again examined via light microscope and the Accusizer System. The mean size of the liposomes was about 3 microns and the volume weighted mean was about 7 microns. Greater that 99.9 percent of the liposomes were under 11 microns in size. The above experiment exhibits the use of a gaseous precursor gas, perfluorobutane, can be used to make very desirable sized liposomes by a process of shaking and filtration.

The above was substantially repeated except that after filling the bottle with perfluorobutane at room temperature the bottle was then transferred to a freezer and the material subjected to a temperature of −20° C. At this temperature the perfluorobutane became liquid. Because of the glycerol and propylene glycol, the lipid solution did not freeze. The bottle was quickly transferred to the Wig-L-Bug™ and subjected to shaking as described above for three cycles, one minute each, at room temperature. During this time the contents of the bottle equilibrated to room temperature and was noted to be slightly warm to the touch secondary to the energy imparted through shaking by the Wig-L-Bug™. At the end of vortexing a large volume of foam was again noted similar to that described above. The resulting liposomes were again studied by light microscopy and Accusizer. A portion was then subjected to filtration sizing through an 8 micron filter as described above and again studied by microscope and Accusizer. The results from sizing were substantially the same as with the gaseous precursor as described above.

Imaging was performed in a New Zealand White rabbit weighing about 3.5 kg. The animal was sedated with rabbit mix (Xylene 10 mg/ml; Ketamine 100 mg/ml and Acepromazine 20 mg/ml) and scanned with an Acoustic Imaging, Model No. 7200, clinical ultrasound machine, scanning the kidney by color doppler with a 7.5 MHz transducer. Simultaneously while the kidney was scanned the rabbits heart was also scanned using a second Acoustic Imaging ultrasound machine, model n. 5200, with a 7.5 MHz transducer for grey scale imaging of the heart. Injection of the perfluorobutane-filled liposomes was administered via ear vein through a syringe fitted with a 8 micron filter (see above). After injection of 0.5 cc (0.15 cc per kg) of liposomes containing the gaseous precursor perfluorobutane, dramatic and sustained enhancement of the kidney was observed for over 30 minutes. This was shown as brilliant color within the renal parenchyma reflecting increased signal within the renal arcuate arteries and microcirculation. The simultaneous imaging of the heart demonstrated shadowing for the first several minutes which precluded visualization of the heart, i.e. the reflections were so strong the ultrasound beam was completely reflected and absorbed. After several minutes, however, brilliant and sustained ventricular and blood pool enhancement was observed which also persisted for more than 50 minutes. Images were also obtained of the liver using the grey scale ultrasound machine. These showed parenchymal and vascular enhancement at the same time as the cardiac and blood pool enhancement.

In summary, this experiment demonstrates how liposomes can be used to entrap a gaseous precursor and create very stable liposomes of defined and ideal size. The invention has vast potential as an ultrasound contrast agent and for drug delivery. Because the liposomes are so stable they will pass through the target tissue (a tumor for example) via the circulation. Energy can then be focused on the target tissue using ultrasound, microwave radiofrequency or magnetic fields to pop the liposomes and perform local drug delivery.

EXAMPLE 2

Preparation of Gaseous Precursors via Microfluidization

Gaseous precursor-filled lipid bilayers were prepared as in Example 1 except, after addition of the gaseous precursor, the contents were microfluidized through six passes on a Microfluidics microfluidizer (Microfluidics Inc., Newton, Mass.). The stroke pressure ranged between 10,000 and 20,000 psi. Continuing with the preparation as per Example 1, produced gas-filled lipid bilayers with gaseous precursor encapsulated.

EXAMPLE 3

Formulation of Gas-filled Lipid Bilayers using Phosphatidic Acid and Dipalmitoyphosphatidylcholine Gas-filled lipid bilayers were prepared as set forth in Example 1 except for the fact that DPPC was used in combination with 5 mole % phosphatidic acid (Avanti Polar Lipids, Alabaster, Ala.). Formulation of gas-filled lipid bilayers resulted in an increase in solubility as exemplified by a decrease in the amount of lipid particulate in the lower aqueous vehicle layer. Resultant sizing appeared to decrease the overall mean size vs. DPPC alone to less than 40 um.

EXAMPLE 4

Formulation of Gas-filled Lipid Bilayers using Phosphatidic Acid, Dipalmitoylphosphatidylethanolamine-PEG 5,000 and Dipalmitoylphosphatidylcholine Perfluorobutane encapsulated lipid bilayers were formed as discussed in Example 3 except that the lipid formulation contained 82% dipalmitoylphosphatidylcholine, 10 mole % dipalmitoylphosphatidic acid, and 8 mole % dipalmitoylphosphatidylethanolamine-PEG 5,000 (Avanti Polar Lipids, Alabaster, Ala.) in a vehicle consisting of 8:1:1 (v:v:v) normal saline:propylene glycol:glycerol, yielding a foam and a lower vehicle layer that was predominantly devoid of any particulate. Variations of this vehicle yielded varying degrees of clarity to the lower vehicle layer. The formulation was prepared identically as in Example 3 to yield gas-filled lipid bilayers containing perfluorobutane. Prior to filtration, the gas-filled microspheres were sized on a Particle Sizing SYstems Model 770 optical sizer (Particle Sizing Systems, Santa Barbara, Calif.). Sizing resulted in 99% of all particles residing below 34 µm. The resultant product ws then filtered through an 8 µm filter to yield microspheres of uniform size. Sizing of the subsequent microspheres resulted in 99.5% of all particles residing below 10 µm. This product was used in the in vivo experiments in Example 1.

It is noted that the vehicle was altered with other viscosity modifiers and solubilizers in varying proportions which resulted in greater or lesser degrees of clarity and particulate. Amongst a variety of lipids and lipid analogs used in combination, it was subsequently found that the introduction of DPPE-PEG lipid significantly improved the size distribution and apparent stability of the gas-filled lipid bilayers.

EXAMPLE A

Binding of DNA by Gas-Filled Lipid Bilayers

Binding of DNA by liposomes containing phosphatidic acid and gaseous precursor and gas containing liposomes. A 7 mM solution of distearoyl-sn-glycerophospate (DSPA) (Avanti Polar Lipids, Alabaster, Ala.) was suspended in normal saline and vortexed at 50° C. The material was allowed to cool to room temperature. 40 micrograms of pBR322 plasmid DNA (International Biotechnologies, Inc., New Haven, Conn.) was added to the lipid solution and shaken gently. The solution was centrifuged for 10 minutes in a Beckman TJ-6 Centrifuge (Beckman, Fullerton, Calif.). The supernatant and the precipitate were assayed for DNA content using a Hoefer TKO-100 DNA Fluorometer (Hoefer, San Francisco, Calif.). This method only detects double stranded DNA as it uses an intercalating dye, Hoechst 33258 which is DNA specific. It was found that the negatively charged liposomes, or lipids with a net negative charge, prepared with phosphatidic acid surprisingly bound the DNA. This experiment was repeated using neutral liposomes composed of DPPC as a control. No appreciable amount of DNA was detected with the DPPC liposomes. The experiment was repeated using gas-filled liposomes prepared from an 87:8:5 mole percent of DPPC to DPPE-PEG 500 to DPPA mixture of lipids in a microsphere. Again, the DNA bound to the gas-filled liposomes containing dipalmitoylphosphatidic acid.

EXAMPLE 5

Microemulsification of Precursor

A Microfluidizer (Microfluidics, Newton, Mass.) was placed in a cold room at −20° C. A stoppered glass flask containing a head space of 35 cc of perfluorobutane and 25 cc of lipid solution was taken into the cold room. The lipid solution contained an 83:8:5 molar ratio of DPPC:DPPE+PEG 5,000:DPPA in 8:1:1 phosphate buffered saline (pH 7.4):glycerol:propylene glycol. The solution did not freeze in the cold room but the perfluorobutane became liquid.

The suspension of lipids and liquid gaseous precursor was then placed into the chamber of the Microfluidizer and subjected to 20 passes at 16,000 psi. Limited size vesicles, having a size of about 30 nm to about 50 nm, resulted. Upon warming to room temperature, stabilized microspheres of about 10 microns resulted.

EXAMPLE 6

Preparation of Gaseous Precursor-filled Liposomes

Fifty mg of 1,2-Dipalmitoyl-Sn-Glycero-3-Phosphocholine (MW: 734.05, powder, Lot No. 160pc-183) (Avanti-Polar Lipids, Alabaster, Ala.) is weighed and hydrated with 5.0 ml of saline solution (0.9% NaCl) or phosphate buffered saline (0.8% sodium chloride, 0.02% potassium chloride, 0.115% dibasic sodium phosphate and 0.02% monobasic potassium phosphate, pH adjusted to 7.4) in a centrifuge tube. To this suspension is added 165 µL mL$^{-1}$ of 2-methyl-2-butene. The hydrated suspension is then shaken on a vortex machine (Scientific Industries, Bohemia, N.Y.) for 10 minutes at an instrument setting of 6.5. A total volume of 12 ml is then noted. The saline solution is expected to decrease from 5.0 ml to about 4 ml.

The gaseous precursor-filled liposomes made via this new method are then sized by optical microscopy. It will be determined that the largest size of the liposomes ranged from about 50 to about 60 µm and the smallest size detected is about 8 µm. The average size ranges from about 15 to about 20 µm.

The gaseous precursor-filled liposomes are then filtered through a 10 or 12 µm "NUCLEPORE" membrane using a Swin-Lok Filter Holder, (Nuclepore Filtration Products, Costar Corp., Cambridge, Mass.) and a 20 cc syringe (Becton Dickinsion & Co., Rutherford, N.J.). The membrane is a 10 or 12 µm "NUCLEPORE" membrane (Nuclepore Filtration Products, Costar Corp., Cambridge, Mass.). The 10.0 µm filter is placed in the Swin-Lok Filter Holder and the cap tightened down securely. The liposome solution is shaken up and transferred to the 20 cc syringe via an 18 gauge needle. Approximately 12 ml of liposome solution is placed into the syringe, and the syringe is screwed onto the Swin-Lok Filter Holder. The syringe and the filter holder assembly are inverted so that the larger of the gaseous precursor-filled liposomes vesicles could rise to the top. Then the syringe is gently pushed up and the gaseous precursor-filled liposomes are filtered in this manner.

The survival rate (the amount of the gaseous precursor-filled liposomes that are retained after the extrusion process) of the gaseous precursor-filled liposomes after the extrusion through the 10.0 µm filter is about 83–92%. Before hand extrusion, the volume of foam is about 12 ml and the volume of aqueous solution is about 4 ml. After hand extrusion, the volume of foam is about 10–11 ml and the volume of aqueous solution is about 4 ml.

The optical microscope is used again to determine the size distribution of the extruded gaseous precursor-filled liposomes. It will be determined that the largest size of the liposomes range from about 25 to about 30 µm and the smallest size detected is about 5 µm. The average size range is from about 8 to about 15 µm.

It is found that after filtering, greater than 90% of the gaseous precursor-filled liposomes are smaller than 15 µm.

EXAMPLE 7

Preparation of Gaseous Precursor-Filled Liposomes Incorporating Lyophilization

Fifty mg of 1,2-Dipalmitoyl-sn-Glycero-3-Phosphocholine, (MW: 734.05, powder) (Avanti-Polar Lipids, Alabaster, Ala.) is weighed and placed into a centrifuge tube. The lipid is then hydrated with 5.0 ml of saline solution (0.9% NaCl). To this suspension is added 165 µL mL of 2-methyl-2-butene. The lipid is then vortexed for 10 minutes at an instrument setting of 6.5. After vortexing, the entire solution is frozen in liquid nitrogen. Then the sample is put on the lyophilizer for freeze drying. The sample is kept on the lyophilizer for 18 hours. The dried lipid is taken off the lyophilizer and rehydrated in 5 ml of saline solution and vortexed for ten minutes at a setting of 6.5. A small sample of this solution is pipetted onto a slide and the solution is viewed under a microscope. The size of the gaseous precursor-filled liposomes will then be determined. It will be determined that the largest size of the liposomes is about 60 µm and the smallest size detected is about 20 µm. The average size range is from about 30 to about 40 µm.

EXAMPLE 8

Example of Gaseous Precursor-filled Liposome Preparation Above the Phase Transition Temperature of the Lipid Fifty mg of 1,2-Dipalmitoyl-Sn-Glycero-3-Phosphocholine (MW: 734.05, powder) (Avanti-Polar Lipids, Alabaster, Ala.) is weighed and placed into a centrifuge tube. To this suspension is added 165 µL mL$^{-1}$ of 2-methyl-2-butene. Approximately two feet of latex tubing (0.25 in. inner diameter) is wrapped around a conical centrifuge tube in a coil-like fashion. The latex tubing is then fastened down to the centrifuge tube with electrical tape. The latex tubing is then connected to a constant temperature circulation bath (VWR Scientific Model 1131). The temperature of the bath is set to 60° C. and the circulation of water is set to high speed to circulate through the tubing. A thermometer is placed in the lipid solution and found to be between 42° C. and 50° C.

The lipid solution is vortexed for a period of 10 minutes at a vortex instrument setting of 6.5. It will be noted that very little foaming of the lipid (phase transition temp.=41° C.) and that the suspension did not appreciably form gaseous precursor-filled liposomes. Optical microscopy revealed large lipidic particles in the solution. The number of gaseous precursor-filled liposomes that form at this temperature is less than 3% of the number that form at a temperature below the phase transition temperature. The solution is allowed to sit for 15 minutes until the solution temperature equilibrated to room temperature (25° C.). The solution is then vortexed for a duration of 10 minutes. After 10 minutes, it will be noted that gaseous precursor-filled liposomes formed.

EXAMPLE 9

Preparation of Gaseous Precursor-filled Liposomes Incorporating a Freeze-Thaw Procedure 50 mg of 1,2-Dipalmitoyl-Sn-Glycero-3-Phosphocholine (MW: 734.05, powder) (Avanti-Polar Lipids, Alabaster, Ala.) is weighed and placed into a centrifuge tube. The lipid is then hydrated with 5.0 ml of 0.9% NaCl added. To this suspension is added 165 µL mL$^{-1}$ of 2-methyl-2-butene. The aqueous lipid solution is vortexed for 10 minutes at an instrument setting of 6.5. After vortexing, the entire solution is frozen in liquid nitrogen. The entire solution is then thawed in a water bath at room temperature (25° C.). The freeze thaw procedure is then repeated eight times. The hydrated suspension is then vortexed for 10 minutes at an instrument setting of 6.5. Gaseous precursor-filled liposomes are then detected as described in Example 6.

EXAMPLE 10

Preparation of Gaseous Precursor-Filled Liposomes with an Emulsifying Agent (Sodium Lauryl Sulfate)

Two centrifuge tubes are prepared, each having 50 mg of DPPC. 1 mol % (~0.2 mg of Duponol C lot No. 2832) of sodium lauryl sulfate is added to one of the centrifguge tubes, and the other tube receives 10 mol % (2.0 mg of Duponol C lot No. 2832). Five ml of 0.9% NaCl is added to both centrifuge tubes. 165 µL mL$^{-1}$ of 2-methyl-2-butene is added to both tubes. Both of the tubes are frozen in liquid nitrogen and lyophilized for approximately 16 hours. Both samples are removed from the lyophilizer and 5 ml of saline is added to both of the tubes. Both of the tubes are vortexed at position 6.5 for 10 minutes.

It will be determined that the largest size of the gaseous precursor-filled liposomes with 1 mol % of sodium lauryl sulfate is about 75 µm and the smallest size detected is about 6 µm. The average size range is from about 15 to about 40 µm. It will be determined that the largest size of the gaseous precursor-filled liposomes with 10 mol % of sodium lauryl sulfate is about 90 µm and the smallest size detected is about 6 µm. The average size range is from about 15 to about 35 µm.

The volume of foam in the solution containing gaseous precursor-filled liposomes with 1 mol % sodium lauryl sulfate is about 15 ml and the volume of aqueous solution is about 3–4 ml. The volume of foam in the solution containing gaseous precursor-filled liposomes with 10 mol % sodium lauryl sulfate is also about 15 ml and the volume of aqueous solution is about 3–4 ml.

EXAMPLE 11

Determination of Whether Gaseous Precursor-Filled Liposomes Can be Generated by Sonication 50 mg of lipid, 1,2-Dipalmitoyl-Sn-Glycero-3-Phosphocholine (Avanti-Polar Lipids, Alabaster, Ala.), is weighed out and hydrated with 5 ml of 0.9% NaCl. To this suspension is added 165 µL/mL$^{-1}$ of 2-methyl-2-butene. Instead of vortexing, the aqueous solution is sonicated using a Heat Systems Sonicator Ultrasonic Processor XL (Heat Systems, Inc., Farmingdale, N.Y.) Model XL 2020. The sonicator, with a frequency of 20 KHz, is set to continuous wave, at position 4 on the knob of the sonicator. A micro tip is used to sonicate for 10 minutes at a temperature of 4° C. Following sonication, the temperature is increased to 40° C. and the solution is viewed under an optical microscope. There will be evidence of gaseous precursor-filled liposomes having been produced.

Next, the above is repeated with sonication at a temperature of 50° C. and 165 µL mL$^{-1}$ of 2-methyl 2-butene is added. The micro tip of the sonicator is removed and replaced with the end cap that is supplied with the sonicator. Another solution (50 mg of lipid per 5 ml of saline) is prepared and sonicated with this tip. After 10 minutes, the solution is viewed under the microscope. The production of gas-filled liposomes with sonication above the temperature of the transition of the gas resulted in a lower yield of gas-filled lipid spheres.

EXAMPLE 12

Determination of Concentration Effects on Gaseous Precursor-Filled Liposome Production This example determined whether a lower concentration limit of the lipid halts the production of gaseous precursor-filled liposomes. Ten mg of 1,2-Dipalmitoyl-Sn-Glycero-3-Phosphocholine (Avanti-Polar Lipids, Alabaster, Ala.) is added to 10 ml of saline. To this suspension is added 165 $\mu L/mL^{-1}$ of 2-methyl-2-butene. The lipid/saline/gas precursor solution is vortexed at position 6.5 for 10 minutes. The solution is viewed under an optical microscope for sizing. It will be determined that the largest size of the liposomes ranges from about 30 to about 45 $\mu m$ and the smallest size detected is about 7 $\mu m$. The average size range is from about 30 to about 45 $\mu m$.

It appears that the gaseous precursor-filled liposomes are more fragile as they appear to burst more rapidly than previously shown. Thus, it appears that concentration of the lipid is a factor in the generation and stability of gaseous precursor-filled liposomes.

EXAMPLE 13

Cascade Filtration

Unfiltered gaseous precursor-filled liposomes may be drawn into a 50 ml syringe and passed through a cascade of a "NUCLEPORE" 10 $\mu m$ filter and 8 $\mu m$ filter that are a minimum of 150 $\mu m$ apart (FIGS. 3 and 4). Alternatively, for example, the sample may be filtered through a stack of 10 $\mu m$ and 8 $\mu m$ filters that are immediately adjacent to each other. Gaseous precursor-filled liposomes are passed through the filters at a pressure whereby the flow rate is 2.0 ml min$^{-1}$. The subsequently filtered gaseous precursor-filled liposomes are then measured for yield of gaseous precursor-filled lipid liposomes which results in a volume of 80–90% of the unfiltered volume.

The resulting gaseous precursor-filled liposomes are sized by four different methods to determine their size and distribution. Sizing is performed on a Particle Sizing Systems Model 770 Optical Sizing unit, a Zeiss Axioplan optical microscope interfaced to image processing software manufactured by Universal Imaging, and a Coulter Counter (Coulter Electronics Limited, Luton, Beds., England). As seen in FIGS. 5A and 5B and 6A and 6B, the size of the gaseous precursor-filled liposomes are more uniformly distributed around 8–10 $\mu m$ as compared to the unfiltered gaseous precursor-filled liposomes. Thus, it can be seen that the filtered gaseous precursor-filled liposomes are of much more uniform size.

EXAMPLE 14

Preparation of Filtered DPPC Suspension 250 mg DPPC (dipalmitoylphosphatidylcholine) and 10 ml of 0.9% NaCl are added to a 50 ml Falcon centrifuge tube (Becton-Dickinson, Lincoln Park, N.J.) and maintained at an ambient temperature (approx. 20° C.). To this suspension is added 165 $\mu L/mL^{-1}$ of 2-methyl-2-butene. The suspension is then extruded through a 1 $\mu m$ Nuclepore (Costar, Pleasanton, Calif.) polycarbonate membrane under nitrogen pressure. The resultant suspension is sized on a Particle Sizing Systems (Santa Barbara, Calif.) Model 370 laser light scattering sizer. All lipid particles are 1 $\mu m$ or smaller in mean outside diameter.

In addition, the same amount of DPPC/gas precursor suspension is passed five times through a Microfluidics™ (Microfluidics Corporation, Newton, Mass.) microfluidizer at 18,000 p.s.i. The suspension, which becomes less murky, is sized on a Particle Sizing Systems (Santa Barbara, Calif.) Sub Micron Particle Sizer Model 370 laser light scattering sizer where it is found that the size is uniformly less than 1 $\mu m$. The particle size of microfluidized suspensions is known to remain stable up to six months.

EXAMPLE 15

Preparation of Filtered DSPC Suspension 100 mg DSPC (distearoylphosphatidylcholine) and 10 ml of 0.9% NaCl are added to a 50 ml Falcon centrifuge tube (Becton-Dickinson, Lincoln Park, N.J.). To this suspension is added 165 $\mu L/mL^{-1}$ of 2-methyl-2-butene. The suspension is then extruded through a 1 $\mu m$ "NUCLEPORE" (Costar, Pleasanton, Calif.) polycarbonate membrane under nitrogen pressure at 300–800 p.s.i. The resultant suspension is sized on a Particle Sizing Systems (Santa Barbara, Calif.) Sub Micron Particle Sizer Model 370 laser light scattering sizer. It will be found that all particles are 1 $\mu m$ or smaller in size.

In addition, the same amount of DPPC/gas precursor suspension is passed five times through a Microfluidics™ (Microfluidics Corporation, Newton, Mass.), microfluidizer at 18,000 p.s.i. The resultant suspension, which is less murky, is sized on a Sub Micron Particle Sizer Systems Model 370 laser light scattering sizer and it is found that the size is uniformly less than 1 $\mu m$.

EXAMPLE 16

Sterilization of Filtered Lipid Suspensions by Autoclaving

The previously sized suspensions of DPPC/gas precursor and DSPC/gas precursor of Examples 9 and 10 are subjected to autoclaving for twenty minutes on a Barnstead Model C57835 autoclave (Barnstead/Thermolyne, Dubuque, Ind.) and then subjected to shaking. A filtration step may be performed immediately prior to use through an in line filter. Also, the gaseous precursor may be autoclaved before sizing and shaking.

After equilibration to room temperature (approx. 20° C.), the sterile suspension is used for gaseous precursor instillation.

EXAMPLE 17

Gaseous Precursor Instillation of Filtered, Autoclaved Lipids via vortexing 10 ml of a solution of 1,2-dipalmitoyl-phosphatidylcholine at 25 mg/ml in 0.9% NaCl, which had previously been extruded through a 1 $\mu m$ filter and autoclaved for twenty minutes, is added to a Falcon 50 ml centrifuge tube (Becton-Dickinson, Lincoln Park, N.J.). To this suspension is added 165 $\mu L/mL^{-1}$ of 2-methyl-2-butene. After equilibration of the lipid suspension to room temperature (approximately 20° C.), the liquid is vortexed on a VWR Genie-2 (120V, 0.5 amp, 60 Hz.) (Scientific Industries, Inc., Bohemia, N.Y.) for 10 minutes or until a time that the total volume of gaseous precursor-filled liposomes is at least double or triple the volume of the original aqueous lipid solution. The solution at the bottom of the tube is almost totally devoid of anhydrous particulate lipid, and a large volume of foam containing gaseous precursor-filled liposomes results. Thus, prior autoclaving does not affect the ability of the lipid suspension to form gaseous precursor-filled liposomes. Autoclaving does not change the size of the liposomes, and it does not decrease the ability of the lipid suspensions to form gaseous precursor-filled liposomes.

EXAMPLE 18

Gaseous Precursor Instillation of Filtered, Autoclaved Lipids via Shaking on Shaker Table 10 ml of a solution of 1,2-dipalmitoyl-phosphatidylcholine at 25 mg/ml in 0.9% NaCl, which has previously been extruded through a 1 μm filter and autoclaved for twenty minutes, is added to a Falcon 50 ml centrifuge tube (Becton-Dickinson, Lincoln Park, N.J.). To this suspension is added 165 μL/mL$^{-1}$ of perfluoropentane (PCR Research Chemicals, Gainesville, Fla.). After equilibration of the lipid suspension to room temperature (approximately 20° C.), the tube is then placed upright on a VWR Scientific Orbital shaker (VWR Scientific, Cerritos, Calif.) and shaken at 300 r.p.m. for 30 minutes. The resultant agitation on the shaker table results in the production of gaseous precursor-filled liposomes.

EXAMPLE 18

The above experiment may be performed replacing perfluoropentane with sulfur hexafluoride, hexafluoropropylene, bromochlorofluoromethane, octafluoropropane, 1,1 dichloro, fluoro ethane, hexafluoroethane, hexafluoro-2-butyne, perfluoropentane, perfluorobutane, octafluoro-2-butene or hexafluorobuta-1,3-diene or octafluorocyclopentene, all with the production of gaseous precursor filled liposomes.

EXAMPLE 19

Gaseous Precursor Instillation of Filtered, Autoclaved Lipids via Shaking on Shaker Table via Shaking on Paint Mixer 10 ml of a solution of 1,2-dipalmitoyl-phosphatidylcholine at 25 mg/ml in 0.9% NaCl, which has previously been extruded through a 1 μm filter and autoclaved for twenty minutes, is added to a Falcon 50 ml centrifuge tube (Becton-Dickinson, Lincoln Park, N.J.). To this suspension is added 165 μL/mL$^{-1}$ of 2-methyl-2-butene. After equilibration of the lipid suspension to room temperature (approximately 20° C.), the tube is immobilized inside a 1 gallon empty household paint container and subsequently placed in a mechanical paint mixer employing a gyrating motion for 15 minutes. After vigorous mixing, the centrifuge tube is removed, and it is noted that gaseous precursor-filled liposomes form.

EXAMPLE 20

Gaseous Precursor Instillation of Filtered, Autoclaved Lipids via Shaking by Hand 10 ml of a solution of 1,2-dipalmitoyl-phosphatidylcholine at 25 mg/ml in 0.9% NaCl, which had previously been extruded through a 1 μm nuclepore filter and autoclaved for twenty minutes, is added to a Falcon 50 ml centrifuge tube (Becton-Dickinson, Lincoln Park, N.J.). To this suspension is added 165 μL/mL$^{-1}$ of 2-methyl-2-butene. After equilibration of the lipid suspension to room temperature (approximately 20° C.), the tube is shaken forcefully by hand for ten minutes. Upon ceasing agitation, gaseous precursor-filled liposomes form.

EXAMPLE 21

Sizing Filtration of Autoclaved Gaseous Precursor-Filled Liposomes via Cascade or Stacked Filters Gaseous precursor-filled liposomes are produced from DPPC as described in Example 17. The resultant unfiltered liposomes are drawn into a 50 ml syringe and passed through a cascade filter system consisting of a "NUCLEPORE" (Costar, Pleasanton, Calif.) 10 μm filter followed by an 8 μm filter spaced a minimum of 150 μm apart. In addition, on a separate sample, a stacked 10 μm and 8 μm filtration assembly is used, with the two filters adjacent to one another. Gaseous precursor-filled liposomes are passed through the filters at a pressure such that they are filtered a rate of 2.0 ml/min. The filtered gaseous precursor-filled liposomes yields a volume of 80–90% of the unfiltered volume.

The resultant gaseous precursor-filled liposomes are sized by four different methods to determine their size distribution. Sizing is performed on a Particle Sizing Systems (Santa Barbara, Calif.) Model 770 Optical Sizing unit, and a Zeiss (Oberkochen, Germany) Axioplan optical microscope interfaced to image processing software (Universal Imaging, West Chester, Pa.) and a Coulter Counter (Coulter Electronics Limited, Luton, Beds., England). As illustrated in FIGS. 8A and 8B, the size of the gaseous precursor-filled liposomes is more uniformly distributed around 8–10 μm as compared to the unfiltered gaseous precursor-filled liposomes.

EXAMPLE 22

Extra Efficient Production of Gas-Precursor Filled Lipid Spheres

The same procedure as in Example 6 is performed except that the shaker used is a Crescent "Wig-L-Bug™ (Crescent Manufacturing Dental Co., Lyons, Ill.). The formulation is then agitated for 60 seconds instead of the usual 5 minutes to 10 minutes as described previously. Gas-filled lipid spheres are produced.

EXAMPLE 23

100 μL of perfluoropentane (bp 29.5° C., PCR Research Chemicals, Gainesville, Fla.) was added to a 5 mg/mL lipid suspension and vortexed on a Genie II mixer (Scientific Industries, Inc., Bohemia, N.Y.) at room temperature at power setting of 6.5. A Richmar (Richmar Industries, Inola, Okla.) 1 MHz therapeutic ultrasound device was then used to perform hyperthermia, elevating the temperature to above 42° C. as measured by a thermometer. Upon reaching the phase transition temperature, gas microspheres were noted. A simultaneous scanning was performed with a diagnostic ultrasound (Acoustic Imaging, Phoenix, Ariz.). Acoustic signals from the gas microspheres could also be visualized on the clinical diagnostic ultrasound.

The same exeriment was conducted with octafluorocyclopentene (bp 27° C., PCR Research Chemicals, Gainesville, Fla.).

EXAMPLE 24

An experiment identical to Example 23 was performed where the suspension was vortexed and injected into a Harlan-Sprague Dawley rat, 300 grams, previously given a C5A tumor cell line in the left femoral region. A Richmar 1 MHz therapeutic ultrasound was then placed over the tumor region and an adriamycin embedded lipid suspension injected intravenously. The therapeutic ultrasound was then placed on a continuous wave (100% duty cycle) setting and the tumor heated. A second rat, having a C5A tumor cell line in the left femoral region, was given an identical dose of the adriamycin emulsion, however, no ultrasound was utilized in this animal. Within three weeks it was noted that the tumor, compared to the control without the use of ultrasound, was noticeably smaller.

Various modifications of the invention in addition to those shown and described herein will be apparent to those skilled in the art from the foregoing description. Such modifications are also intended to fall within the scope of the appended claims.

What is claimed is:

1. A method for preparing temperature activated gaseous precursor-filled lipid microspheres comprising shaking an aqeous solution comprising a lipid, in the presence of a temperature activated gaseous precursor at a temperature below the gel state to liquid crystalline transition temperature of the lipid, and separating the resulting gaseous precursor-filled lipid microspheres for diagnositc or therapeutic use, wherein said lipid comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dipalmitoylphosphatidylethanolamine-PEG 5,000, dioleoyl-phosphatidylethanolamine, and N-succinyl-dioleoyl-phosphatidylethanolamine; and said phosphatidic acid is dipalmatoylphosphatidic acid.

2. A method of making gaseous precursor-filled lipid microspheres, comprising the steps of:
   a) introducing an aqueous solution comprising a lipid into a vessel;
   b) introducing a temperature activated gaseous precursor into said vessel;
   c) shaking said aqueous lipid solution in the presence of said gaseous precursor at a temperature below the gel state to liquid crystalline transition temperature of the lipid so as to instill at least a portion of said gaseous precursor into said aqueous solution, said shaking performed with sufficient intensity and duration to produce a gaseous precursor-filled-lipid microspheres-containing foam above said aqueous solution; and
   d) extracting at least a portion of said gaseous precursor-filled-lipid microspheres-containing foam from said vessel;
   wherein said lipid comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dipalmitoylphosphatidylethanolamine-PEG 5,000, dioleoyl-phosphatidylethanolamine, and N-succinyl-dioleoyl-phosphatidylethanolamine; and said phosphatidic acid is dipalmatoylphosphatidic acid.

3. The method as in claim 2 wherein said method is performed at the activation temperature of the precursor.

4. The method according to claim 2, further comprising the step of pressurizing said vessel.

5. The method according to claim 2, further comprising the step of sizing said gaseous precursor-filled lipid microspheres.

6. The method according to claim 5, wherein the step of sizing said gaseous precursor-filled lipid microspheres comprises controlling the size of said gaseous precursor-filled lipid microspheres extracted from said vessel.

7. The method according to claim 5, wherein the size of said gaseous precursor-filled lipid microspheres extracted from said vessel is controlled by extracting said gaseous precursor-filled lipid microspheres through a filter.

8. The method according to claim 5, wherein the size of said gaseous precursor-filled lipid microspheres extracted from said vessel is controlled by setting the location within said vessel from which said gaseous precursor-filled lipid microspheres are extracted.

9. The method according to claim 5, wherein the size of said gaseous precursor-filled lipid microspheres extracted from said vessel is controlled by adjusting the location within said vessel from which said gaseous precursor-filled lipid microspheres are extracted during the step of extracting said gaseous precursor-filled lipid microspheres from said vessel.

10. The method according to claim 5, wherein the step of sizing said gaseous precursor-filled lipid microspheres comprises forcing said extracted gaseous precursor-filled lipid microspheres through a filter.

11. The method according to claim 5, wherein the step of sizing said gaseous precursor-filled lipid microspheres comprises controlling the intensity of said shaking.

12. The method according to claim 2, further comprising the step of flowing said gaseous precursor-filled lipid microspheres extracted from said vessel into a syringe without further processing.

13. The method according to claim 2, wherein the step of shaking said aqueous solution comprises the step of shaking at a frequency of at least about 60 shaking motions per minute.

14. The method according to claim 2, wherein the step of shaking said aqueous solution comprises the step of vortexing said aqueous solution.

15. The method according to claim 2, wherein the step of shaking said aqueous solution comprises the step of shaking said vessel.

16. The method according to claim 2, wherein the step of shaking said aqueous solution comprises shaking said aqueous solution with sufficient intensity to create said gaseous precursor-filled-lipid microspheres-containing foam in less than about 30 minutes.

17. The method according to claim 2, wherein the step of shaking said aqueous solution comprises the step of controlling the duration of said shaking based on the detection of said gaseous precursor-filled-lipid microspheres-containing foam.

18. The method according to claim 17, wherein the step of controlling the duration of said shaking based on the detection of said gaseous precursor-filled-lipid microspheres-containing foam comprises shaking until the presence of a pre-determined volume of said foam has been detected.

19. A method of making gaseous precursor-filled lipid microspheres, comprising the steps of:
   a) introducing an aqueous solution comprising a lipid into a vessel;
   b) introducing a temperature activated gaseous precursor into said vessel;
   c) shaking said aqueous lipid solution below the activation temperature of said gaseous precursor and at a temperature below the gel state to lipid crystalline transition temperature of the lipid;
   d) filtering said aqueous lipid solution;
   e) shaking said aqueous lipid solution above the activation temperature of said gaseous precursor in the presence of said gaseous precursor so as to instill at least a portion of said gaseous precursor into said aqueous solution, said shaking performed with sufficient intensity and duration to produce a gaseous precursor-filled-lipid microspheres-containing foam above said aqueous solution; and f) extracting at least a portion of said gaseous precursor-filled-lipid microspheres-containing foam from said vessel;

wherein said lipid comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dipalmitoylphosphatidylethanolamine-PEG 5,000, dioleoyl-phosphatidylethanolamine, and N-succinyl-dioleoyl-phosphatidylethanolamine; and said phosphatidic acid is dipalmatoylphosphatidic acid.

20. The method according to claim 19, further comprising the step of pressurizing said vessel.

21. The method according to claim 19, further comprising the step of sizing said gaseous precursor-filled lipid microspheres.

22. The method according to claim 21, wherein the step of sizing said gaseous precursor-filled lipid microspheres comprises controlling the size of said gaseous precursor-filled lipid microspheres extracted from said vessel.

23. The method of claim 2 where said method takes place in a syringe and further comprising passing said aqueous lipid solution through filter at the end of said syringe.

24. The method of claim 19 where said aqueous lipid solution is filtered and then added to a syringe, wherein said method takes place in said syringe.

25. The method of claim 2 wherein said vessel is a barrel of a syringe, said syringe also comprising at least one filter and a needle, wherein said barrel contains said aqueous lipid solution and said gaseous precursor for said shaking step; and said step of extracting comprises sizing said gas-filled lipid microspheres by extruding said lipid microspheres from said barrel through said filter.

26. The method of claim 19 wherein said vessel is a barrel of a syringe.

27. The method of claim 26 wherein said syringe also comprises at least one filter and a needle; said step of extracting comprises sizing said gas-filled lipid microspheres by extruding said lipid microspheres from said barrel through said filter.

28. The method of claim 6 comprising drawing said lipid microspheres into a syringe, said syringe comprising a barrel, at least one filter, and a needle; whereby said filter sizes said lipid microspheres upon drawing said lipid microspheres into said barrel.

29. The method of claim 6 comprising extruding said lipid microspheres into a barrel of a syringe, said syringe also comprising at least one filter and a needle, whereby said filter sizes said lipid microspheres upon extruding said lipid microspheres from said barrel.

30. The method of claim 6 wherein said step of extracting comprises drawing said gas-filled liposome-containing foam into a syringe, said syringe comprising a barrel, at least one filter, and a needle; thereby sizing said lipid microspheres.

31. The method of claim 1 performed at a pressure above ambient pressure.

32. A method for preparing gas or gaseous precursor-filled lipid microspheres comprising shaking an aqueous solution comprising a lipid in the presence of a fluorinated gas or gaseous precursor at a temperature below the gel state to liquid crystalline state phase transition temperature of the lipid, wherein the fluorinated gas or gaseous precursor is selected from the group consisting of 1-fluorobutane, hexafluoro acetone, tetrafluoroallene, boron trifluoride, 1,2,3-trichloro, 2-fluoro-1,3-butadiene, hexafluoro-1,3-butadiene, 1-fluoro-butane, 1,2,3-trichloro, 2-fluoro-1,3-butadiene; hexafluoro-1,3-butadiene; 1-fluoro-butane; decafluoro butane; perfluoro 1-butene; perfluoro-1-butene; perfluoro-2-butene; 2-chloro-1,1,1,4,4,4-hexafluoro-butyne; perfluoro-2-butyne; octafluoro-cyclobutane; perfluoro-cyclobutane; perfluoroethane; perfluoropropane; perfluorobutane; perfluoropentane; perfluorohexane; 1,1,1-trifluorodiazoethane; hexafluoro-dimethyl amine; perfluorodimethylamine; 4-methyl, 1,1,1,2-tetrafluoro ethane; 1,1,1-trifluoroethane; 1,1,2,2-tetrafluoroethane; 1,1,2-trichloro-1,2,2-trifluoroethane; 1,1-dichloro-1,2,2,2-tetrafluoro ethane; 1,2-difluoro ethane; 1-chloro-1,1,2,2,2-pentafluoro ethane; 2-chloro, 1,1-difluoroethane; 1-chloro-1,1,2,2-tetrafluoro ethane-2-chloro, 1,1-difluoroethane-chloropentafluoro ethane; dichlorotrifluoroethane; fluoroethane; hexafluoroethane; nitro-pentafluoro ethane; nitroso-pentafluoro ethane; perfluoro ethane; perfluoro ethylamine; 1,1-dichloro-1,2-difluoro ethylene; 1,2-difluoro ethylene; methanesulfonyl chloridetrifluoro; methanesulfonyl fluoride-trifluoro; methane-(pentafluorothio)trifluoro; methanebromo difluoro nitroso; methane-bromo fluoro; methane-bromo chlorofluoro; methanebromotrifluoro; methane-chloro difluoro nitro; methanechloro fluoro; methane-chloro trifluoro; methane-chloro-difluoro; methane dibromo difluoro; methane-dichloro difluoro; methanedichloro-fluoro-1 methanedifluoro; methane-difluoro-iodo; methane-fluoro; 8 methane-iodo-trifluoro; methane-nitro-trifluoro; methane-nitroso-trifluoro; methane-tetrafluoro; methane-trichlorofluoro; methane-trifluoro; methanesulfenylchloride-trifluoro; pentaneperfluoro; 1-pentane-perfluoro; propane-1,1,1,2,2,3-hexafluoro; propane-2,2 difluoro; propane-heptafluoro-1-nitro; propane-heptafluoro-1-nitroso; propane-perfluoro; propyl 1,1,1,2,3,3-hexafluoro-2,3 dichloro; propylene-3-fluoro; propylene-perfluoro; propyne-3,3,3trifluoro; styrene-3-fluoro; sulfur hexafluoride; sulfur (di)-decafluoro; trifluoroacetonitrile; trifluoromethyl peroxide; trifluoromethyl sulfide; tungsten hexafluoride, pentafluoro octadecyl iodide, perfluorooctylbromide, perfluorodecalin, perfluorododecalin, perfluorooctyliodide, perfluorotripropylamine, and perfluorotributylamine, hexafluoropropylene, bromochlorofluoromethane, octafluoropropane, 1,1 dichloro, fluoro ethane, hexa fluoroethane, hexafluoro-2-butyne, perfluoropentane, perfluorobutane, octafluoro-2-butene, hexafluorobuta-1, 3diene, octafluorocyclopentene;

wherein said lipid comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dipalmitoylphosphatidylethanolamine-PEG 5,000, dioleoyl-phosphatidylethanolamine, and N-succinyl-dioleoyl-phosphatidylethanolamine; and said phosphatidic acid is dipalmatoylphosphatidic acid.

33. The method of claim 32 wherein said fluorinated gas or gaseous precursor is selected from the group consisting of perfluoromethane, perfluoroethane, perfluoropropane, perfluorobutane, perfluoropentane, perfluorohexane, sulfur hexafluoride, hexafluoropropylene, octafluoropropane, perfluorocyclobutane, octafluorocyclopentene, dodecafluoropentane, and octafluorocyclobutane.

34. The method of claim 33 wherein said fluorinated gas or gaseous precursor is selected from the group consisting of perfluoromethane, perfluoroethane, perfluoropropane, perfluorobutane, perfluorocyclobutane, and sulfur hexafluoride.

35. The method of claim 34 wherein said fluorinated gas or gaseous precursor is selected from the group consisting of perfluoropropane, perfluorocyclobutane, and perfluorobutane.

36. The method of claim 35 wherein said fluorinated gas or gaseous precursor is perfluoropropane.

37. The method of claim 32 wherein said fluorinated gas or gaseous precursor is a perfluorocarbon gas.

38. A method for preparing gas or gaseous precursor-filled lipid microspheres comprising shaking an aqueous solution comprising a lipid, in the presence of a fluorinated gas or gaseous precursor, at a temperature below the gel state to liquid crystalline state phase transition temperature of the lipid, and separating the resulting gas or gaseous precursor-filled lipid microspheres for diagnostic or therapeutic use, wherein said fluorinated gas or gaseous precursor is selected from the group consisting of 1-fluorobutane, hexafluoro acetone, tetrafluoroallene, boron trifluoride, 1,2,3-trichloro, 2-fluoro-1,3-butadiene, hexafluoro-1,3-butadiene, 1-fluoro-butane, 1,2,3-trichloro, 2-fluoro-1,3-butadiene; hexafluoro-1,3-butadiene-1-fluoro-butane; decafluoro butane; perfluoro-1-butene; perfluoro-1-butene; perfluoro-2-butene; 2-chloro-1,1,1,4,4,4-hexafluoro-butyne; perfluoro-2-butyne; octafluoro-cyclobutane; perfluoro-cyclobutane; perfluoroet-hane; perfluoropropane; perfluorobutane-perfluoropentane; perfluorohexane; 1,1,1-trifluorodiazoethane; hexafluoro-dimethyl amine; perfluorodimethylamine; 4-methyl, 1,1,1, 2-tetrafluoro ethane; 1,1,1-trifluoroethane; 1,1,2,2-tetrafluoroethane; 1,1,2-trichloro-1,2,2-trifluoroethane; 1,1-dichloro-1,2,2,2-tetrafluoro ethane; 1,2-difluoro ethane; 1-chloro-1,1,2,2,2-pentafluoro ethane; 2-chloro, 1,1-difluoroethane; 1-chloro-1,1,2,2-tetrafluoro ethane; 2-chloro, 1,1-difluoroethane; chloropentafluoro ethane; dichlorotrifluoroethane; fluoro-ethane; hexafluoroethane, nitro-pentafluoro ethane, nitroso-pentafluoro ethane; perfluoro ethane; perfluoro ethylamine; 1,1-dichloro-1,2-difluoro ethylene; 1,2-difluoro ethylene; methanesulfonyl chloridetrifluoro; methanesulfonyl fluoride-trifluoro; methane-(pentafluoro-thio)trifluoro; methanebromo difluoro nitroso-methane-bromo fluoro; methane-bromo chlorof-luoro; methanebromotrifluoro; methane-chloro difluoro nitro; methanechloro fluoro; methanechloro trifluoro; methane-chloro-difluoro; methane dibromo difluoro; methane-dichloro difluoro; methanedichloro-fluoro; methanedifluoro; methane-difluoro-iodo; methane-fluoro; methane-iodotrifluoro; methane-nitro-trifluoro; methane-nitroso-trifluoro; methane-tetrafluoro; methanetrichlorof-luoro; methane-trifluoro; methanesulfenylchloride-trifluoro; pentane perfluoro; pentane-perfluoro; propane-1,1,1,2,2,3-hexafluoro; propane-2,2 difluoro; propaneheptafluoro-1-nitro; propane-heptafluoro-1-nitroso; propane-perfluoro; propyl-1,1,1,2,3,3 hexafluoro-2,3 dichloro; propylene-3-fluoro; propylene-perfluoro; propyne-3,3,3-trifluoro; styrene-3-fluoro; sulfur hexafluoride; sulfur (di)-decafluoro; trifluoroacetonitrile; trifluoromethyl peroxide; trifluorom-ethyl sulfide; tungsten hexafluoride, pentafluoro octadecyl iodide, perfluorooctylbromide, perfluorodecalin, perfluorododecalin, perfluorooctyliodide, perfluorotripropylamine, and perfluorotributylamine, hexafluoropropylene, bromochlorofluoromethane, octafluoropropane, 1,1 dichloro, fluoro ethane, hexa fluoroethane, hexafluoro-2-butyne, perfluoropentane, perfluorobutane, octafluoro-2-butene, hexafluorobuta-1,3-diene, octafluorocyclopentene;

wherein said lipid comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dipalnitoylphosphatidylethanolamine-PEG 5,000, dioleoyl-phosphatidylethanolamine, and N-succinyl-dioleoyl-phosphatidylethanolamine; and said phosphatidic acid is dipalmatoylphosphatidic acid.

39. The method of claim 38 wherein said fluorinated gas or gaseous precursor is selected from the group consisting of perfluoromethane, perfluoroethane, perfluoropropane, perfluorobutane, perfluoropentane, perfluorohexane, sulfur hexafluoride, hexafluoropropylene, octafluoropropane, perfluorocyclobutane, octafluorocyclopentene, dodecafluoropentane, and octafluorocyclobutane.

40. The method of claim 39 wherein said fluorinated gas is selected from the group consisting of perfluoromethane, perfluoroethane, perfluoropropane, perfluorobutane, perfluorocyclobutane, and sulfur hexafluoride.

41. The method of claim 40 wherein said fluorinated gas or gaseous precursor is selected from the group consisting of perfluoropropane, perfluorocyclobutane, and perfluorobutane.

42. The method of claim 41 wherein said fluorinated gas or gaseous precursor is perfluoropropane.

43. The method of claim 38 wherein said fluorinated gas or gaseous precursor is a perfluorocarbon gas.

44. The method of claim 32 wherein said microspheres are liposomes formyd from lipid monolayers.

45. The method of claim 38 wherein said microspheres are are liposomes formed from lipid monolayers.

46. The method of claim 44 wherein said lipid comprises a phospholipid.

47. The method of claim 46 wherein said fluorinated gas or gaseous precursor is selected from the group consisting of perfluoropropane, perfluorobutane, perfluoropentane, perfluorohexane, and sulfur hexafluoride.

48. The method of claim 47 wherein said fluorinated gas or gaseous precursor is perfluoropentane.

49. The method of claim 47 wherein said fluorinated gas or gaseous precursor is sulfur hexafluoride.

50. The method of claim 47 wherein said fluorinated gas or gaseous precursor is perfluorobutane.

51. The method of claim 45 wherein said lipid comprises a phospholipid.

52. The method of claim 51 wherein said fluorinated gas or gaseous precursor is selected from the group consisting of perfluoropropane, perfluorobutane, perfluoropentane, perfluorohexane, and sulfur hexafluoride.

53. The method of claim 52 wherein said fluorinated gas or gaseous precursor is perfluoropentane.

54. The method of claim 52 wherein said fluorinated gas or gaseous precursor is sulfur hexafluoride.

55. The method of claim 52 wherein said fluorinated gas or gaseous precursor is perfluoropropane.

56. The method of claim 32 or 33 wherein said microspheres further comprise a polymer and said gas in said gas or gaseous precursor-filled microspheres further comprises air.

57. The method of claim 32 or 38 wherein said microspheres further comprise a polysaccharide and said gas in said gas or gaseous precursor-filled microspheres further comprises nitrogen.

58. The method of claim 57 wherein said polysaccharide comprises galactose and said gas in said gas-filled microspheres further comprises nitrogen.

59. The method of claim 44 wherein said lipid comprises a polymerized lipid.

60. The method of claim 45 wherein said lipid comprises a polymerized lipid.

61. The method of claim 44 wherein said microspheres further comprise polyethylene glycol.

62. The method of claim 45 wherein said microspheres further comprise polyethylene glycol.

* * * * *

UNITED STATES PATENT AND TRADEMARK OFFICE
CERTIFICATE OF CORRECTION

PATENT NO. : 6,479,034 B1
DATED : November 12, 2002
INVENTOR(S) : Evan C. Unger et al.

It is certified that error appears in the above-identified patent and that said Letters Patent is hereby corrected as shown below:

Title page,
Item [60], Related U.S. Application Data, please insert -- now Pat No. 5,585,112 -- after "Nov. 30, 1993".
Item [56], References Cited, U.S. PATENT DOCUMENTS,
"4,229,360 A 11/1991 Schneider et al.", reference, please delete "A" and insert -- B1 -- therefor; please insert reference -- 5,505,932 4/1996 Grinstaff et al. 424/9.3 --.
FOREIGN PATENT DOCUMENTS,
"WO 84102909", reference, please delete "8/1994"
and insert -- 8/1984 – therefor.
Please insert reference -- WO 92/11873 7/1992 --.
OTHER PUBLICATIONS,
"Porter, T.R., et al.," reference, please delete "injunction" and insert -- injection -- therefor.
"Porter, T.R., at al.," reference, please delete "myocardinal" and insert -- myocardial -- therefor.
"Tilcock, C. et al.," reference, please delete "and" and insert -- the –;please delete "of' and insert -- on -- therefor.
"Yang et al.," reference, please delete "Facture" and insert -- Fracture -- therefor.
"Fukuda et al.," reference, please delete "Diotadecyldimethylammonium" and insert -- Dioctadecyldimethylammonium -- therefor,
"Shiina et al.," reference, please delete "Hyperthermiably" and insert -- Hyperthermia by -- therefor.
"Ter-Pogossian," reference, please delete "*Tomography*, Kee, et al., n,"; after "Computed Body," please insert -- *Tomography*, Lee, et at., -- therefor.
"Kee, et al.," reference, please delete "Kee" and insert -- Lee -- therefor.
"Villanueva et al.," reference, please delete "Patters" and insert -- Patterns -- therefor.
Please insert reference – Hynynen et at., "The Usefulness of a Contrast Agent and Gradient Recalled Acquisition in a Steady-State Imaging Sequence for Magnetic Resonance Imaging-Guided Noninvasive Ultrasound Surgery," *Investigative Radiology*, 1994, 29(10) 897-903. --

Column 1,
Line 9, please insert -- now U.S. Pat No. 5,585,112 -- after "Nov. 30, 1993".

Column 11,
Line 42, please delete "dipalimitoylphosphatidylcholine" and insert --dipalmitoylphosphatidylcholine -- therefor.

Column 12,
Line 7, please delete "athan" and insert -- than -- therefor.

UNITED STATES PATENT AND TRADEMARK OFFICE
CERTIFICATE OF CORRECTION

PATENT NO. : 6,479,034 B1
DATED : November 12, 2002
INVENTOR(S) : Evan C. Unger et al.

It is certified that error appears in the above-identified patent and that said Letters Patent is hereby corrected as shown below:

Column 19,
Line 21, Table II, please delete "docecafluoro" and insert -- dodecafluoro -- therefor.

Column 20,
Line 44, please delete " preferrably " and insert -- preferably -- therefor.

Column 33,
Line 33, please delete "hesafluoropropylene" and insert -- hexafluoropropylene -- therefor.
Line 35, please delete "hesafluoro–2–butyne" and insert -- hexafluoro–2–butyne -- therefor.

Column 36,
Line 49, please delete "$F_2$" and insert -- $F_{2\alpha}$ -- therefor.

Column 37,
Line 20, please delete "liposbmes" and insert -- liposomes -- therefor:

Column 38,
Line 2, please delete "thealiposomes" and insert --the liposomes -- therefor.

Column 40,
Line 47, please delete "Dipalmitoyphosphatidylcholine" and insert
-- Dipalmitoylphosphatidylcholine -- therefor.

Column 41,
Line 13, please delete "ws" and insert -- was -- therefor.
Line 26, please delete "EXAMPLE A" and insert -- EXAMPLE 4A -- therefor.
Line 31, please delete "distearoyl-sn-glycerophospate" and insert -- distearoyl-s) glycerophosphate -- therefor.

Column 43,
Line 4, please delete "mL" and insert -- $mL^{-1}$ -- therefor.

Column 48,
Line 46, please delete "exeriment" and insert -- experiment -- therefor.

Column 49,
Line 25, please delete "dipalmatoylphosphatidic" and insert -- dipalmitoylphosphatidic -- therefor.
Line 58, please delete "dipalmatoylphosphatidic" and insert -- dipalmitoylphosphatidic -- therefor.

UNITED STATES PATENT AND TRADEMARK OFFICE
CERTIFICATE OF CORRECTION

PATENT NO. : 6,479,034 B1
DATED : November 12, 2002
INVENTOR(S) : Evan C. Unger et al.

It is certified that error appears in the above-identified patent and that said Letters Patent is hereby corrected as shown below:

Column 51,
Line 24, please delete "dipalmatoylphosphatidic" and insert -- dipalmitoylphosphatidic -- therefor.

Column 53,
Line 4, please delete "dipalmatoylphosphatidic" and insert -- dipalmitoylphosphatidic -- therefor.

Column 54,
Line 25, please delete "dipalnitoylphosphatidylethanolamine-PEG 5,000" and insert -- dipalmitoylphosphatidylethanolamine-PEG 5,000 -- therefor.
Line 28, please delete "dipalmatoylphosphatidic" and insert dipalmitoylphosphatidic -- therefor.
Line 49, please delete "formyd" and insert -- formed -- therefor.

Signed and Sealed this

Seventeenth Day of May, 2005

JON W. DUDAS
*Director of the United States Patent and Trademark Office*